United States Patent
Matsuzaki et al.

(10) Patent No.: US 11,849,728 B2
(45) Date of Patent: Dec. 26, 2023

(54) METHOD FOR CONTROLLING SOYBEAN RUST FUNGUS HAVING RESISTANCE AGAINST QO SITE INHIBITOR

(71) Applicant: SUMITOMO CHEMICAL COMPANY, LIMITED, Chuo-ku (JP)

(72) Inventors: Yuichi Matsuzaki, Takar

-continued

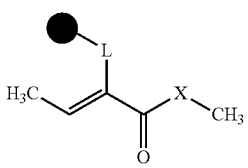

5 Claims, No Drawings

(51) Int. Cl.
    *A01N 43/56* (2006.01)
    *A01N 37/50* (2006.01)
    *C07C 69/736* (2006.01)

(56) References Cited

U.S. PATENT DOCUMENTS

| 5,464,809 | A | 11/1995 | Krämer et al. |
| 6,489,487 | B1 | 12/2002 | Manabe et al. |

FOREIGN PATENT DOCUMENTS

| JP | 2006-239261 A | 9/2000 | |
| JP | 2001-64237 A | 3/2001 | |
| JP | 2001-114737 A | 4/2001 | |
| WO | WO 98/3464 A1 | 1/1998 | |
| WO | WO-9803464 A1 * | 1/1998 | ............. A01N 39/02 |
| WO | WO 01/00562 A1 | 1/2001 | |

OTHER PUBLICATIONS

International Search Report dated Sep. 10, 2019 in PCT/JP2019/030056 (submitting English translation only), 3 pages.
International Preliminary Report on Patentability and Written Opinion dated Feb. 2, 2021 in PCT/JP2019/030058 (submitting English translation only), 9 pages.
Ishii, Hideo, "QoI agent-resistant bacteria", Plant protection, vol. 69, No. 8 , pp. 469-474.
Di Rago, J.-P., et al., "Molecular Basis for Resistance to Myxothiazol, mucidin (Strobilurin A), and Stigmatellin", Journal of Biological Chemistry, (1989), vol. 264(24),p. 14543-14548.
Bennoun, P., et al., "Mitochondrial Genetics of *Chlamydomonas reinhardtir.* Resistance Mutations Marking the Cytochrome b Gene" Genetics (1991), vol. 127.p. 335-343.
Zheng, D., et al., "Characterization of laboratory mutants of *Venturia inaequalis* resistant to the strobilurin-related fungicide kersoxim-methyl", Current Genetics (2000),vol. 38,p. 148-155.
Schmitz, H.K., et al., "Sensitivity of *Phakopsora pachyrhizi* towards quinone-outside-inhibitors and demethylation-inhibitors, and corresponding resistance mechanisms†", Pest Management Science (2014),vol. 70(3),p. 378-388.
Godoy, C.V., et al., "Asian soybean rust in Brazil: past, present, and future", Presq. agropec. Bras. (Basilia), (2016), vol. 51.5, p. 407-421.
Leiminger, J.H., et al., "Occurrence of the F129L mutation in *Altemaria solani* populations in Germany in response to QoI application, and its effect on Sensitivity", Plant Pathology (2014), vol. 63(3), p. 640-650.
Pasche, J.S., et al., "Shift in Sensitivity of *Altemaria solani* in Response to QoI Fungicides", Plant Disease (2004), vol. 88(2), p. 181-187.
Pasche, J.S., et al., "Effect of the F129L Mutation in *Altemaria solani* on Fungicides Affecting Mitochondrial Respiration", Plant Disease (2005), vol. 89(3), p. 269-278.
Kim, Y.-S., et al., "Field Resistance to Strobilurin (QoI) Fungicides in *Pyricuiaria grisea* Caused by Mutations in the Mitochondrial Cytochrome b Gene", Phytopathology(2003), vol. 93(7), p. 891-900.
Odilbekov, F., et al., "Genetic diversity and occurrence of the F129L substitutions among isolates of *Altemaria solani* in south-eastern Sweden", Hereditas, (Lund)(Sep. 23, 2016) vol. 153. pp. Article No. 10, pp. 1-10.
Klosowki, A.C., et al., "Competitive Fitness of *Phakopsora pachyrhizi* Isolates with Mutations in the CYP51 and CYTB Genes", Phytopathology (2016), vol. 106(11), 1278-1284.
Klosowki, A.C., et al., "Detection of the F129L mutation in the cytochrome b gene in *Phakopsora pachyrhizi*" Pest Management Science (2016),vol. 72(6), 1211-1215.
Office Action dated Mar. 30, 2022, in corresponding Chinese Patent Application No. 201980050215.5 (with English Translation), 11 pages.
Extended European Search Report dated Jun. 3, 2022, in European Patent Application No. 19843920.0, 7 pages.
Chinese Office Action dated Sep. 29, 2022 in Chinese Patent Application No. 201980050215.5 (with unedited computer generated English Translation), 10 pages.
Indian Office Action dated Aug. 3, 2022 in Indian Patent Application No. 202147002643, 7 pages.
Office Action dated Jul. 4, 2023 in the corresponding Japanese Patent Application No. 2020-534712, filed Jul. 31, 2019 (with English-language Translation), 11 pages.
European Office Action dated Apr. 12, 2023 in European Patent Application No. 19 843 920.0, 4 pages.

\* cited by examiner

METHOD FOR CONTROLLING SOYBEAN RUST FUNGUS HAVING RESISTANCE AGAINST QO SITE INHIBITOR

CROSS-REFERENCE TO RELATED APPLICATIONS

The present application is a 35 U.S.C. § 371 national stage patent application of International patent application PCT/JP2019/030058, filed on Jul. 31, 2019, which is based on and claims the benefits of priority to Japanese Application No. 2018-143528, filed on Jul. 31, 2018. The entire contents of these applications are incorporated herein by reference.

TECHNICAL FIELD

This application claims priority to and the benefit of Japanese Patent Application No. 2018-143528 filed on Jul. 31, 2018, the entire contents of which are incorporated herein by reference.

The present invention relates to a method for controlling soybean rust fungus having an amino acid substitution of F129L on mitochondrial cytochrome b protein.

BACKGROUND ART

The spread of phytopathogenic fungi that shows acquired character being resistant to agricultural fungicides becomes a major problem. Under such circumstances, FRAC (Fungicide Resistance Action Committee) has been established as an organization that provides guidelines for acquiring a resistance to existing agricultural fungicides, and suppressing and delaying the spread of the fungi having the resistance acquired. A variety of information on phytopathogenic fungi that shows a resistance to agricultural fungicides is available on the FRAC-provided website (http://www.frac.info/). It has been known that in the case of a phytopathogenic fungi, the main cause of acquiring a resistance is that a mutation of the phytopathogenic fungal gene encoding the target enzyme of the fungicide causes a partial substitution of amino acids in the target enzyme of the fungicides, which results in reducing the affinity between the fungicides and the target enzyme.

QoI fungicides are named as aliases a strobilurin fungicide, or a methoxyacrylate fungicide because of its characteristic structure. The QoI fungicides are one group of agricultural fungicides that have been widely used to control phytopathogenic fungi including soybean rust fungus. QoI fungicides usually bind to the ubihydroquinone oxidation centers of cytochrome bc1 complex (electron transfer complex III) in mitochondria, and suppress a respiration of the phytopathogenic fungi, which results in killing the phytopathogenic fungi or stopping the growth of the same. The above-mentioned oxidation center is located outside the mitochondrial inner membrane (see Non-patent document 1).

It has been revealed by model studies in the laboratory before QoI fungicides were actually used extensively as agricultural fungicides that phytopathogenic fungi are subjected to a selection pressure by QoI fungicide, which results in easily generating the fungi having a resistance to a QoI fungicide that has acquired a gene mutation that causes a specific single amino acid substitution such as G143A in the cytochrome b gene of the target enzyme cytochrome bc1 complex (see Non-patent documents 2 to 4).

On the other hand, soybean rust fungus (scientific name: *Phakopsora pachyrhizi*) is a phytopathogenic fungus that causes damages to soybeans. Since QoI fungicides have been widely used for controlling soybean rust disease as agricultural fungicides, an emergence of soybean rust fungi showing a resistance to the QoI fungicides has been reported (see Non-patent document 5).

For soybean rust fungus, a strain which has acquired a gene mutation causing a single amino acid substitution of F129L in the same cytochrome b gene becomes a problem as a resistant fungus against QoI fungicide. The efficacy of the QoI fungicides conventionally used against soybean rust fungi, that is, pyraclostrobin, azoxystrobin, picoxystrobin, orisastrobin, dimoxystrobin, metominostrobin, pyribencarb and the others, has been reduced to the level of practical problems against the resistant fungi (see Non-patent document 6).

CITATION LIST

Non-Patent Document

Non-Patent Document 1: Sauter, "Modern Crop Protection Compounds", Volume 2, Wiley-VCH Verlag, 2007, p. 457-495: the 13.2 Chapter, Strobilurins and other complex III inhibitors;

Non-Patent Document 2: "Journal of Biological Chemistry", 1989, Volume 264, no. 24, p. 14543-14548

Non-Patent Document 3: "Genetics", 1991, Volume 127, p. 335-343

Non-Patent Document 4: "Current Genetics", 2000, Volume 3, p. 148-155

Non-Patent Document 5: "Pest Management Science", 2014, Volume 70, no. 3, p. 379-388

Non-Patent Document 6: "Pesq. agropec. bras." (Brasilia), 2016, Volume 51, no. 5, p. 407-421

SUMMARY OF THE INVENTION

Problems to be Solved by Invention

On the basis of these facts, the present invention aims to provide a method for controlling soybean rust fungus having an amino acid substitution of F129L on mitochondrial cytochrome b protein.

Means to Solve Problems

The present invention is as follows.

[1] A method for controlling a soybean rust fungus having an amino acid substitution of F129L on mitochondrial cytochrome b protein, which comprises applying an effective amount of a compound represented by formula (I):

$$\underset{E}{\overset{(R^2)_n}{\bigtriangleup}}\overset{R^1}{\underset{Q}{\bigtriangleup}} \quad (I)$$

[wherein Q represents a group represented by the following Q1, Q2, Q3, Q4 or Q5 (in the formulae, ● represents a binding site to benzene ring),

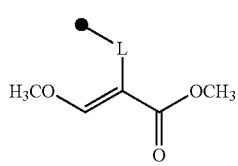

Q1

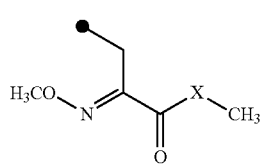

Q2

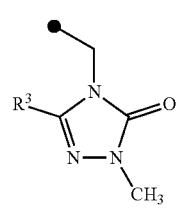

Q3

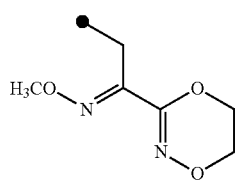

Q4

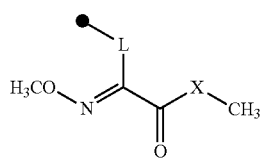

Q5

X represents an oxygen atom or NH,
L represents $CH_2$, an oxygen atom, or $NCH_3$,
E represents $R^4R^5C=C(R^6)-$, $R^7-C\equiv C-$, $R^{14}O-N=C(R^9)-$, $R^8R^9C=N-O-CH_2-$, $R^8O-N=C(R^9)-C(R^{10})=NO-CH_2-$, $R^8C(O)-C(R^9)=N-O-CH_2-$, $R^8C(=N-O-R^9)-C(R^{10})=N-O-CH_2-$, a C5-C6 cycloalkenyl group, a C6-C10 aryl group or a five to ten-membered aromatic heterocyclic group {the C5-C6 cycloalkenyl group, the C6-C10 aryl group, and the five- to ten-membered aromatic heterocyclic group each may be optionally substituted with one or more substituents selected from Group D},
$R^1$ represents a C1-C3 chain hydrocarbon group optionally substituted with one or more halogen atoms, a cyclopropyl group, a halogen atom, or a hydrogen atom,
n is 0, 1, 2, or 3,
when n is 2 or 3, a plural of $R^2$ may be identical to or different from each other,
$R^2$ represents a C1-C3 chain hydrocarbon group optionally substituted with one or more halogen atoms, a cyclopropyl group, or a halogen atom,
$R^3$ represents a C1-C3 alkoxy group optionally substituted with one or more halogen atoms, or a C1-C3 chain hydrocarbon group optionally substituted with one or more halogen atoms,
$R^4$ and $R^6$ are identical to or different from each other and represent a C1-C3 chain hydrocarbon group optionally substituted with one or more halogen atoms, a halogen atoms, a cyano group, or a hydrogen atom,
$R^5$ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-membered aromatic heterocyclic group {the C6-C10 aryl group and the five- to ten-aromatic heterocyclic group each may be optionally substituted with one or more substituents selected from Group D}, a halogen atom, a cyano group, or a hydrogen atom;
$R^7$ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-aromatic heterocyclic group {the C6-C10 aryl group and the five- to ten-aromatic heterocyclic group may be optionally substituted with one or more substituents selected from Group D}, or $SiR^{20}R^{21}R^{22}$,
$R^8$ represents a C1-C6 chain hydrocarbon group optionally substituted with one or more substituents selected from Group A, a C3-C6 cycloalkyl group optionally substituted with one or more substituents selected from Group B, a C6-C10 aryl group, or a five- to ten-aromatic heterocyclic group {the C6-C10 aryl group, and the five- to ten-aromatic heterocyclic group may be optionally substituted with one or more substituents selected from Group D},
$R^9$, $R^{10}$ and $R^{17}$ are identical to or different from each other and represent a C1-C3 chain hydrocarbon group optionally substituted with one or more halogen atoms, or a hydrogen atom,
$R^{14}$ represents a C1-C6 chain hydrocarbon group optionally substituted with one or more substituents selected from Group A, a C3-C6 cycloalkyl group optionally substituted with one or more substituents selected from Group B, $R^{15}C(O)-$, $R^{16}OC(O)-$, $R^{15}R^{17}NC(O)-$, a C6-C10 aryl group, or a five- to ten-aromatic heterocyclic group {the C6-C10 aryl group, and the five- to ten-aromatic heterocyclic group may be optionally substituted with one or more substituents selected from Group D},
$R^{15}$ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-aromatic heterocyclic group {the C6-C10 aryl group and the five- to ten-aromatic heterocyclic group may be optionally substituted with one or more substituents selected from Group D}, or a hydrogen atom,
$R^{16}$ represents a C1-C6 chain hydrocarbon group optionally substituted with one or more substituents selected from Group A, a C3-C6 cycloalkyl group optionally substituted with one or more substituents selected from Group B, a C6-C10 aryl group, or a five- to ten-aromatic heterocyclic group {the C6-C10 aryl group and the five- to ten-aromatic heterocyclic group may be optionally substituted with one or more substituents selected from Group D}, $R^{20}$, $R^{21}$ and $R^{22}$ are identical to or different from each other and represent a C1-C6 chain hydrocarbon group, or a phenyl group, Group A: a group consisting of a C3-C6 cycloalkyl group, a C1-C4 alkoxy group, a C1-C4 alkylthio group {the C3-C6 cycloalkyl group, the C1-C4 alkoxy group, and the C1-C4 alkylthio group each may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group may be optionally substituted with one or more substituents selected from Group C}, Group B: a group consisting of a C1-C6 chain hydrocarbon group, a C3-C6 cycloalkyl group, a C1-C4 alkoxy group, a C1-C4 alkylthio group {the C1-C6 chain hydrocarbon group, the C3-C6 cycloalkyl group, the C1-C4 alkoxy group, and the C1-C4 alkylthio group each may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C}, Group C: a group consisting of a C1-C6 chain hydrocarbon group, a C3-C6 cycloalkyl group, a C1-C6 alkoxy group, and a C1-C6 alkylthio group {the C1-C6 chain hydrocarbon group, the C3-C6 cycloalkyl group, the C1-C6 alkoxy group, and the C1-C6 alkylthio group may be optionally substituted with one or more substituents selected from the group consisting of halogen atom and cyano group}, a halogen atom, a cyano group, a nitro group, and a hydroxy group, Group D: a group consisting of a C1-C6 chain hydrocarbon group optionally substituted with one or more substituents selected from Group A, a C3-C6 cycloalkyl group optionally substituted with one or more substituents selected from Group B, $OR^{11}$, $S(O)_m R^{13}$, $OS(O)_2 R^{13}$, $C(O)R^{11}$, $C(O)OR^{11}$, $NR^{11}R^{12}$, $C(P)NR^{11}R^{12}$, $S(O)_2 NR^{11}R^{12}$, $NR^{12}C(O)R^{11}$, $NR^{12}C(O)OR^{13}$, $NR^{12}S(O)_2 R^{13}$, $C(R^{12})=N-OR^{11}$, a phenyl group, a naphthyl group, a five- to six-membered aromatic heterocyclic group {the phenyl group, the naphthyl group, and the five- to six-membered aromatic heterocyclic group may be optionally substituted with one or more substituents selected from Group C}, an oxo group, a thioxo group, a halogen atom, a cyano group, and a nitro group, $R^{11}$ and $R^{12}$ are identical to or different from each other and represent a C1-C6 chain hydrocarbon group optionally substituted with one or more substituents selected from Group A, a C3-C6 cycloalkyl group optionally substituted with one or more substituents selected from Group B, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C} or a hydrogen atom, $R^{13}$ represents a C1-C6 chain hydrocarbon group optionally substituted with one or more substituents selected from Group A, a C3-C6 cycloalkyl group optionally substituted with one or more substituents selected from Group B, a phenyl group, a naphthyl group, or a five- to six-membered aromatic heterocyclic group {the phenyl group, the naphthyl group, and the five- to six-membered aromatic heterocyclic group each may be optionally substituted with one or more substituents selected from Group C}, and m is 0, 1, or 2]

(hereinafter, referred to as "Present Compound Z"), or its N oxide or an agriculturally acceptable salt thereof (hereinafter, the compound represented by formula (I), or its N oxide, or an agriculturally acceptable salt thereof is collectively referred to as "Present Compound") to soybean or soil where soybean is grown.

[2] The method according to [1] wherein the compound represented by formula (I), or its N oxide, or an agriculturally acceptable salt thereof represents a compound represented by formula (I) wherein Q represents a group represented by Q1, Q2 or Q3

L represents $CH_2$ or an oxygen atom,

E represents $R^7-C\equiv C-$, $R^8 O-N=C(R^9)-$, a phenyl group, a thienyl group, a pyridyl group, or a pyrazolyl group {the phenyl group, the thienyl group, the pyridyl group, and the pyrazolyl group each may be optionally substituted with one or more substituents selected from Group C}, $R^1$ represents a methyl group or a chlorine atom, n is 0, $R^3$ represents a difluoromethyl group or a methoxy group, $R^7$ represents a C1-C6 chain hydrocarbon group optionally substituted with one or more substituents selected from Group A, a C3-C6 cycloalkyl group optionally substituted with one or more substituents selected from Group B, a phenyl group optionally substituted with one or more substituents selected from Group C, or $SiR^{20}R^{21}R^{22}$, $R^8$ represents a C1-C6 chain hydrocarbon group optionally substituted with one or more substituents selected from Group A, and $R^9$ represents a methyl group, or its N oxide, or an agriculturally acceptable salt thereof.

[3] Use of the compound represented by formula (I) described in [1] or [2], or its N oxide, or an agriculturally acceptable salt thereof for controlling a soybean rust fungus having an amino acid substitution of F129L on mitochondrial cytochrome b protein.

[4] A compound represented by formula (II):

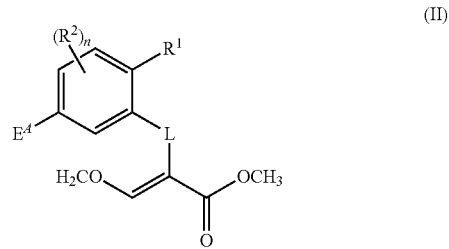

[wherein

L represents $CH_2$, an oxygen atom, or $NCH_3$, $E^A$ represents $R^4R^5C=C(R^6)-$, $R^{7A}-C\equiv C-$, or a 1-pyrazolyl group {the 1-pyrazolyl group may be optionally substituted with one or more substituents selected from Group E}, $R^1$ represents a C1-C3 chain hydrocarbon group optionally substituted with one or more halogen atoms, a cyclopropyl group, a halogen atom, or a hydrogen atom, n represents 0, 1, 2, or 3, when n is 2 or 3, a plural of $R^2$ may be identical to or different from each other, $R^2$ represents a C1-C3 chain hydrocarbon group optionally substituted with one or more halogen atoms, a cyclopropyl group, or a halogen atom, $R^4$ and $R^6$ are identical to or different from each other and represent a C1-C3 chain hydrocarbon group optionally substituted with one or more halogen atoms, a halogen atom, a cyano group, or a hydrogen atom, $R^5$ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-aromatic heterocyclic group {the C6-C10 aryl group, and the five- to ten-aromatic heterocyclic group each may be optionally substituted with one or more substituents selected from Group D}, a halogen atom, a cyano group, or a hydrogen atom, $R^{7A}$ represents a cyclopropyl group, or a cyclobutyl group {the cyclopropyl group, and the cyclobutyl group each may be optionally substituted with one or more substituents selected from Group B}, Group A: a group consisting of a C3-C6 cycloalkyl group, a C1-C4 alkoxy group, a C1-C4 alkylthio group {the C3-C6 cycloalkyl group, the C1-C4 alkoxy group, and the C1-C4 alkylthio group each may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C}, Group B: a group consisting of a C1-C6 chain hydrocarbon group, a C3-C6 cycloalkyl group, a C1-C4 alkoxy group, a C1-C4 alkylthio group {the C1-C6 chain hydrocarbon group, the C3-C6 cycloalkyl group, the C1-C4 alkoxy group, and the C1-C4 alkylthio group each may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C}, Group C: a group consisting of a C1-C6 chain hydrocarbon group, a C3-C6 cycloalkyl group, a C1-C6 alkoxy group, and a C1-C6 alkylthio group {the C1-C6 chain hydrocarbon group, the C3-C6 cycloalkyl group, the C1-C6 alkoxy group, and the C1-C6 alkylthio group each may be optionally substituted with one or more substituents selected from the group consisting of halogen atom and cyano group}, a halogen atom, a cyano group, a nitro group, and a hydroxy group, Group D: a group consisting of a C1-C6 chain hydrocarbon group optionally substituted with one or more substituents selected from Group A, a C3-C6 cycloalkyl group optionally substituted with one or more substituents selected from Group B, $OR^{11}$, $S(O)_mR^{13}$, $OS(O)_2R^{13}$, $C(O)R^{11}$, $C(O)OR^{11}$, $NR^{11}R^{12}$, $C(O)NR^{11}R^{12}$, $S(O)_2NR^{11}R^{12}$, $NR^{12}C(O)R^{11}$, $NR^{12}C(O)OR^{13}$, $NR^{12}S(O)_2R^{13}$, $C(R^{12})=N-OR^{11}$, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C}, an oxo group, a thioxo group, a halogen atom, a cyano group, and a nitro group, $R^{11}$ and $R^{12}$ are identical to or different from each other and represent a C1-C6 chain hydrocarbon group optionally substituted with one or more substituents selected from Group A, a C3-C6 cycloalkyl group optionally substituted with one or more substituents selected from Group B, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C}, or a hydrogen atom, and $R^{13}$ represents a C1-C6 chain hydrocarbon group optionally substituted with one or more substituents selected from Group A, a C3-C6 cycloalkyl group optionally substituted with one or more substituents selected from Group B, a phenyl group, a naphthyl group, or a five- to six-membered aromatic heterocyclic group {the phenyl group, the naphthyl group, and the five- to six-membered aromatic heterocyclic group each may be optionally substituted with one or more substituents selected from Group C}, m is 0, 1, or 2, Group E: a group consisting of a C1-C6 chain hydrocarbon group optionally substituted with one or more substituents selected from Group A, a C3-C6 cycloalkyl group optionally substituted with one or more substituents selected from Group B, $OR^{11}$, $S(O)_mR^{13}$, $OS(O)_2R^{13}$, $C(O)R^{11}$, $C(O)OR^{11}$, $NR^{11}R^{12}$, $C(O)NR^{11}R^{12}$, $S(O)_2NR^{11}R^{12}$, $NR^{12}C(O)R^{11}$, $NR^{12}C(O)OR^{13}$, $NR^{12}S(O)_2R^{13}$, $C(R^{12})=N-OR^{11}$, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C}, a halogen atom, a cyano group, and a nitro group]

(hereinafter, referred to as "Compound Z of the present invention"), or its N oxide, or an agriculturally acceptable salt thereof (hereinafter, the compound represented by formula (II), or its N oxide, or an agriculturally acceptable salt thereof is collectively referred to as "Compound of the present invention").

[5] The compound according to [4] wherein
L represents CH$_2$ or an oxygen atom,
R$^1$ represents a methyl group or a chlorine atom,
n is 0,
R$^4$ and R$^6$ are identical to or different from each other and represent a C1-C3 chain hydrocarbon group, or a hydrogen atom,
R$^5$ represents a C1-C6 chain hydrocarbon group optionally substituted with one or more substituents selected from Group A, or a hydrogen atom, and
R$^{7A}$ represents a cyclopropyl group,
or its N oxide, or an agriculturally acceptable salt thereof.

[6] An agricultural composition comprising the compound according to [4] or [5], or its N oxide, or an agriculturally acceptable salt thereof, and an inert carrier.

[7] An agricultural composition comprising one or more ingredients selected from Group (a), Group (b), Group (c) and Group (d),
Group (a): a group consisting of insecticidal ingredients, miticidal ingredients, and nematicidal ingredients;
Group (b): fungicidal ingredients;
Group (c): plant growth modulating ingredients; and
Group (d): repellent ingredients.

[8] A compound represented by formula (III):

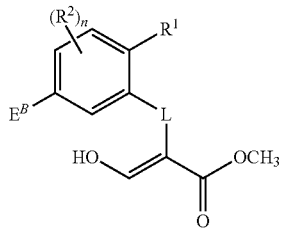

[wherein,
L represents CH$_2$, an oxygen atom, or NCH$_3$,
E$^B$ represents R$^4$R$^5$C=C(R$^6$)— or R$^{7A}$—C≡C—,
R$^1$ represents a C1-C3 chain hydrocarbon group optionally substituted with one or more halogen atoms, a cyclopropyl group, a halogen atom, or a hydrogen atom,
n represents 0, 1, 2, or 3,
when n is 2 or 3, a plural of R$^2$ may be identical to or different from each other,
R$^2$ represents a C1-C3 chain hydrocarbon group optionally substituted with one or more halogen atoms, a cyclopropyl group, or a halogen atom,
R$^4$ and R$^6$ are identical to or different from each other and represent a C1-C3 chain hydrocarbon group optionally substituted with one or more halogen atoms, a halogen atom, a cyano group, or a hydrogen,
R$^5$ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-aromatic heterocyclic group {the C6-C10 aryl group, and the five- to ten-aromatic heterocyclic group each may be optionally substituted with one or more substituents selected from Group D}, a halogen atom, a cyano group, or a hydrogen atom,
R$^{7A}$ represents a cyclopropyl group, or a cyclobutyl group {the cyclopropyl group and the cyclobutyl group each may be optionally substituted with one or more substituents selected from Group B},
Group A: a group consisting of a C3-C6 cycloalkyl group, a C1-C4 alkoxy group, a C1-C4 alkylthio group {the C3-C6 cycloalkyl group, the C1-C4 alkoxy group, and the C1-C4 alkylthio group each may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C},
Group B: a group consisting of a C1-C6 chain hydrocarbon group, a C3-C6 cycloalkyl group, a C1-C4 alkoxy group, a C1-C4 alkylthio group {the C1-C6 chain hydrocarbon group, the C3-C6 cycloalkyl group, the C1-C4 alkoxy group, and the C1-C4 alkylthio group may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C},
Group C: a group consisting of a C1-C6 chain hydrocarbon group, a C3-C6 cycloalkyl group, a C1-C6 alkoxy group, and a C1-C6 alkylthio group {the C1-C6 chain hydrocarbon group, the C3-C6 cycloalkyl group, the C1-C6 alkoxy group, and the C1-C6 alkylthio group each may be optionally substituted with one or more substituents selected from the group consisting of halogen atom and cyano group}, a halogen atom, a cyano group, a nitro group, and a hydroxy group,
Group D: a group consisting of a C1-C6 chain hydrocarbon group optionally substituted with one or more substituents selected from Group A, a C3-C6 cycloalkyl group optionally substituted with one or more substituents selected from Group B, OR$^{11}$, S(O)$_m$R$^{13}$, OS(O)$_2$R$^{13}$, C(O)R$^{11}$, C(O)OR$^{11}$, NR$^{11}$R$^{12}$, C(O)NR$^{11}$R$^{12}$, S(O)$_2$NR$^{11}$R$^{12}$, NR$^{12}$C(O)R$^{11}$, NR$^{12}$C(O)OR$^{13}$, NR$^{12}$S(O)$_2$R$^{13}$, C(R$^{12}$)=N—OR$^{11}$, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C}, an oxo group, a thioxo group, a halogen atom, a cyano group, and a nitro group,
R$^{11}$ and R$^{12}$ are identical to or different from each other and represent a C1-C6 chain hydrocarbon group optionally substituted with one or more substituents selected from Group A, a C3-C6 cycloalkyl group optionally substituted with one or more substituents selected from Group B, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C} or a hydrogen atom, and $R^{13}$ represents a C1-C6 chain hydrocarbon group optionally substituted with one or more substituents selected from Group A, a C3-C6 cycloalkyl group optionally substituted with one or more substituents selected from Group B, a phenyl group, a naphthyl group, or a five- to six-membered aromatic heterocyclic group {the phenyl group, the naphthyl group, and the five- to six-membered aromatic heterocyclic group each may be optionally substituted with one or more substituents selected from Group C}, m is 0, 1, or 2]

(hereinafter, referred to as "Intermediate compound A").

[9] The compound according to [8] wherein

L represents $CH_2$ or an oxygen atom, $R^1$ represents a methyl group or a chlorine atom, n is 0, $R^4$ and $R^6$ are identical to or different from each other and represent a C1-C3 chain hydrocarbon group, or a hydrogen atom, $R^5$ represents a C1-C6 chain hydrocarbon group optionally substituted with one or more substituents selected from Group A or a hydrogen atom, and $R^{7A}$ represents a cyclopropyl group.

[10] A compound represented by formula (IV):

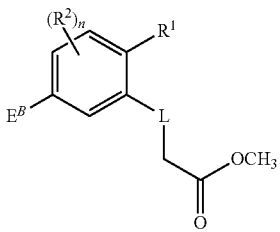

(IV)

[wherein,

L represents $CH_2$, an oxygen atom, or $NCH_3$, $E^B$ represents $R^4R^5C=C(R^6)$— or $R^{7A}$—C≡C—, $R^1$ represents a C1-C3 chain hydrocarbon group optionally substituted with one or more halogen atoms, a cyclopropyl group, a halogen atom, or a hydrogen atom, n represents 0, 1, 2, or 3, when n is 2 or 3, a plural of $R^2$ may be identical to or different from each other, $R^2$ represents a C1-C3 chain hydrocarbon group optionally substituted with one or more halogen atoms, a cyclopropyl group, or a halogen atom, $R^4$ and $R^6$ are identical to or different from each other and represent a C1-C3 chain hydrocarbon group optionally substituted with one or more halogen atoms, a halogen atom, a cyano group, or a hydrogen atom, $R^5$ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-aromatic heterocyclic group {the C6-C10 aryl group, and the five- to ten-aromatic heterocyclic group each may be optionally substituted with one or more substituents selected from Group D}, a halogen atom, a cyano group, or a hydrogen atom, $R^{7A}$ represents a cyclopropyl group, or a cyclobutyl group {the cyclopropyl group and the cyclobutyl group may be optionally substituted with one or more substituents selected from Group B}, Group A: a group consisting of a C3-C6 cycloalkyl group, a C1-C4 alkoxy group, a C1-C4 alkylthio group {the C3-C6 cycloalkyl group, the C1-C4 alkoxy group, and the C1-C4 alkylthio group each may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C}, Group B: a group consisting of a C1-C6 chain hydrocarbon group, a C3-C6 cycloalkyl group, a C1-C4 alkoxy group, a C1-C4 alkylthio group {the C1-C6 chain hydrocarbon group, the C3-C6 cycloalkyl group, the C1-C4 alkoxy group, and the C1-C4 alkylthio group may be optionally substituted with one or more substituents selected from the group consisting of halogen atom and cyano group}, a halogen atom, a cyano group, a nitro group, a hydroxy group, a phenoxy group, a phenyl group, a naphthyl group, and a five- to six-membered aromatic heterocyclic group {the phenoxy group, the phenyl group, the naphthyl group, and the five- to six-membered aromatic heterocyclic group each may be optionally substituted with one or more substituents selected from Group C}, Group C: a group consisting of a C1-C6 chain hydrocarbon group, a C3-C6 cycloalkyl group, a C1-C6 alkoxy group, and C1-C6 alkylthio group {the C1-C6 chain hydrocarbon group, the C3-C6 cycloalkyl group, the C1-C6 alkoxy group, and the C1-C6 alkylthio group each may be optionally substituted with one or more substituents selected from the group consisting of halogen atom and cyano group}, a halogen atom, a cyano group, a nitro group, and a hydroxy group, Group D: a group consisting of a C1-C6 chain hydrocarbon group optionally substituted with one or more substituents selected from Group A, a C3-C6 cycloalkyl group optionally substituted with one or more substituents selected from Group B, $OR^{11}$, $S(O)_mR^{13}$, $OS(O)_2R^{13}$, $C(O)R^{11}$, $C(O)OR^{11}$, $NR^{11}R^{12}$, $C(O)NR^{11}R^{12}$, $S(O)_2NR^{11}R^{12}$, $NR^{12}C(O)R^{11}$, $NR^{12}C(O)OR^{13}$, $NR^{12}S(O)_2R^{13}$, $C(R^{12})=N—OR^{11}$, a phenyl group, a naphthyl group, a five- to six-membered aromatic heterocyclic group {the phenyl group, the naphthyl group, and the five- to six-membered aromatic heterocyclic group each may be optionally substituted with one or more substituents selected from Group C}, an oxo group, a thioxo group, a halogen atom, a cyano group, and a nitro group, $R^{11}$ and $R^{12}$ are identical to or different from each other and represent a C1-C6 chain hydrocarbon group optionally substituted with one or more substituents selected from Group A, a C3-C6 cycloalkyl group optionally substituted with one or more substituents selected from Group B, a phenyl group, a naphthyl group, a five- to six-membered aromatic heterocyclic group {the phenyl group, the naphthyl group, and the five- to six-membered aromatic heterocyclic group may be optionally substituted with one or more substituents selected from Group C} or a hydrogen atom, $R^{13}$ represents a C1-C6 chain hydrocarbon group optionally substituted with one or more substituents selected from Group A, a C3-C6 cycloalkyl group optionally substituted with one or more substituents selected from Group B, a phenyl group, a naphthyl group, or a five- to six-membered aromatic heterocyclic group {the phenyl group, the naphthyl group, and the five- to six-membered aromatic heterocyclic group each may be optionally substituted with one or more substituents selected from Group C}, m is 0, 1, or 2]

(hereinafter, referred to as Intermediate compound B").

[11] The compound according to [10] wherein

L represents $CH_2$ or an oxygen atom, $R^1$ represents a methyl group or a chlorine atom, n is 0, $R^4$ and $R^6$ are identical to or different from each other and represent a C1-C3 chain hydrocarbon group, or a hydrogen atom, $R^5$ represents a C1-C6 chain hydrocarbon group optionally substituted with one or more substituents selected from Group A, or a hydrogen atom, and $R^{7A}$ represents a cyclopropyl group.

Effect of Invention

The present invention can control soybean rust fungus having an amino acid substitution of F129L on mitochondrial cytochrome b protein.

MODE FOR CARRYING OUT THE INVENTION

The substituent(s) as described herein is/are explained.

The term "halogen atom" represents fluorine atom, chlorine atom, bromine atom, or iodine atom.

When the substituent has two or more halogen atoms, these halogen atoms may be identical to or different from each other.

The expression of "CX—CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Examples of the term of "alkyl group" include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group, and hexyl group.

Examples of the term of "alkenyl group" include vinyl group, 1-propenyl group, 2-propenyl group, 1-methyl-1-propenyl group, 1-methyl-2-propenyl group, 1,2-dimethyl-1-propenyl group, 1-ethyl-2-propenyl group, 3-butenyl group, 4-pentenyl group, and 5-hexenyl group.

Examples of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.

Examples of the term of "cycloalkyl group" include cyclopropyl group, cyclobutyl group, cyclopentyl group, and cyclohexyl group.

Examples of the term of "cycloalkenyl group" include cyclopentenyl group, and cyclohexenyl group.

Examples of the term of "aryl group" include phenyl group, naphthyl group, indanyl group, and tetrahydronaphthyl group.

Examples of the aromatic heterocyclic group include a five membered aromatic heterocyclic group such as pyrrolyl group, furanyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group; six-membered aromatic heterocyclic group such as pyridyl group, pyridazinyl group, pyrimidinyl group, pyrazinyl group, triazinyl group, and tetrazinyl group; nine-membered aromatic heterocyclic group such as indazolyl group, indolidinyl group, imidazopyridyl group, and 1,3-benzodioxolyl group; and ten-membered aromatic heterocyclic group such as quinolyl group, isoquinolyl group, quinazolinyl group, naphthyridinyl group, benzopyranyl group, and dihydrobenzopyranyl group.

The present compound, the compound of the present invention, the intermediate compound A, and the intermediate compound B may be existed as one or more stereoisomers. Examples of the stereoisomer include enantiomer, diastereoisomer, and geometric isomer. Each stereoisomer, and stereoisomer mixture(s) in an arbitrary ratio thereof are included in the present compound, the compound of the present invention, the intermediate compound A, and the intermediate compound B.

The term(s) as described herein is/are explained.

The term of "soybean rust fungus having an amino acid substitution of F129L on mitochondrial cytochrome b protein" represents soybean rust fungus (scientific name: *Phakopsora pachyrhizi*) which shows a resistance against QoI fungicide by having a mutation in the mitochondrial cytochrome b gene encoding mitochondrial cytochrome protein and as a result of the mutation, causing amino acid substitution of F129L.

Examples of the agriculturally acceptable salt thereof include acid addition salts such as hydrochloride salts, sulfates, nitrates, phosphates, sulfonates, acetates, and benzoates.

Embodiments of the present compound Z include the following compounds.

[Embodiment 1] A present compound Z wherein $R^4$, $R^6$ and $R^9$ are identical to or different from each other and represent a hydrogen atom or a methyl group; $R^5$ represents a C1-C6 chain hydrocarbon group optionally substituted with one or more substituents selected from Group A, a C3-C6 cycloalkyl group optionally substituted with one or more substituents selected from Group B, or a hydrogen atom; $R^7$ represents a C1-C6 chain hydrocarbon group optionally substituted with one or more substituents selected from Group A, a C3-C6 cycloalkyl group optionally substituted with one or more substituents selected from Group B, a phenyl group optionally substituted with one or more substituents selected from Group C, or $SiR^{20}R^{21}R^{22}$; $R^8$ and $R^{14}$ are identical to or different from each other and represent a C1-C6 chain hydrocarbon group optionally substituted with one or more substituents selected from Group A.

[Embodiment 2] A present compound Z wherein $R^4$, $R^6$, and $R^9$ are identical to or different from each other and represent a hydrogen atom, or a methyl group; $R^5$ represents C1-C6 chain hydrocarbon group, a C3-C6 cycloalkyl group or a hydrogen atom; $R^7$ represents a C1-C6 chain hydrocarbon group, a C3-C6 cycloalkyl group, or $SiR^{20}R^{21}R^{22}$; $R^8$ and $R^{14}$ are identical to or different from each other and represent or a C1-C6 chain hydrocarbon group optionally substituted with one or more substituents selected from Group F, Group F: a group consisting of a phenyl group {the phenyl group may be optionally substituted with one or more substituents selected from the group consisting of C1-C6 chain hydrocarbon group and halogen atom}, a C3-C6 cycloalkyl group, and a halogen atom.

[Embodiment 3] The compound described in the Embodiment 2 wherein $R^4$, $R^6$ and $R^8$ each represents a methyl group.

[Embodiment 4] A present compound Z wherein E represents $R^4R^5C=C(R^6)—$, $R^7—C\equiv C—$, $R^{14}O—N=C(R^9)—$, $R^8R^9C=N—O—CH_2—$, a phenyl group, or a five- to six-membered aromatic heterocyclic group {the phenyl group and the five- to six-membered aromatic heterocyclic group each may be optionally substituted with one or more substituents selected from Group D}.

[Embodiment 5] The compound described in the Embodiment 1 wherein E represents $R^4R^5C=C(R^6)—$, $R^7—C\equiv C—$, $R^{14}O—N=C(R^9)—$, $R^8R^9C=N—O—CH_2—$, a phenyl group, or a five- to six-membered aromatic heterocyclic group {the phenyl group and the five- to six-membered aromatic heterocyclic group each may be optionally substituted with one or more substituents selected from Group D}.

[Embodiment 6] The compound described in the Embodiment 2 wherein E represents $R^4R^5C=C(R^6)—$, $R^7—C\equiv C—$, $R^{14}O—N=C(R^9)—$, $R^8R^9C=N—O—CH_2—$, a phenyl group or a five- to six-membered aromatic heterocyclic group {the phenyl group and the five- to six-membered aromatic heterocyclic group each may be optionally substituted with one or more substituents selected from Group D}.

[Embodiment 7] The compound described in the Embodiment 3 wherein E represents $R^4R^5C=C(R^6)—$, $R^7—C\equiv C—$, $R^{14}O—N=C(R^9)—$, $R^8R^9C=N—O—CH_2—$, a phenyl group or a five- to six-membered aromatic heterocyclic group {the phenyl group and the five- to six-membered aromatic heterocyclic group each may be optionally substituted with one or more substituents selected from Group D}.

[Embodiment 8] A present compound Z wherein E represents $R^7—C\equiv C—$, $R^{14}O—N=C(R^9)—$, a phenyl group, a thienyl group, a pyridyl group, or a pyrazolyl group {the phenyl group, the thienyl group, the pyridyl group and the pyrazolyl group each may be optionally substituted with one or more substituents selected from Group C}.

[Embodiment 9] The compound described in the Embodiment 8 wherein $R^9$ represents a hydrogen atom or a methyl group; $R^7$ represents a C1-C6 chain hydrocarbon group optionally substituted with one or more substituents selected from Group A, a C3-C6 cycloalkyl group optionally substituted with one or more substituents selected from Group B, a phenyl group optionally substituted with one or more substituents selected from Group C, or $SiR^{20}R^{21}R^{22}$, and $R^{14}$ represents a C1-C6 chain hydrocarbon group optionally substituted with one or more substituents selected from Group A.

[Embodiment 10] The compound described in the Embodiment 8 wherein $R^9$ represents a hydrogen atom or a methyl group; $R^7$ represents a C1-C6 chain hydrocarbon group, C3-C6 cycloalkyl group, or $SiR^{20}R^{21}R^{22}$; and $R^{14}$ represents a C1-C6 chain hydrocarbon group optionally substituted with one or more substituents selected from Group F.

[Embodiment 11] The compound described in the Embodiment 10 wherein $R^9$ represents a methyl group.

[Embodiment 12] A present compound Z wherein E represents $R^7—C\equiv C—$, $R^{14}O—N=C(R^9)—$, a phenyl group, or a pyridyl group {the phenyl group and the pyridyl group each may be optionally substituted with one or more substituents selected from Group C}.

[Embodiment 13] The compound described in the Embodiment 12 wherein $R^9$ represents a hydrogen atom or a methyl group; $R^7$ represents a C1-C6 chain hydrocarbon group optionally substituted with one or more substituents selected from Group A, a C3-C6 cycloalkyl group optionally substituted with one or more substituents selected from Group B, a phenyl group optionally substituted with one or more substituents selected from Group C, or $SiR^{20}R^{21}R^{22}$; and $R^{14}$ represents a C1-C6 chain hydrocarbon group optionally substituted with one or more substituents selected from Group A.

[Embodiment 14] The compound described in the Embodiment 12 wherein $R^9$ represents a hydrogen atom or a methyl group; $R^7$ represents a C1-C6 chain hydrocarbon group, C3-C6 cycloalkyl group, or $SiR^{20}R^{21}R^{22}$; and $R^{14}$ represents a C1-C6 chain hydrocarbon group optionally substituted with one or more substituents selected from Group F.

[Embodiment 15] The compound described in the Embodiment 14 wherein $R^9$ represents a methyl group.

[Embodiment 16] A present compound Z wherein E represents $R^7—C\equiv C—$.

[Embodiment 17] The compound described in the Embodiment 16 wherein $R^7$ represents a C1-C6 chain hydrocarbon group optionally substituted with one or more substituents selected from Group A, a C3-C6 cycloalkyl group optionally substituted with one or more substituents selected from Group B, a phenyl group optionally substituted with one or more substituents selected from Group C, or $SiR^{20}R^{21}R^{22}$.

[Embodiment 18] The compound described in the Embodiment 16 wherein $R^7$ represents a C1-C6 chain hydrocarbon group, a C3-C6 cycloalkyl group, or $SiR^{20}R^{21}R^{22}$.

[Embodiment 19] A present compound Z wherein Q represents a group represented by Q1, Q2, Q3 or Q4.

[Embodiment 20] The compound described in the Embodiment 1 wherein Q represent a group represented by Q1, Q2, Q3 or Q4.

[Embodiment 21] The compound described in the Embodiment 2 wherein Q represent a group represented by Q1, Q2, Q3 or Q4.

[Embodiment 22] The compound described in the Embodiment 3 wherein Q represent a group represented by Q1, Q2, Q3 or Q4.

[Embodiment 23] The compound described in the Embodiment 4 wherein Q represent a group represented by Q1, Q2, Q3 or Q4.

[Embodiment 24] The compound described in the Embodiment 5 wherein Q represent a group represented by Q1, Q2, Q3 or Q4.

[Embodiment 25] The compound described in the Embodiment 6 wherein Q represent a group represented by Q1, Q2, Q3 or Q4.

[Embodiment 26] The compound described in the Embodiment 7 wherein Q represent a group represented by Q1, Q2, Q3 or Q4.

[Embodiment 27] The compound described in the Embodiment 8 wherein Q represent a group represented by Q1, Q2, Q3 or Q4.

[Embodiment 28] The compound described in the Embodiment 9 wherein Q represent a group represented by Q1, Q2, Q3 or Q4.

[Embodiment 29] The compound described in the Embodiment 10 wherein Q represent a group represented by Q1, Q2, Q3 or Q4.

[Embodiment 30] The compound described in the Embodiment 11 wherein Q represent a group represented by Q1, Q2, Q3 or Q4.

[Embodiment 31] The compound described in the Embodiment 12 wherein Q represent a group represented by Q1, Q2, Q3 or Q4.

[Embodiment 32] The compound described in the Embodiment 13 wherein Q represent a group represented by Q1, Q2, Q3 or Q4.

[Embodiment 33] The compound described in the Embodiment 14 wherein Q represent a group represented by Q1, Q2, Q3 or Q4.

[Embodiment 34] The compound described in the Embodiment 15 wherein Q represent a group represented by Q1, Q2, Q3 or Q4.

[Embodiment 35] The compound described in the Embodiment 16 wherein Q represent a group represented by Q1, Q2, Q3 or Q4.

[Embodiment 36] The compound described in the Embodiment 17 wherein Q represent a group represented by Q1, Q2, Q3 or Q4.

[Embodiment 37] The compound described in the Embodiment 18 wherein Q represent a group represented by Q1, Q2, Q3 or Q4.

[Embodiment 38] A present compound Z wherein Q represents a group represented by Q1, Q2, or Q3; L represents $CH_2$ or an oxygen atom; and $R^3$ represents a difluoromethyl group or a methoxy group.

[Embodiment 39] The compound described in the Embodiment 1 wherein Q represents a group represented by Q1, Q2, or Q3; L represents $CH_2$ or an oxygen atom; and $R^3$ represents a difluoromethyl group or a methoxy group.

[Embodiment 40] The compound described in the Embodiment 2 wherein Q represents a group represented by Q1, Q2, or Q3; L represents $CH_2$ or an oxygen atom; and $R^3$ represents a difluoromethyl group or a methoxy group.

[Embodiment 41] The compound described in the Embodiment 3 wherein Q represents a group represented by Q1, Q2, or Q3; L represents $CH_2$ or an oxygen atom; and $R^3$ represents a difluoromethyl group or a methoxy group.

[Embodiment 42] The compound described in the Embodiment 4 wherein Q represents a group represented by Q1, Q2, or Q3; L represents $CH_2$ or an oxygen atom; and $R^3$ represents a difluoromethyl group or a methoxy group.

[Embodiment 43] The compound described in the Embodiment 5 wherein Q represents a group represented by Q1, Q2, or Q3; L represents $CH_2$ or an oxygen atom; and $R^3$ represents a difluoromethyl group or a methoxy group.

[Embodiment 44] The compound described in the Embodiment 6 wherein Q represents a group represented by Q1, Q2, or Q3; L represents $CH_2$ or an oxygen atom; and $R^3$ represents a difluoromethyl group or a methoxy group.

[Embodiment 45] The compound described in the Embodiment 7 wherein Q represents a group represented by Q1, Q2, or Q3; L represents $CH_2$ or an oxygen atom; and $R^3$ represents a difluoromethyl group or a methoxy group.

[Embodiment 46] The compound described in the Embodiment 8 wherein Q represents a group represented by Q1, Q2, or Q3; L represents $CH_2$ or an oxygen atom; and $R^3$ represents a difluoromethyl group or a methoxy group.

[Embodiment 47] The compound described in the Embodiment 9 wherein Q represents a group represented by Q1, Q2, or Q3; L represents $CH_2$ or an oxygen atom; and $R^3$ represents a difluoromethyl group or a methoxy group.

[Embodiment 48] The compound described in the Embodiment 10 wherein Q represents a group represented by Q1, Q2, or Q3; L represents $CH_2$ or an oxygen atom; and $R^3$ represents a difluoromethyl group or a methoxy group.

[Embodiment 49] The compound described in the Embodiment 11 wherein Q represents a group represented by Q1, Q2, or Q3; L represents $CH_2$ or an oxygen atom; and $R^3$ represents a difluoromethyl group or a methoxy group.

[Embodiment 50] The compound described in the Embodiment 12 wherein Q represents a group represented by Q1, Q2, or Q3; L represents $CH_2$ or an oxygen atom; and $R^3$ represents a difluoromethyl group or a methoxy group.

[Embodiment 51] The compound described in the Embodiment 13 wherein Q represents a group represented by Q1, Q2, or Q3; L represents $CH_2$ or an oxygen atom; and $R^3$ represents a difluoromethyl group or a methoxy group.

[Embodiment 52] The compound described in the Embodiment 14 wherein Q represents a group represented by Q1, Q2, or Q3; L represents $CH_2$ or an oxygen atom; and $R^3$ represents a difluoromethyl group or a methoxy group.

[Embodiment 53] The compound described in the Embodiment 15 wherein Q represents a group represented by Q1, Q2, or Q3; L represents $CH_2$ or an oxygen atom; and $R^3$ represents a difluoromethyl group or a methoxy group.

[Embodiment 54] The compound described in the Embodiment 16 wherein Q represents a group represented by Q1, Q2, or Q3; L represents $CH_2$ or an oxygen atom; and $R^3$ represents a difluoromethyl group or a methoxy group.

[Embodiment 55] The compound described in the Embodiment 17 wherein Q represents a group represented by Q1, Q2, or Q3; L represents $CH_2$ or an oxygen atom; and $R^3$ represents a difluoromethyl group or a methoxy group.

[Embodiment 56] The compound described in the Embodiment 18 wherein Q represents a group represented by Q1, Q2, or Q3; L represents $CH_2$ or an oxygen atom; and $R^3$ represents a difluoromethyl group or a methoxy group.

[Embodiment 57] The compound described in the Embodiment 38 wherein L represents an oxygen atom.

[Embodiment 58] The compound described in the Embodiment 39 wherein L represents an oxygen atom.

[Embodiment 59] The compound described in the Embodiment 40 wherein L represents an oxygen atom.

[Embodiment 60] The compound described in the Embodiment 41 wherein L represents an oxygen atom.

[Embodiment 61] The compound described in the Embodiment 42 wherein L represents an oxygen atom.

[Embodiment 62] The compound described in the Embodiment 43 wherein L represents an oxygen atom.

[Embodiment 63] The compound described in the Embodiment 44 wherein L represents an oxygen atom.

[Embodiment 64] The compound described in the Embodiment 45 wherein L represents an oxygen atom.

[Embodiment 65] The compound described in the Embodiment 46 wherein L represents an oxygen atom.

[Embodiment 66] The compound described in the Embodiment 47 wherein L represents an oxygen atom.

[Embodiment 67] The compound described in the Embodiment 48 wherein L represents an oxygen atom.

[Embodiment 68] The compound described in the Embodiment 49 wherein L represents an oxygen atom.

[Embodiment 69] The compound described in the Embodiment 50 wherein L represents an oxygen atom.

[Embodiment 70] The compound described in the Embodiment 51 wherein L represents an oxygen atom.

[Embodiment 71] The compound described in the Embodiment 52 wherein L represents an oxygen atom.

[Embodiment 72] The compound described in the Embodiment 53 wherein L represents an oxygen atom.

[Embodiment 73] The compound described in the Embodiment 54 wherein L represents an oxygen atom.

[Embodiment 74] The compound described in the Embodiment 55 wherein L represents an oxygen atom.

[Embodiment 75] The compound described in the Embodiment 56 wherein L represents an oxygen atom.

[Embodiment 76] A present compound Z wherein n is 0.

[Embodiment 77] The compound described in the Embodiment 1 wherein n is 0.

[Embodiment 78] The compound described in the Embodiment 2 wherein n is 0.

[Embodiment 79] The compound described in the Embodiment 3 wherein n is 0.

[Embodiment 80] The compound described in the Embodiment 4 wherein n is 0.

[Embodiment 81] The compound described in the Embodiment 5 wherein n is 0.

[Embodiment 82] The compound described in the Embodiment 6 wherein n is 0.

[Embodiment 83] The compound described in the Embodiment 7 wherein n is 0.

[Embodiment 84] The compound described in the Embodiment 8 wherein n is 0.

[Embodiment 85] The compound described in the Embodiment 9 wherein n is 0.

[Embodiment 86] The compound described in the Embodiment 10 wherein n is 0.

[Embodiment 87] The compound described in the Embodiment 11 wherein n is 0.

[Embodiment 88] The compound described in the Embodiment 12 wherein n is 0.

[Embodiment 89] The compound described in the Embodiment 13 wherein n is 0.

[Embodiment 90] The compound described in the Embodiment 14 wherein n is 0.

[Embodiment 91] The compound described in the Embodiment 15 wherein n is 0.

[Embodiment 92] The compound described in the Embodiment 16 wherein n is 0.

[Embodiment 93] The compound described in the Embodiment 17 wherein n is 0.

[Embodiment 94] The compound described in the Embodiment 18 wherein n is 0.

[Embodiment 95] The compound described in the Embodiment 19 wherein n is 0.

[Embodiment 96] The compound described in the Embodiment 20 wherein n is 0.

[Embodiment 97] The compound described in the Embodiment 21 wherein n is 0.

[Embodiment 98] The compound described in the Embodiment 22 wherein n is 0.

[Embodiment 99] The compound described in the Embodiment 23 wherein n is 0.

[Embodiment 100] The compound described in the Embodiment 24 wherein n is 0.

[Embodiment 101] The compound described in the Embodiment 25 wherein n is 0.

[Embodiment 102] The compound described in the Embodiment 26 wherein n is 0.

[Embodiment 103] The compound described in the Embodiment 27 wherein n is 0.

[Embodiment 104] The compound described in the Embodiment 28 wherein n is 0.

[Embodiment 105] The compound described in the Embodiment 29 wherein n is 0.

[Embodiment 106] The compound described in the Embodiment 30 wherein n is 0.

[Embodiment 107] The compound described in the Embodiment 31 wherein n is 0.

[Embodiment 108] The compound described in the Embodiment 32 wherein n is 0.

[Embodiment 109] The compound described in the Embodiment 33 wherein n is 0.

[Embodiment 110] The compound described in the Embodiment 34 wherein n is 0.

[Embodiment 111] The compound described in the Embodiment 35 wherein n is 0.

[Embodiment 112] The compound described in the Embodiment 36 wherein n is 0.

[Embodiment 113] The compound described in the Embodiment 37 wherein n is 0.

[Embodiment 114] The compound described in the Embodiment 38 wherein n is 0.

[Embodiment 115] The compound described in the Embodiment 39 wherein n is 0.

[Embodiment 116] The compound described in the Embodiment 40 wherein n is 0.

[Embodiment 117] The compound described in the Embodiment 41 wherein n is 0.

[Embodiment 118] The compound described in the Embodiment 42 wherein n is 0.

[Embodiment 119] The compound described in the Embodiment 43 wherein n is 0.

[Embodiment 120] The compound described in the Embodiment 44 wherein n is 0.
[Embodiment 121] The compound described in the Embodiment 45 wherein n is 0.
[Embodiment 122] The compound described in the Embodiment 46 wherein n is 0.
[Embodiment 123] The compound described in the Embodiment 47 wherein n is 0.
[Embodiment 124] The compound described in the Embodiment 48 wherein n is 0.
[Embodiment 125] The compound described in the Embodiment 49 wherein n is 0.
[Embodiment 126] The compound described in the Embodiment 50 wherein n is 0.
[Embodiment 127] The compound described in the Embodiment 51 wherein n is 0.
[Embodiment 128] The compound described in the Embodiment 52 wherein n is 0.
[Embodiment 129] The compound described in the Embodiment 53 wherein n is 0.
[Embodiment 130] The compound described in the Embodiment 54 wherein n is 0.
[Embodiment 131] The compound described in the Embodiment 55 wherein n is 0.
[Embodiment 132] The compound described in the Embodiment 56 wherein n is 0.
[Embodiment 133] The compound described in the Embodiment 57 wherein n is 0.
[Embodiment 134] The compound described in the Embodiment 58 wherein n is 0.
[Embodiment 135] The compound described in the Embodiment 59 wherein n is 0.
[Embodiment 136] The compound described in the Embodiment 60 wherein n is 0.
[Embodiment 137] The compound described in the Embodiment 61 wherein n is 0.
[Embodiment 138] The compound described in the Embodiment 62 wherein n is 0.
[Embodiment 139] The compound described in the Embodiment 63 wherein n is 0.
[Embodiment 140] The compound described in the Embodiment 64 wherein n is 0.
[Embodiment 141] The compound described in the Embodiment 65 wherein n is 0.
[Embodiment 142] The compound described in the Embodiment 66 wherein n is 0.
[Embodiment 143] The compound described in the Embodiment 67 wherein n is 0.
[Embodiment 144] The compound described in the Embodiment 68 wherein n is 0.
[Embodiment 145] The compound described in the Embodiment 69 wherein n is 0.
[Embodiment 146] The compound described in the Embodiment 70 wherein n is 0.
[Embodiment 147] The compound described in the Embodiment 71 wherein n is 0.
[Embodiment 148] The compound described in the Embodiment 72 wherein n is 0.
[Embodiment 148] The compound described in the Embodiment 72 wherein n is 0.
[Embodiment 149] The compound described in the Embodiment 73 wherein n is 0.
[Embodiment 150] The compound described in the Embodiment 74 wherein n is 0.
[Embodiment 151] The compound described in the Embodiment 75 wherein n is 0.
[Embodiment 152] A present compound Z or the compound described in any one of the Embodiment 1 to the Embodiment 151 wherein $R^1$ represents a methyl group, a chlorine atom, or a hydrogen atom.
[Embodiment 153] A present compound Z or the compound described in any one of the Embodiment 1 to the Embodiment 151 wherein $R^1$ represents a methyl group or a chlorine atom.
[Embodiment 154] A present compound Z or the compound described in any one of the Embodiment 1 to the Embodiment 151 wherein $R^1$ represents a methyl group.
[Embodiment 155] A present compound Z or the compound described in any one of the Embodiment 1 to the Embodiment 18 wherein Q represents Q1, n is 0, and $R^1$ represents a methyl group.
[Embodiment 156] A present compound Z or the compound described in any one of the Embodiment 1 to the Embodiment 18 wherein Q represents Q1, L represents $CH_2$ or an oxygen atom, n is 0, and $R^1$ represents a methyl group.
[Embodiment 157] A present compound Z or the compound described in any one of the Embodiment 1 to the Embodiment 18 wherein Q represents Q1, L represents an oxygen atom, n is 0, and $R^1$ represents a methyl group.
[Embodiment 158] A present compound Z or the compound described in any one of the Embodiment 1 to the Embodiment 18 wherein Q represents Q1, L represents $CH_2$, n is 0, and $R^1$ represents a methyl group.
[Embodiment 159] A present compound Z or the compound described in any one of the Embodiment 1 to the Embodiment 18 wherein Q represents Q2, n is 0, and $R^1$ represents a methyl group.
[Embodiment 160] A present compound Z or the compound described in any one of the Embodiment 1 to the Embodiment 18 wherein Q represents Q2, X represents an oxygen atom, n is 0, and $R^1$ represents a methyl group.
[Embodiment 161] A present compound Z or the compound described in any one of the Embodiment 1 to the Embodiment 18 wherein Q represents Q2, X represents NH, n is 0, and $R^1$ represents a methyl group.
[Embodiment 162] A present compound Z or the compound described in any one of the Embodiment 1 to the Embodiment 18 wherein Q represents Q3, n is 0, and $R^1$ represents a methyl group.
[Embodiment 163] A present compound Z or the compound described in any one of the Embodiment 1 to the Embodiment 18 wherein Q represents Q3, $R^3$ represents a difluoromethyl group or a methoxy group, n is 0, and $R^1$ represents a methyl group.
[Embodiment 164] A present compound Z or the compound described in any one of the Embodiment 1 to the Embodiment 18 wherein Q represents Q3, $R^3$ represents a difluoromethyl group, n is 0, and $R^1$ represents a methyl group.
[Embodiment 165] A present compound Z or the compound described in any one of the Embodiment 1 to the Embodiment 18 wherein Q represents Q3, $R^3$ represents a methoxy group, n is 0, and $R^1$ represents a methyl group.

Embodiments of the compound Z of the present invention include the following compounds.

[Embodiment 166] A compound Z of the present invention wherein $R^4$ and $R^6$ are identical to or different from each other and represent a C1-C3 chain hydrocarbon group or a hydrogen atom, $R^5$ represents a C1-C6 chain hydrocarbon group optionally substituted with one or more substituents selected from Group A, a C3-C6 cycloalkyl group optionally substituted with one or more substituents selected from Group B, or a hydrogen atom, and $R^{7A}$ represents a cyclopropyl group.

[Embodiment 167] A compound Z of the present invention wherein $R^4$ and $R^6$ are identical to or different from each other and represent a methyl group or a hydrogen atom, $R^5$ represents a C1-C6 chain hydrocarbon group, a C3-C6 cycloalkyl group, or a hydrogen atom, and $R^{7A}$ represents a cyclopropyl group.

[Embodiment 168] A compound Z of the present invention wherein $E^A$ represents $R^4R^5C=C(R^6)-$.

[Embodiment 169] The compound described in the Embodiment 168 wherein $R^4$ and $R^6$ are identical to or different from each other and represent a C1-C3 chain hydrocarbon group or a hydrogen atom, $R^5$ represents a C1-C6 chain hydrocarbon group optionally substituted with one or more substituents selected from Group A, a C3-C6 cycloalkyl group optionally substituted with one or more substituents selected from Group B, or a hydrogen atom.

[Embodiment 170] The compound described in the Embodiment 168 wherein $R^4$ and $R^6$ represents are identical to or different from each other and represent a methyl group or a hydrogen atom, and $R^5$ represents a C1-C6 chain hydrocarbon group, C3-C6 cycloalkyl group or a hydrogen atom.

[Embodiment 171] A compound Z of the present invention wherein $E^A$ represents $R^{7A}-C\equiv C-$.

[Embodiment 172] The compound described in the Embodiment 171 wherein $R^{7A}$ represents a cyclopropyl group.

[Embodiment 173] A compound Z of the present invention wherein $E^A$ represents a 1-pyrazolyl group optionally substituted with one or more substituents selected from Group E.

[Embodiment 174] The compound described in the Embodiment 173 wherein $E^A$ represents a 1-pyrazolyl group optionally substituted with one or more C1-C3 chain hydrocarbon group {the C1-C3 chain hydrocarbon group may be optionally substituted with one or more halogen atoms}.

[Embodiment 175] A compound Z of the present invention wherein n is 0.

[Embodiment 176] The compound described in the Embodiment 166 wherein n is 0.

[Embodiment 177] The compound described in the Embodiment 167 wherein n is 0.

[Embodiment 178] The compound described in the Embodiment 168 wherein n is 0.

[Embodiment 179] The compound described in the Embodiment 169 wherein n is 0.

[Embodiment 180] The compound described in the Embodiment 170 wherein n is 0.

[Embodiment 181] The compound described in the Embodiment 171 wherein n is 0.

[Embodiment 182] The compound described in the Embodiment 172 wherein n is 0.

[Embodiment 183] The compound described in the Embodiment 173 wherein n is 0.

[Embodiment 184] The compound described in the Embodiment 174 wherein n is 0.

[Embodiment 185] A compound Z of the present invention wherein L represents $CH_2$ or an oxygen atom.

[Embodiment 186] The compound described in the Embodiment 166 wherein L represents $CH_2$ or an oxygen atom.

[Embodiment 187] The compound described in the Embodiment 167 wherein L represents $CH_2$ or an oxygen atom.

[Embodiment 188] The compound described in the Embodiment 168 wherein L represents $CH_2$ or an oxygen atom.

[Embodiment 189] The compound described in the Embodiment 169 wherein L represents $CH_2$ or an oxygen atom.

[Embodiment 190] The compound described in the Embodiment 170 wherein L represents $CH_2$ or an oxygen atom.

[Embodiment 191] The compound described in the Embodiment 171 wherein L represents $CH_2$ or an oxygen atom.

[Embodiment 192] The compound described in the Embodiment 172 wherein L represents $CH_2$ or an oxygen atom.

[Embodiment 193] The compound described in the Embodiment 173 wherein L represents $CH_2$ or an oxygen atom.

[Embodiment 194] The compound described in the Embodiment 174 wherein L represents $CH_2$ or an oxygen atom.

[Embodiment 195] The compound described in the Embodiment 175 wherein L represents $CH_2$ or an oxygen atom.

[Embodiment 196] The compound described in the Embodiment 176 wherein L represents $CH_2$ or an oxygen atom.

[Embodiment 197] The compound described in the Embodiment 177 wherein L represents $CH_2$ or an oxygen atom.

[Embodiment 198] The compound described in the Embodiment 178 wherein L represents $CH_2$ or an oxygen atom.

[Embodiment 199] The compound described in the Embodiment 179 wherein L represents $CH_2$ or an oxygen atom.

[Embodiment 200] The compound described in the Embodiment 180 wherein L represents $CH_2$ or an oxygen atom.

[Embodiment 201] The compound described in the Embodiment 181 wherein L represents $CH_2$ or an oxygen atom.

[Embodiment 202] The compound described in the Embodiment 182 wherein L represents $CH_2$ or an oxygen atom.

[Embodiment 203] The compound described in the Embodiment 183 wherein L represents $CH_2$ or an oxygen atom.

[Embodiment 204] The compound described in the Embodiment 184 wherein L represents $CH_2$ or an oxygen atom.

[Embodiment 205] A compound Z of the present invention wherein L represents an oxygen atom.

[Embodiment 206] The compound described in the Embodiment 166 wherein L represents an oxygen atom.

[Embodiment 207] The compound described in the Embodiment 167 wherein L represents an oxygen atom.

[Embodiment 208] The compound described in the Embodiment 168 wherein L represents an oxygen atom.
[Embodiment 209] The compound described in the Embodiment 169 wherein L represents an oxygen atom.
[Embodiment 210] The compound described in the Embodiment 170 wherein L represents an oxygen atom.
[Embodiment 211] The compound described in the Embodiment 171 wherein L represents an oxygen atom.
[Embodiment 212] The compound described in the Embodiment 172 wherein L represents an oxygen atom.
[Embodiment 213] The compound described in the Embodiment 173 wherein L represents an oxygen atom.
[Embodiment 214] The compound described in the Embodiment 174 wherein L represents an oxygen atom.
[Embodiment 215] The compound described in the Embodiment 175 wherein L represents an oxygen atom.
[Embodiment 216] The compound described in the Embodiment 176 wherein L represents an oxygen atom.
[Embodiment 217] The compound described in the Embodiment 177 wherein L represents an oxygen atom.
[Embodiment 218] The compound described in the Embodiment 178 wherein L represents an oxygen atom.
[Embodiment 219] The compound described in the Embodiment 179 wherein L represents an oxygen atom.
[Embodiment 220] The compound described in the Embodiment 180 wherein L represents an oxygen atom.
[Embodiment 221] The compound described in the Embodiment 181 wherein L represents an oxygen atom.
[Embodiment 222] The compound described in the Embodiment 182 wherein L represents an oxygen atom.
[Embodiment 223] The compound described in the Embodiment 183 wherein L represents an oxygen atom.
[Embodiment 224] The compound described in the Embodiment 184 wherein L represents an oxygen atom.
[Embodiment 225] A compound Z of the present invention or the compound described in any one of the Embodiment 166 to the Embodiment 224 wherein $R^1$ represents a methyl group, a chlorine atom or a hydrogen atom.
[Embodiment 226] A compound Z of the present invention or the compound described in any one of the Embodiment 166 to the Embodiment 224 wherein $R^1$ represents a methyl group or a chlorine atom.

Next, the process for preparing the present compound and the compound of the present invention are explained.

The present compound can be prepared according to the methods described in WO 2000/041999 A1, WO 1996/032399 A1, WO 2000/007999 A1, WO 1998/003464 A1, WO 2001/042227 A1, WO 2001/000562 A1, EP 212859 B2, WO 2000/018727 A1, WO 1998/043949 and the like. The present compound can be prepared also by the below-described processes and the like.

Process A

A compound represented by formula (A1) (hereinafter, referred to as Compound (A1)) can be prepared by reacting a compound represented by formula (B1) (hereinafter, referred to as Compound (B1)) with a compound represented by formula (M1) (hereinafter, referred to as Compound (M1)) in the presence of a palladium catalyst and a base.

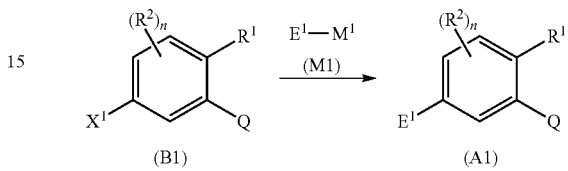

[wherein, $E^1$ represents $R^4R^5C\!=\!C(R^6)\!-\!$, a C6-C10 aryl group, or a five- to ten-aromatic heterocyclic group {the C6-C10 aryl group, and the five- to ten-aromatic heterocyclic group each may be optionally substituted with one or more substituents selected from Group D}; $M^1$ represents $B(OH)_2$, or 4,4,5,5-tetramethyl-1,3,2-dioxaborolan-2-yl group; $X^1$ represents a leaving group such as chlorine atom, bromine atom, iodine atom, or triflyloxy group; and the other symbols are the same as defined above.]

The reaction is usually carried out in a solvent. Examples of the solvent to be used in the reaction include hydrocarbons such as hexane, toluene, and xylene (hereinafter, collectively referred to as hydrocarbons); ethers such as methyl tert-butyl ether (hereinafter, referred to as MTBE), tetrahydrofuran (hereinafter, referred to as THF), dimethoxyethane (hereinafter, collectively referred to as ethers); halogenated hydrocarbons such as chloroform and chlorobenzene (hereinafter, collectively referred to as halogenated hydrocarbons); amides such as dimethylformamide (hereinafter, referred to as DMF) and N-methyl pyrrolidone (hereinafter, collectively referred to as amides); esters such as methyl acetate and ethyl acetate (hereinafter, collectively referred to as esters); nitriles such as acetonitrile and propionitrile (hereinafter, collectively referred to as nitriles); water; and mixed solvents thereof.

Example of the palladium catalysts includes [1,1'-bis(diphenylphoshino)ferrocene]dichloropalladium (II) dichloromethane adduct.

Examples of the base include organic bases such as triethylamine and pyridine (hereinafter, collectively referred to as organic bases); alkali metal carbonates such as sodium carbonates and potassium carbonates (hereinafter, collectively referred to as alkali metal carbonates); alkali metal hydrocarbonates such as sodium hydrocarbonate and potassium hydrocarbonate (hereinafter, collectively referred to as alkali metal hydrocarbonates); sodium fluoride, and tripotassium phosphate.

In the reaction, the compound (M1) is usually used within a range of 1 to 10 molar ratio(s), the palladium catalyst is usually used within a range of 0.01 to 1 molar ratio(s), and the base is usually used within a range of 1 to 10 molar ratio(s), as opposed to 1 mole of the compound (B1).

The reaction temperature is usually in a range of 0 to 150° C. The reaction period of the reaction is usually within a range of 0.1 to 120 hours.

When the reaction is completed, the reaction mixtures are worked up (such as concentration and drying) to isolate the compound (A1).

The compound (B1) and the compound (M1) are known compounds, or can be prepared according to a known method.

Process B

A compound represented by formula (A2) (hereinafter, referred to as Compound (A2)) can be prepared by reacting the compound (B1) with a compound represented by formula (M2) (hereinafter, referred to as Compound (M2)) in the presence of a metal catalyst and a base.

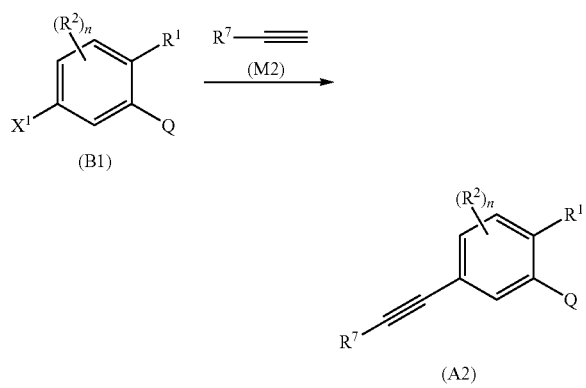

[wherein the symbols are the same as defined above.]

The reaction is usually carried out in a solvent. Examples of the solvents to be used in the reaction include hydrocarbons, ethers, halogenated hydrocarbons, amides, esters, nitriles, and mixed solvents thereof.

Examples of the metal catalyst include bis(triphenylphosphine)palladium(II) dichloride (hereinafter, referred to as $PdCl_2(PPh_3)_2$) and copper iodide (I).

Examples of the bases to be used in the reaction include organic bases.

In the reaction, the compound (M2) is usually used within a range of 1 to 10 molar ratio(s), the metal catalyst is usually used within a range of 0.01 to 1 molar ratio(s), and the base is usually used within a range of 1 to 10 molar ratio(s), as opposed to 1 mole of the compound (B1).

The reaction temperature of the reaction is usually within a range of 0 to 150° C. The reaction period of the reaction is usually within a range of 0.1 to 120 hours.

When the reaction is completed, the reaction mixtures are worked up (such as concentration and drying) to isolate the compound (A2).

The compound (B1) and the compound (M2) are known compounds, or can be prepared according to a known method.

Process C

A compound represented by formula (A3) (hereinafter, referred to as Compound (A3)) can be prepared by reacting a compound represented by formula (B2) (hereinafter, referred to as Compound (B2)) with a compound represented by formula (M3)) (hereinafter, referred to as Compound (M3)) or salts thereof.

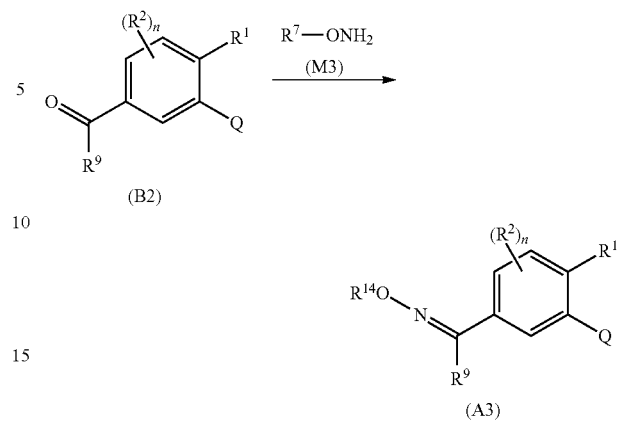

[wherein the symbols are the same as defined above.]

Examples of the salts of the compound (M3) include hydrochloride salts and sulfates thereof.

The reaction can be conducted according to a method described in WO 1998/043949, WO 2000/041999, WO 2000/007999 and the like.

The compound (B2) and the compound (M3) are known compounds, or can be prepared according to a known method.

Process D

A compound represented by formula (A4) (hereinafter, referred to as Compound (A4)) can be prepared by reacting a compound represented by formula (B3) (hereinafter, referred to as Compound (B3)) with a compound represented by formula (M4) (hereinafter, referred to as Compound (M4)) in the presence of a base.

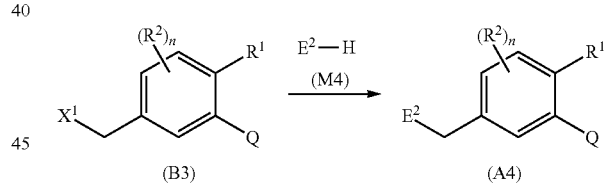

[wherein, $E^2$ represents $R^8R^9C=N-O-$, $R^8O-N=C(R^9)-C(R^{10})=N-O-$, $R^8C(O)-C(R^9)=N-O-$, or $R^8C(=N-O-R^9)-C(R^{10})=N-O-$, and the other symbols are the same as defined above.]

The reaction can be conducted according to a method described in WO 1990/07493 A1, WO 1995/18789 A1 and the like.

The compound (B3) and the compound (M4) are known compounds, or can be prepared according to a known method.

Process E

A compound represented by formula (A5) (hereinafter, referred to as Compound (A5)) can be prepared by reacting a compound represented by formula (B4) (hereinafter, referred to as Compound (B4)) with a compound represented by formula (M5) (hereinafter, referred to as Compound (M5)) in the presence of a base.

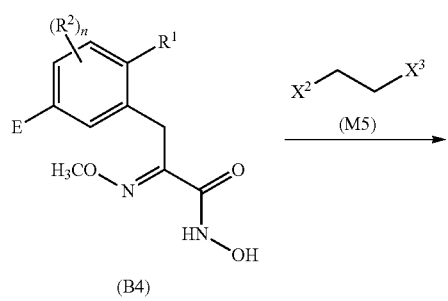

(B4)

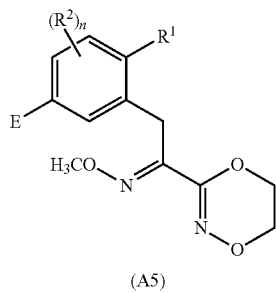

(A5)

[wherein $X^2$ and $X^3$ are identical to or different from each other and represent a chlorine atom, a bromine atom, or an iodine atom, and the other symbols are the same as defined above.]

The reaction can be conducted according to a method described in WO 2017/005725.

The compound (M5) is a known compound, or can be prepared according to a known method.

Next, the process for preparing an intermediate compound for the present compound is explained.

Process F

A compound represented by formula (F1-1) (hereinafter, referred to as Compound (F1-1)) can be prepared by reacting a compound represented by formula (E1-1) (hereinafter, referred to as Compound (E1-1)) with iodomethane in the presence of a base.

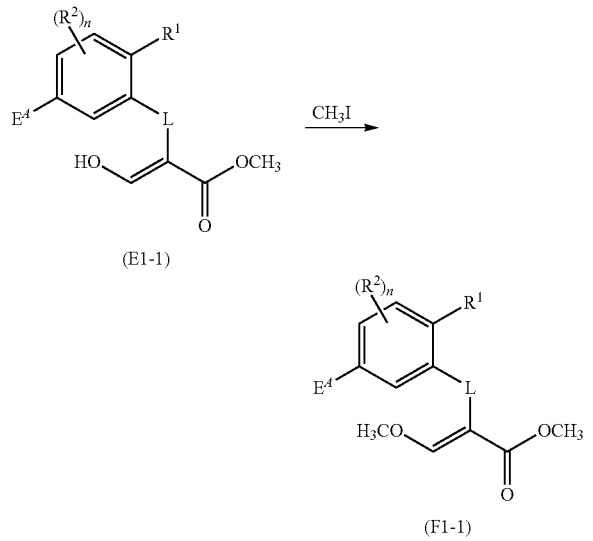

[wherein the symbols are the same as defined above.]

The reaction is usually carried out in a solvent. Examples of the solvent to be used in the reaction include hydrocarbons, ethers, halogenated hydrocarbons, amides, esters, sulfoxides such as dimethyl sulfoxide (hereinafter, referred to as DMSO) (hereinafter, collectively referred to as sulfoxides), nitriles, and mixed solvents thereof.

Examples of the base to be used in the reaction includes organic bases, sodium carbonates, alkali metal carbonates, alkali metal hydrocarbonates, sodium hydride, and mixtures thereof.

In the reaction, iodomethane is usually used within a range of 1 to 10 molar ratio(s), and the base is usually used within a range of 1 to 20 molar ratio(s), as opposed to 1 mole of the compound (E1-1).

The reaction temperature is usually within a range of $-20$ to $150°$ C. The reaction period of the reaction is usually within a range of 0.1 to 120 hours.

When the reaction is completed, water is added to the reaction mixtures, and the reaction mixtures are extracted with organic solvent(s), and the organic layers are worked up (such as drying and concentration) to isolate the compound (F1-1).

Reference Process A

A compound represented by formula (B1-1) (hereinafter, referred to as Compound (B1-1)) can be prepared by reacting a compound represented by formula (C1-1) (hereinafter, referred to as Compound (C1-1)) with iodomethane in the presence of a base.

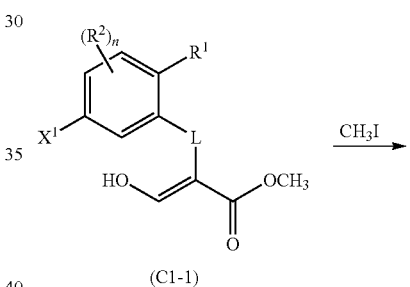

[wherein the symbols are the same as defined above.]

The reaction can be conducted by using the compound (C1-1) in the place of the compound (E1-1) according to the process F.

Reference Process B

The compound (C1-1) can be prepared by reacting a compound represented by formula (D1-1) (hereinafter, referred to as Compound (D1-1)) with methyl formate in the presence of a base.

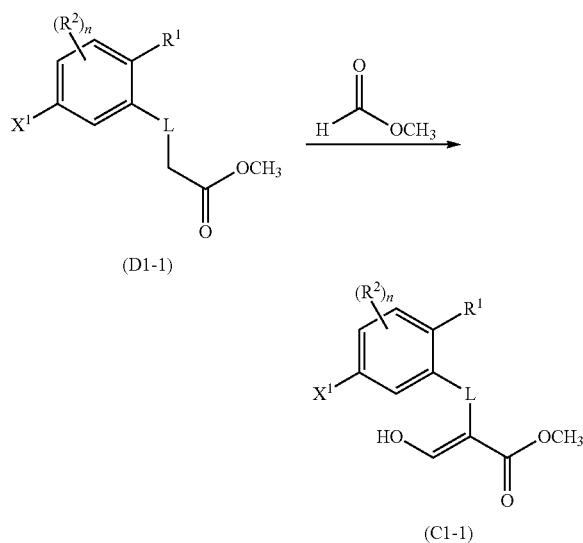

(D1-1)

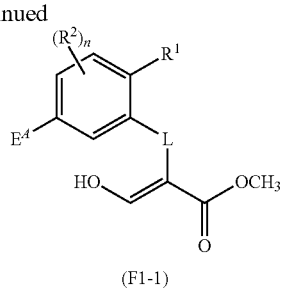

(C1-1)

[wherein the symbols are the same as defined above.]

The reaction is usually carried out in a solvent. Examples of the solvents to be used in the reaction include hydrocarbons, ethers, halogenated hydrocarbons, amides, sulfoxides, nitriles, and mixed solvents thereof.

Examples of the base to be used in the reaction include inorganic bases such as sodium hydride and potassium hydride; alkali metal alkoxides such as sodium methoxide, sodium ethoxide, and potassium t-butoxide; alkali metal amides such as sodium amide, lithium amide, lithium diisopropylamide, sodium hexamethyldisilazide, lithium hexamethyldisilazide; and mixtures thereof.

In the reaction, methyl formate is usually used within a range of 1 to 100 molar ratio(s), and the base is usually used within a range of 1 to 10 molar ratio(s), as opposed to 1 mole of the compound (D1-1).

The reaction temperature is usually within a range of −20 to 80° C. The reaction period of the reaction is usually within a range of 0.1 to 120 hours.

When the reaction is completed, acidic aqueous solution such as dilute hydrochloric acid is added to the reaction mixtures, and the reaction mixtures are extracted with organic solvent(s), and the organic layers are worked up (such as drying and concentration) to isolate the compound (C1-1).

Reference Process C

The compound (F1-1) can be prepared by reacting a compound represented by formula (G1-1) (hereinafter, referred to as Compound (G1-1)) with methyl formate in the presence of a base.

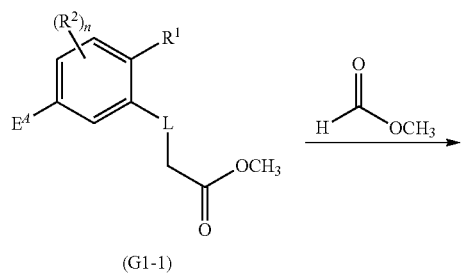

(G1-1)

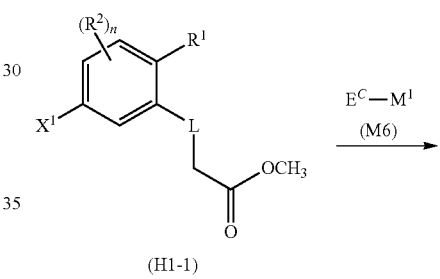

(F1-1)

[wherein the symbols are the same as defined above.]

The reaction can be conducted by using the compound (G1-1) in the place of the compound (D1-1) according to the reference process B.

Reference Process D

A compound represented by formula (G1-2) can be prepared by reacting a compound represented by formula (H1-1) (hereinafter, referred to as Compound (H1-1)) with a compound represented by formula (M6) (hereinafter, referred to as Compound (M6)) in the presence of a palladium catalyst and a base.

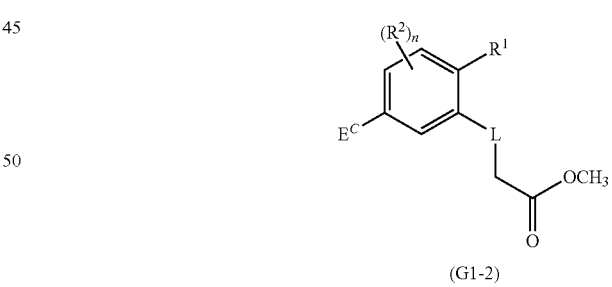

(H1-1)

(G1-2)

[wherein $E^c$ represents $R^4R^5C{=}C(R^6)-$, and the other symbols are the same as defined above.]

The reaction can be conducted by using the compound (H1-1) in the place of the compound (B1) according to the process A.

Reference Process E

The compound (G1-3) can be prepared by reacting the compound (H1-1) with a compound represented by formula (M7) (hereinafter, referred to as Compound (M7)) in the presence of a metal catalyst and a base.

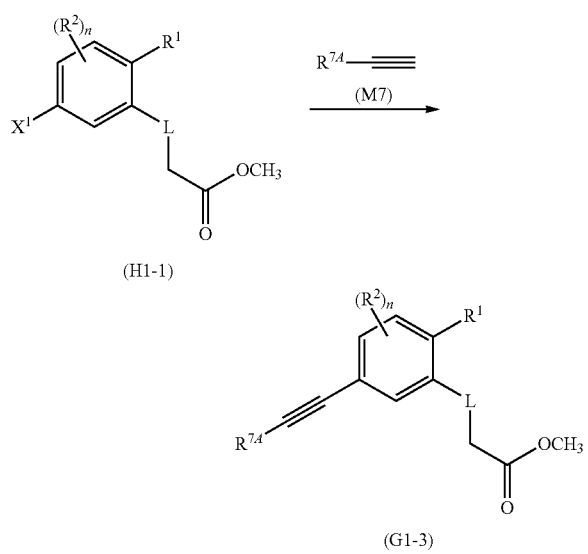

(H1-1)

(G1-3)

[wherein the symbols are the same as defined above.]

The reaction can be conducted by using the compound (H1-1) in the place of the compound (B1) according to the process B.

Reference Process F

The compound (B4) can be prepared by reacting a compound represented by formula (A6) with hydroxylamine or salts thereof in the presence of a base.

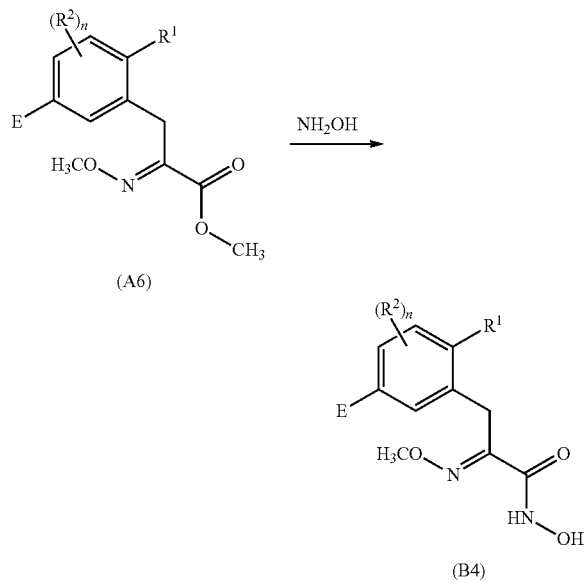

(A6)

(B4)

[wherein the symbols are the same as defined above.]

Examples of hydroxylamine include hydrochloric acid salts or sulfate salts thereof.

The reaction can be conducted, for example, according to a method described in WO 2009/036020 or Org. Biomol. Chem., 2016, 14, 9046-9054.

The compound of the present invention may be mixed or combined with one or more ingredients selected from a group consisting of the following Group (a), Group (b), Group (c), and Group (d), (hereinafter, referred to as "Present ingredient").

The above-mentioned mixing or combining represents a use of the compound of the present invention and the Present ingredient at same time, separately or at certain intervals.

When the compound of the present invention and the present ingredient are used at the same time, the compound of the present invention and the Present ingredient may be contained in separate formulations respectively, or may be contained in the same one formulation.

One aspect of the present invention is a composition comprising one or more ingredients selected from Group (a), Group (b), Group (c) and Group (d) as well as the compound of the present invention (hereinafter, referred to as Composition A).

Group (a) is a group consisting of each active ingredient as Acetylcholinesterase inhibitors (for example, carbamate insecticides, or organophosphorus insecticides), GABA-gated chloride channel blockers (for example, phenylpyrazole insecticides), Sodium channel modulators (for example, pyrethroid insecticides), Nicotinic acetylcholine receptor competitive modulators (for example, neonicotinoid insecticides), Nicotinic acetylcholine receptor allosteric modulators, Glutamatergic chlorine ion channel allosteric modulators (for example, macrolide insecticides), Juvenile hormone mimic, Multisite inhibitors, chordotonal organ TRPV channel modulators, Mites growth inhibitors, Mitochondria ATP biosynthetic enzyme inhibitors, Uncouplers of oxidative phosphorylation, Nicotinic acetylcholine receptor channel blocker (for example, Nereistoxin insecticides), Chitin synthesis inhibitors, Molting inhibitors, Ecdysone receptor agonist, Octopamine receptor agonist, Inhibitors of Mitochondrial electron transport system complex I, II, III and IV, Voltage-dependent sodium channel blockers, Acetyl CoA carboxylase inhibitor, Ryanodine receptor modulator (for example, Diamide insecticides), Chordotonal organ modulators, Microbial pesticides; and the other insecticidal, miticidal or nematicidal active ingredients.

These ingredients are classified as a class based on the action mechanism of IRAC.

Group (b) is a group consisting of Nucleic acid synthesis inhibitors (for example, Phenylamide fungicides, or Acylamino acid fungicides), cell division and cytoskeleton inhibitors (for example, MBC fungicides), Respiratory inhibitors (for example, QoI fungicides or QiI fungicides), Amino acid synthesis and protein synthesis inhibitors (for example, anilinopyridine fungicides), Signal transduction inhibitors, Lipid synthesis and membrane synthesis inhibitors, sterol biosynthesis inhibitors (for example, DMI fungicides such as triazole), cell wall synthesis inhibitors, Melanin synthesis inhibitors, Plant defense inducers, Other action point contact active fungicides, Microbial fungicides, and the other fungicidal ingredients. These are classified as a class based on the action mechanism of FRAC.

Group (c) is a plant growth modulating ingredient group (including Mycorrhizal fungi, and Root nodule bacteria).

Group (d) is a repellent ingredient group consisting of a bird repellant ingredient and an insect repellant ingredient.

Examples of the combination of the Present ingredient and the compound of the present invention are described below. For example, alanycarb+SX represents a combination of alanycarb and SX. The symbol of "SX" represents any one of the compound of the present invention selected from the Compound Class SX1 to the Compound Class SX135. Also, all of the below-mentioned present active ingredient are known ingredients, and are commercially available or may be produced by the known method. If the present ingredient is a bacterium, it is available from the bacterial authority depository. The numerical number in bracket represents a CAS RN (Register Trademark).

Combination of the Present ingredient of the above Group (a) and the compound of the present invention:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC (2-methyl-4,6-dinitrophenol)+SX, doramectin+SX, dried leaves of *Dryopteris filix-mas*+SX, emamectin-benzoate+SX, empenthrin+SX, endosulfan+SX, EPN (O-ethyl O-(4-nitrophenyl)phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of clitoriaternatea+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid)+SX, imidaclothiz+SX, imiprothrin+SX, indoxacarb+SX, isocycloseram+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides* (Brand name: Terpenoid blend QRD 460)+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate+SX, xylylcarb+SX, zeta-cypermethrin+SX, zinc phosphide+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus+SX, *Anticarsia gemmatalis* mNPV+SX, *Autographa californica* mNPV FV #11+SX, *Cydia pomonella* GV V15+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra configurata* NPV+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* GB-126+SX, *Bacillus firmus* 1-1582+SX, *Bacillus megaterium*+SX, *Bacillus* sp. AQ175+SX, *Bacillus* sp. AQ177+SX, *Bacillus* sp. AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. *Aizawai* ABTS-1857+SX, *Bacillus thuringiensis* subsp. *Aizawai* AM65-52+SX, *Bacillus thuringiensis* subsp. *Aizawai* GC-91+SX, *Bacillus thuringiensis* subsp. *Aizawai* Serotype H-7+SX, *Bacillus thuringiensis* subsp. *Kurstaki* ABTS351+SX, *Bacillus thuringiensis* subsp. *Kurstaki* BMP123+SX, *Bacillus thuringiensis* subsp. *Kurstaki* EG234+SX, *Bacillus thuringiensis* subsp. *Kurstaki* EG7841+SX, *Bacillus thuringiensis* subsp. *Kurstaki* EVB113-19+SX, *Bacillus thuringiensis* subsp. *Kurstaki* F810+SX, *Bacillus thuringiensis* subsp. *Kurstaki* HD-1+SX, *Bacillus thuringiensis* subsp. *Kurstaki* PB54+SX, *Bacillus thuringiensis* subsp. *Kurstaki* SA-11+SX, *Bacillus thuringiensis* subsp. *Kurstaki* SA-12+SX, *Bacillus thuringiensis* subsp. *Tenebriosis* NB176+SX, *Bacillus thuringiensis* subsp. *Thuringiensis* MPPL002+SX, *Bacillus thuringiensis* subsp. *morrisoni*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *Japonensis buibui*+SX, *Bacillus thuringiensis* var. san diego M-7+SX, *Bacillus thuringiensis* var. 7216+SX, *Bacillus thuringiensis* var. *aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* KV01+SX, *Lecanicillium lecanii* conidia of strain DAOM198499+SX, *Lecanicillium lecanii* conidia of strain DAOM216596+SX, *Lecanicillium muscarium* Ve6+SX, *Metarhizium anisopliae* F52+SX, *Metarhizium anisopliae* var. *acridum*+SX, *Metarhizium anisopliae* var. *anisopliae* BIPESCO 5/F52+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria usgae*+SX, *Pasteuria thoynei*+SX, *Ser-* *ratia entomophila*+SX, *Verticillium chlamydosporium*+SX, *Verticillium lecani* NCIM1312+SX.

Combination of the Present ingredient of the above Group (b) and the compound of the present invention:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, ꔛ dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate (1360819-11-9)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]pyrimidin-4-amine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentane-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentane-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentane-1-ol (1801930-07-3)+SX, methyl 3-[(4-chlorophenyl)methyl]-2-hydroxy-1-methyl-2-(1H-1,2,4-triazol-1-ylmethyl)cyclopentane-1-carboxylate (1791398-02-1)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl)cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-methoxyimino-N,3-dimethylpent-3-enamide (1445331-27-0)+SX, *Agrobacterium radiobactor* K1026+SX, *Agrobacterium radiobactor* K84+SX, *Bacillus amyloliquefaciens* (Aveo (trademark) EZ Nematicide)+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus amyloliquefaciens* subsp. *plantarum* strain D747+SX, *Bacillus licheniformis* HB-2+SX, *Bacillus licheniformis* SB3086+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX, *Bacillus subtilis* FZB24+SX, *Bacillus subtilis* GB03+SX, *Bacillus subtilis* HAI0404+SX, *Bacillus subtilis* IAB/BS03+SX, *Bacillus subtilis MBI*600+SX, *Bacillus subtilis* QST30002/AQ30002+SX, *Bacillus subtilis* QST30004/AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* O+SX, *Candida saitoana*+SX, *Chaetomium cupreum*+SX, *Clonostachys rosea*+SX, *Coniothyrium minitans* CGMCC8325+SX, *Coniothyrium minitans* CON/M/91-8+SX, *cryptococcus albidus*+SX, *Erwinia carotovora* subsp. *carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+SX, *Pseudomonas chlororaphis* 63-28+SX, *Pseudomonas chlororaphis* strain AFS009+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, *Pseudozyma floc-* culosa PF-A22UL+SX, *Pseudomonas rhodesiae* HAI-0804+SX, *Pythium oligandrum* DV74+SX, *Pythium oligandrum* strain M1+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Talaromyces flavus* V117b+SX, *Trichoderma asperellum* ICC012+SX, *Trichoderma asperellum* SKT-1+SX, *Trichoderma asperellum* strain T25+SX, *Trichoderma asperellum* T34+SX, *Trichoderma asperellum* strain TV1+SX, *Trichoderma atroviride* CNCM 1-1237+SX, *Trichoderma atroviride* LC52+SX, *Trichoderma atroviride* strain IMI 206040+SX, *Trichoderma atroviride* SC1+SX, *Trichoderma atroviride* SKT-1+SX, *Trichoderma atroviride* strain T11+SX, *Trichoderma gamsii* ICC080+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+SX, *Trichoderma harzianum* ITEM908+SX, *Trichoderma harzianum* kd+SX, *Trichoderma harzianum* MO1+SX, *Trichoderma harzianum* SF+SX, *Trichoderma harzianum* T22+SX, *Trichoderma harzianum* T39+SX, *Trichoderma harzianum* T78+SX, *Trichoderma harzianum* TH35+SX, *Trichoderma polysporum* IMI206039+SX, *Trichoderma stromaticum*+SX, *Trichoderma virens* G-41+SX, *Trichoderma virens* GL-21+SX, *Trichoderma viride*+SX, *Variovorax paradoxus* CGF4526+SX, Harpin protein+SX.

Combination of the Present ingredient of the above Group (c) and the compound of the present invention:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, ℈ dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, methyl 5-(trifluoromethyl)benzo[b]thiophen-2-carbonate+SX, 3-[(6-chloro-4-phenylquinazoline-2-yl)amino]-1-propanol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaic Virus weak+SX.

Combination of the Present ingredient of the above Group (d) and the compound of the present invention:

anthraquinone+SX, deet+SX, icaridin+SX.

The ratio of the compound of the present invention to the Present ingredient includes, but not limited thereto, as a ratio by weight (the compound of the present invention:the Present ingredient) 1,000:1 to 1:1,000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10. 1:20, and 1:50, and the others.

The present compound, the compound of the present invention, or the composition A is usually mixed with solid carrier(s), liquid carrier(s), oil(s), and/or surfactant(s), and if necessary, added by the other auxiliary agents for formulation, to formulate into emulsifiable concentrates, oil solutions, dust formulations, granules, wettable powders, wettable dispersible granules, flowables, dry flowables, microcapsules and the others. In these formulations, the present compound, the compound of the present invention, or the composition A is contained in usually 0.1 to 99% by weight, preferably 0.2 to 90%.

Examples of the solid carrier include fine powders or granules of clays (for example, kaolin clay, diatomaceous earth, bentonite, or acid white clay), dry silica, wet silica, hydrated silica, talcs, ceramics, other inorganic minerals (for example, sericite, quartz, sulfur, active carbon, or calcium carbonate); as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseed oil).

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates. Specific examples thereof include Nimbus (registered trademark), Assist (registered trademark), Aureo (registered trademark), Iharol (registered trademark), Silwet L-77 (registered trademark), BreakThru (registered trademark), Sundancell (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANGLE (registered trademark), and the others.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of an application of the present compound, the compound of the present invention, or the composition A include a spreading to stems and leaves of soybeans, an application to seeds, and an application to soil for cultivating soybeans.

The application dose of the present compound, or the compound of the present invention may be varied depending on a climate condition, a formulation form, an application period, an application method, an application site, plant diseases to be controlled, plant to be applied, and the others. In the cases where these compounds are spread to stems and leaves of soybean or are applied to soil for cultivating soybeans, the application dose thereof is within a range of usually 1 to 500 g, preferably 2 to 200 g per 1,000 m$^2$. In the cases where these compounds are applied to seeds, the application dose thereof is within a range of 0.01 to 100 g, preferably 0.01 to 50 g per 1 Kg of seeds. The application dose of the composition A is within a range of usually 1 to 500 g per 1,000 m$^2$ in the case where it is spread to stems and leaves of soybean or are applied to soil for cultivating soybeans. In the cases where it is applied to seeds, the application dose thereof is within a range of usually 0.001 to 100 g per 1 Kg of seeds. The emulsifiable concentrate, the wettable powder, the suspension etc., is usually applied by diluting them with water. In these cases, the concentration of the present compound, the compound of the present invention, or the composition A after the dilution is within a range of usually 0.0005 to 2% by weight, preferably 0.005 to 2% by weight. The dust formulation or the granular formulation, etc., is usually applied as itself without diluting them.

The above-mentioned soybean may be a plant which can be produced by natural mating, a soybean which can be generated by mutation, a F1 hybrid soybean, and a transgenic soybean (also referred to as genetically modified soybean). In general, these soybeans have characteristics that are tolerance to herbicides, accumulation of toxic substances against pests (which is also referred to as pest resistance), suppression of sensitivity to diseases (which is also referred to as disease resistance), increase of yield potential, improvement of tolerance to biological and abiotic stress factors, modification of quality of products (for example, increase or decrease of the content of ingredient(s), change of composition, or improvement of storability and processability), and the like. Techniques for producing the above-mentioned soybeans include, for example, traditional breed improvement techniques; genetic recombination technologies; genome breeding technologies; new breeding techniques; and genome editing techniques.

Examples of the soybeans which are imparted with herbicide tolerance include auxin type herbicidal compounds such as 2,4-D, dicamba; soybeans having tolerance to glufosinate, soybeans having tolerance to glyphosate, soybeans having tolerance to isoxaflutole, soybeans having tolerance to 4-hydroxyphenylpyruvate dioxygenase inhibitory herbicides (such as mesotrione); soybeans having tolerance to imidazolinone type herbicides; acetolactate synthase (ALS) inhibitory herbicides (such as sulfonylurea herbicide inhibitors); and soybeans having tolerance to protoporphyrinogen oxidase inhibitory herbicides (such as flumioxazin), and the others.

The soybeans which are imparted with herbicide tolerance by genetic recombination technologies can be produced by introducing foreign genes (such as genes derived from other organisms such as microorganisms). For example, a tolerance to 2,4-D is introduced by "aad-12" which is a gene derived from *Delftia acidovorans*; a tolerance to Dicamba is introduced by "dmo" which is a gene derived from *Stenotrophomonas maltophilia* strain DI-6; a tolerance to glufosinate is introduced by "bar" which is a gene derived from *Streptomyces hygroscopicus* or "pat" which is a gene derived from *Streptomyces viridochromogenes*; a tolerance to glyphosate is introduced by "2mepsps" which is a gene derived from *Zea mays*, "CP4 epsps" which is a gene derived from *Agrobacterium tumefaciens* strain CP4, or "gat4601" which is a gene derived from *Bacillus licheniformis*; a tolerance to isoxaflutole is introduced by "hppdPF W336" which is a gene derived from *Pseudomonas fluorescens* strain A32; a tolerance to mesotrione is introduced by "avhppd-03" which is a gene derived from Oat (*Avena sativa*); a tolerance to imidazolinone herbicides is introduced by "csr1-2" which is a gene derived from *Arabidopsis thaliana*; a tolerance to sulfonylurea herbicides is introduced by "gm-hra" which is a gene derived from *Glycine max*.

Examples of soybeans which are imparted with herbicides by traditional breed improvement techniques or genome breeding technologies include soybean having tolerance to sulfonylurea ALS inhibitory herbicides (such as thifensulfuron methyl) ("STS (registered trademark) soybean").

Examples of soybeans which are imparted with herbicides by a new breeding technique include the plants in which glyphosate tolerance is imparted to nontransgenic soybean by using Roundup Ready (Registered trademark) having glyphosate tolerance as a rootstock (see, Weed Technology 27: 412-416 2013).

Examples of soybeans which are imparted with pest tolerance include soybean having tolerance to Lepidoptera pests (such as Pseuoplusia includes, *Helicoverpa zea, Spo-* doptera frugiperda), soybean having tolerance to *Hemiptera* (such as *Aphis glycines*), and soybean having tolerance to Nematode (such as *Heterodera glycines, Meloidogyne incognita*).

The soybeans which are imparted with pest tolerance by genetic recombination technologies can be produced by introducing foreign genes (such as genes encoding δ-endotoxin which is insecticidal protein derived from *Bacillus thuringiensis* For example, a tolerance to Lepidoptera pests is introduced by "cry1Ac" which is a gene derived from *Bacillus thuringiensis* subsp. *Kurstaki* strain HD73, "cry1F" which is a gene derived from *Bacillus thuringiensis* var. *aizawai*, "cry1A.105" which is a gene derived from *Bacillus thuringiensis* subsp. *kumamotoensis*, or "cry2Ab2" which is a gene derived from *Bacillus thuringiensis* subsp. *kumamotoensis*.

Examples of soybeans which are imparted with pest tolerance by traditional breed improvement techniques or genome breeding technologies include soybean having as a resistance gene against aphid a resistance gene Rag1 (Tolerance Aphid Gene 1) or a gene Rag1 (Tolerance Aphid Gene 1) and also showing resistance to aphids (see J. Econ. Entomol., 2015, 108, 326); soybean showing resistance to *Heterodera glycines* (see Phytopathology, 2016, 106, 1444); and soybean showing resistance to *Spodoptera litura* (that is, "Fukuminori").

Examples of soybeans which are imparted with disease resistance include soybean which is imparted with a resistance to soybean rust disease by traditional breed improvement techniques or genetic recombination technologies. Examples of commonly used resistance genes include, not limited thereto, Rpp1, Rpp2, Rpp3, Rpp4, Rpp5, and Rpp6. These genes may be introduced alone into a soybean, or may be introduced in any combinations of a plural of these genes into soybean. These genes are described in the following scientific documents: Crop Science, 2007, 47, 837; Theoretical and Applied Genetics, 2008, 117, 57; Theoretical and Applied Genetics, 117, 545; Crop Science, 2009, 49, 783; Theoretical and Applied Genetics, 2009, 119, 271; Theoretical and Applied Genetics, 2010, 121, 1023; Theoretical and Applied Genetics, 2012, 125, 133.

Examples of the soybeans which are imparted with disease resistance by genome breeding technologies include soybean showing resistance to soybean stem disease due to *Phytophthora sojae* by destructing RXLR effector gene (Avr4/6) using CRISPR-Cas9 (see, Mol. Plant. Pathol., 2016, 17, 127).

Also, soybeans which is imparted with a resistance to soybean diseases other than soybean rust disease (for example, frogeye leaf spot, brown ring spot disease, stem disease, sudden death syndrome) are also included.

Examples of soybeans in which a quality of product is modified by genetic recombination technologies include soybean "Plenish (Trademark)" or "Treus (Trademark)" in which partial gene of ω-6 desaturase (gm-fad2-1) derived from *Glycine max* which is the fatty acid desaturase enzyme, is introduced and an expression of the same genes are then suppressed, and the oleic acid contents is enriched; soybean "Vistive Gold (Trademark)") in which the contents of saturated fatty acid is reduced by introducing genes that produce double-stranded RNA of acyl-acyl carrier protein-thioesterase gene (fatb1-A) derived from *Glycine max* and genes that produce double-stranded RNA of 6-12 desaturase (fad2-1A) derived from *Glycine max*; genetically modified soybean in which the contents of stearidonic acid as one of ω3 fatty acid is enriched by introducing δ-6 desaturase gene (Pj. D6D) derived from *Primula juliae* and δ-12 desaturase gene (Nc. Fad3) derived from *Neurospora crassa*; soybean in which the oil contents is altered; soybean in which the allergen contents is reduced (see U.S. Pat. No. 6,864,362); soybeans in which the lysine contents are increased (see Bio/Technology, 1995, 13, 577); soybean in which the composition of methionine, leucine, isoleucine, and valine is modified; soybean in which the contents of a sulfur-containing amino acid is increased (see WO 1997/041239 A1); soybean in which the contents of phenolic compound is increased (see US publication No. 2008/235829); soybean in which the contents of vitamin E is increased (see WO 2004/058934 A1).

Examples of soybeans in which a quality of product is modified by genetic recombination technologies include soybean in which the contents of allergen is reduced (that is, "Yumeminori").

Examples of the plants in which the traits related to plant growth and yields are altered include soybean in which the plant growth is enhanced by introducing a gene derived from thale cress encoding transcription factor which regulates daily periodicity ("bbx32"), and thereby a high yields are expected.

Examples of soybeans having other characteristics include soybean in which an uptake of phosphorus is improved; soybean which is imparted with fertility traits; soybean which is imparted with tolerance to drought; soybean which is imparted with tolerance to low temperature; soybean which is imparted with tolerance to high salinity; soybean in which iron chlorosis is altered; and soybean in which chloride sensitivity is altered.

Examples of the above-mentioned soybeans encompass also soybeans in which two or more characteristics selected from the above-mentioned herbicide tolerance, pest resistance, disease resistance, abiotic stress tolerance, traits relating to growth or yield, traits relating to nutrient intake, traits relating to product quality, or fertility traits are imparted. Examples of these soybeans include soybean having a tolerance to glyphosate; soybean having a tolerance to glyphosate; soybean having tolerance to glufosinate; soybean having a resistance to frogeye leaf spot, Sudden Death Syndrome, southern stem canker, *Phytophthora* root rot, southern root-knot nematode, *Sclerotinia* white mold, brown stem rot, or soybean cyst nematode; soybean in which iron chlorosis is improved; and soybean in which chloride sensitivity is altered (that is, "Credenz (registered trademark) soybean").

Hereinafter, the soybeans that is commercially available or has been developed are listed below. Hereafter, they are described as [Event Name, Event code, Tread name]. Also, NA represents an information that is not existed or is unavailable. Many of these soybeans is listed in a registration database (GM APPROVAL DATABASE) in a website (http://www.isaaa.org/) of INTERNATINAL SERVICE for the ACQUISITION of AGRI-BIOTECH APPLICATIONS, ISAAA).

[260-05(G94-1, G94-19, G168), DD-026005-3, NA], [A2704-12, ACS-GM005-3, Liberty Link (trademark) soybean], [A2704-21, ACS-GM004-2, Liberty Link (trademark) soybean], [A5547-127, ACS-GM006-4, Liberty Link (trademark) soybean], [A5547-35, ACS-GM008-6, Liberty Link (trademark) soybean], [CV127, BPS-CV127-9, Cultivance], [DAS44406-6, DAS-44406-6, NA], [DAS68416-4, DAS-68416-4, Enlist (trademark) Soybean], [DAS68416-4xMON89788, DAS-68416-4xMON-89788-1, NA], [DAS81419, DAS-81419-2, NA], [DAS81419xDAS44406-6, DAS-81419-2xDAS-44406-6, NA], [DP305423, DP-305423-1, Treus (trademark) or Plenish (trademark)],

[DP305423xGTS40-3-2, DP-305423-1xMON-04032-6, NA], [DP356043, DP-356043-5, Optimum GAT (trademark)], [FG72(FG072-2,FG072-3), MST-FG072-3, NA], [FG72xA5547-127, MST-FG072-3xACS-GM006-4, NA], [GTS40-3-2(40-3-2), MON-04032-6, Roundup Ready (trademark) soybean], [GU262, ACS-GM003-1, Liberty Link (trademark) soybean], [IND-00410-5, IND-00410-5, Verdeca HB4 Soybean], [MON87701, MON-87701-2, NA], [MON87701xMON89788, MON-87701-2xMON-89788-1, Intacta (trademark) Roundup Ready (trademark) 2 Pro], [MON87705, MON-87705-6, Vistive Gold (trademark)], [MON87705xMON87708, MON-87705-6xMON-87708-9, NA], [MON87705xMON87708xMON89788, MON-87705-6xMON-87708-9xMON-89788-1, NA], [MON87705xMON89788, MON-87705-6xMON-89788-1, NA], [MON87708, MON-87708-9, Genuity (registered trademark) Roundup Ready (trademark) 2 Xtend (trademark)], [MON87708xMON89788, MON-87708-9xMON-89788-1, Roundup Ready Xtend (registered trademark)], [MON87712, MON-87712-4, NA], [MON87751, MON-87751-7, NA], [MON87751xMON87701xMON87708xMON89788, MON-87751-7xMON-87701-2xMON87708xMON89788, NA], [MON87769, MON87769-7, NA], [, MON87769xMON89788, MON-87769-7xMON-89788-1, NA], [MON89788, MON-89788-1, Genuity (registered trademark) Roundup Ready 2 Yield (trademark)], [SYHT0H2, SYN-000H2-5, Herbicide-tolerant Soybean line], [W62, ACS-GM002-9, Liberty Link (trademark) soybean], [W98, ACS-GM001-8, Liberty Link (trademark) soybean], [OT96-15, OT96-15, NA], [NA, NA, STS (registered trademark) soybean], [NA, NA, Credenz (registered trademark) soybean], [NA, NA, Enlist E3 (trademark)], [NA, NA, Enlist (trademark) Roundup Ready 2 Yield (registered trademark)], [NA, NA, Fukuminori], [NA, NA, Yumeminori], [DP305423 x MOV87708, DP-305423-1 x MON-87708-9, NA], [DP305423 x MOV87708 x MON89788, DP-305423-1 x MON-87708-9 x MON-89788-1, NA], [DP305423 x MON89788, DP-305423-1 x MON-89788-1, NA]

An application of the present compound, the compound of the present invention, or the composition A can provide an effect of a promotion of the growth of a plant, such as an increase in the rate of seedling establishment, an increase in the number of healthy leaves, an increase in the height of the plant, an increase in the weight of the plant body, an increase in the leaf area, an increase in the number or weight of seeds, an increase in the number of occasion of flower setting or fruit setting, and a promoted growth of a root and the like. Also, an application of the present compound, the compound of the present invention, or the composition A can provide an increase of a resistance against an abiotic stress such as a temperature stress (for example, high-temperature stress or low-temperature stress), water stress (for example, drought stress or excess water stress), and a salt stress.

EXAMPLES

Hereinafter, the present invention is explained in more detail by using Preparation examples, Formulation examples, and Test examples, however, the present invention should not be limited to these examples.

Herein, Me represents a methyl group, Et represents an ethyl group, Pr represents a propyl group, i-Pr represents isopropyl group, Bu represents a butyl group, i-Bu represents an isobutyl group, t-Bu represents a t-butyl group, Pen represents a pentyl group, Hex represents a hexyl group, c-Pr represents a cyclopropyl group, c-Bu represents a cyclobutyl group, c-Pen represents a cyclopentyl group, c-Hex represents a cyclohexyl group, and Ph represents a phenyl group. When the Ph group has any substituent(s), the substituent(s) is described together with a substitution position before the symbol. For example, 3,4-Me$_2$-Ph represents a 3,4-dimethylphenyl group.

The preparation examples of the present compounds and the compounds of the present invention are described.

Reference Preparation Example 1

A mixture of methyl (3Z)-2-(5-bromo-2-methylphenoxy)-3-methoxyacrylate which was prepared by the method described in WO 2001/000562 A1 (hereinafter, Intermediate compound 1) 5.0 g, triethylamine 15 mL, copper(I) iodide 0.32 g, PdCl$_2$(PPh$_3$)$_2$ 1.17 g, trimethylsilyl acetylene 11.5 mL, and acetonitrile 25 mL was stirred at 80° C. for 4 hours under nitrogen atmosphere. The resulting mixture was concentrated under reduced pressure, and purified by a silica gel column chromatography to obtain methyl (3Z)-2-[5-(2-trimethylsilylethynyl)-2-methylphenoxy]-3-methoxyacrylate (hereinafter, referred to as Intermediate compound 2). To a mixture of the intermediate compound 2 1.5 g and THF 20 mL was added tetrabutylammonium fluoride (1M tetrahydrofuran solution) 4.0 mL at 0° C., and the mixture was stirred at room temperature for 16 hours. To the resulting mixture were added water and 4N hydrochloric acid successively, and the mixture was extracted with MTBE. The resulting organic layers were dried over sodium sulfate, and concentrated under reduced pressure. The resulting residue was subjected to a silica gel column chromatography to obtain an intermediate compound 3 represented by the following formula 0.72 g.

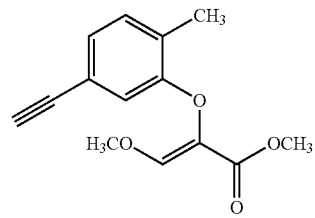 [SMILES: C#Cc1ccc(C)c(O/C(=C\OC)C(=O)OC)c1]

Intermediate compound 3: $^1$H-NMR (CDCl$_3$) δ: 7.33 (1H, s), 7.12-7.03 (2H, m), 6.84 (1H, d), 3.88 (3H, s), 3.71 (3H, s), 3.00 (1H, s), 2.35 (3H, s).

Reference Preparation 2

To a mixture of N-(3-bromophenyl)-N-methylglycine methyl ester which was prepared by the method described in WO 2010/038081 A1 4.6 g, THF 22 mL, and DMF 66 mL was added sodium hydride (60%, in oil) 1.6 g at 0° C., and the mixture was stirred for 1 hour. To the resulting mixture was added methyl formate 3.4 L, and the mixture was stirred at room temperature for 16 hours. To the resulting mixture was added 1N hydrochloric acid, and the mixture was extracted with MTBE. The resulting organic layers were dried over anhydrous magnesium sulfate, and concentrated under reduced pressure. To the resulting residue were added THF 60 mL and DMF 30 mL, the mixture was stirred, and thereto were added potassium carbonate 2.7 g and iodomethane 1.3 mL at 0° C. successively, and the mixture was stirred at room temperature for 16 hours. To the resulting mixture was added saturated aqueous solution of ammonium chloride, and the mixture was extracted with MTBE. The resulting organic layers were dried over anhydrous magnesium sulfate, and concentrated under reduced pressure. The resulting residue was subjected to a silica gel column chromatography to obtain an intermediate compound 4 represented by the following formula 2.0 g.

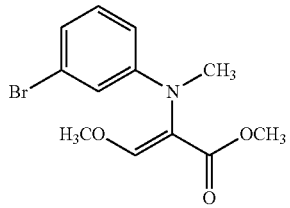 [SMILES: CO/C=C(/C(=O)OC)N(C)c1cccc(Br)c1]

Intermediate compound 4: $^1$H-NMR (CDCl$_3$) δ: 7.42 (1H, s), 7.03 (1H, t), 6.85-6.81 (1H, m), 6.78 (1H, t), 6.57-6.53 (1H, m), 3.88 (3H, s), 3.69 (3H, s), 3.04 (3H, s).

Reference Preparation 3

A mixture of the intermediate compound 1 1.0 g, palladium(II) acetate 0.07 g, trimethylsilane 0.68 mL, 1,4-bis(diphenylphoshino)butane 0.21 g, sodium carbonate 0.52 g, N-formyl saccharin 1.05 g, and DMF 12 mL was stirred at 80° C. for 5 hours. To the resulting mixture was added water, and the mixture was extracted with ethyl acetate. The resulting organic layers were dried over sodium sulfate, and concentrated under reduced pressure. The resulting residue was subjected to a silica gel column chromatography to obtain the intermediate compound 5 represented by the following formula 0.38 g.

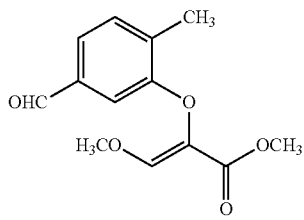 [SMILES: CO/C=C(\Oc1cc(C=O)ccc1C)C(=O)OC]

Intermediate compound 5: $^1$H-NMR (CDCl$_3$) δ: 9.88 (1H, s), 7.42 (1H, dd), 7.36 (1H, s), 7.33 (1H, d), 7.23 (1H, d), 3.88 (3H, s), 3.71 (3H, s), 2.43 (3H, s).

Preparation Example 1

A mixture of the intermediate compound 1 0.50 g, 1,2-methylphenylboronic acid 0.27 g, [1.1'-bis(diphenylphoshino)ferrocene]palladium(II) dichloride dichloromethane adduct 0.11 g, tripotassium phosphate 0.85 g, dimethoxyethane 15 mL, and water 1 mL stirred at 80° C. for 5 hours. The resulting mixture was cooled to room temperature, and then filtered. The filtrates were dried over anhydrous magnesium sulfate, and concentrated under reduced pressure. The resulting residue was subjected to a silica gel column chromatography (ethyl acetate:hexane=1:4) to obtain the present compound 52 represented by the following formula 0.42 g.

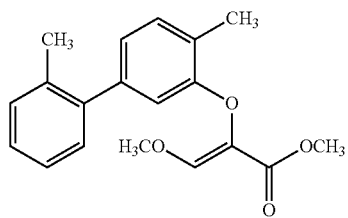 [SMILES: CO/C=C(\Oc1cc(-c2ccccc2C)ccc1C)C(=O)OC]

Present Compound 52: $^1$H-NMR (CDCl$_3$) δ: 7.28 (1H, s), 7.25-7.17 (5H, m), 6.87 (1H, dd), 6.69 (1H, d), 3.85 (3H, s), 3.70 (3H, s), 2.40 (3H, s), 2.23 (3H, s).

Preparation Example 1-1

The compounds which were prepared according to the Preparation Example 1 and their physical property value are shown below.

A compound represented by formula (1d):

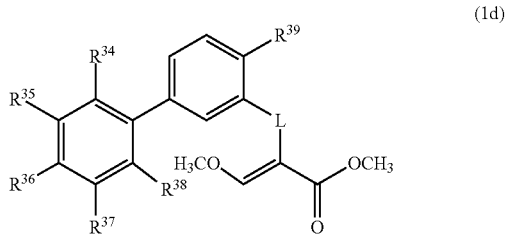

(1d)

wherein the combination of $R^{34}$, $R^{35}$, $R^{36}$, $R^{37}$, $R^{38}$, $R^{39}$ and L represents any combinations indicated in [Table 1].

TABLE 1

| Present Compound | $R^{34}$ | $R^{35}$ | $R^{36}$ | $R^{37}$ | $R^{38}$ | $R^{39}$ | L |
|---|---|---|---|---|---|---|---|
| 53 | F | H | H | H | H | Me | O |
| 54 | Cl | H | H | H | H | Me | O |
| 55 | H | Cl | H | H | H | Me | O |
| 56 | H | H | Cl | H | H | Me | O |
| 57 | H | H | H | H | H | Cl | O |
| 58 | F | F | H | H | H | Me | O |
| 59 | F | H | F | H | H | Me | O |
| 60 | F | H | H | F | H | Me | O |
| 61 | F | H | H | H | F | Me | O |
| 62 | F | F | F | H | H | Me | O |
| 63 | H | F | F | F | H | Me | O |
| 87 | H | OPh | H | H | H | Me | O |

Present Compound 53: $^1$H-NMR (CDCl$_3$) δ: 7.41-7.35 (1H, m), 7.33 (1H, s), 7.31-7.07 (5H, m), 6.93-6.91 (1H, m), 3.87 (3H, s), 3.71 (3H, s), 2.40 (3H, s).

Present Compound 54: $^1$H-NMR (CDCl$_3$) δ: 7.46-7.42 (1H, m), 7.31 (1H, s), 7.31-7.20 (4H, m), 6.97 (1H, dd), 6.84 (1H, d), 3.86 (3H, s), 3.70 (3H, s), 2.40 (3H, s).

Present Compound 55: $^1$H-NMR (CDCl$_3$) δ: 7.50 (1H, t), 7.42-7.30 (4H, m), 7.27-7.24 (1H, m), 7.13 (1H, dd), 6.90 (1H, d), 3.92 (3H, s), 3.75 (3H, s), 2.42 (3H, s).

Present Compound 56: $^1$H-NMR (CDCl$_3$) δ: 7.47-7.37 (5H, m), 7.25 (1H, d), 7.12 (1H, dd), 6.90 (1H, d), 3.91 (3H, s), 3.74 (3H, s), 2.41 (3H, s).

Present Compound 57: $^1$H-NMR (CDCl$_3$) δ: 7.51-7.47 (2H, m), 7.45-7.40 (3H, m), 7.38 (1H, s), 7.37-7.33 (1H, m), 7.16 (1H, dd), 7.01 (1H, d), 3.89 (3H, s), 3.74 (3H, s).

Present Compound 58: ¹H-NMR (CDCl₃) δ: 7.34 (1H, s), 7.26-7.22 (1H, m), 7.16-7.05 (4H, m), 6.92-6.89 (1H, m), 3.88 (3H, s), 3.72 (3H, s), 2.40 (3H, s).

Present Compound 59: ¹H-NMR (CDCl₃) δ: 7.37-7.29 (2H, m), 7.22 (1H, d), 7.05-7.01 (1H, m), 6.94-6.83 (3H, m), 3.87 (3H, s), 3.71 (3H, s), 2.39 (3H, s).

Present Compound 60: ¹H-NMR (CDCl₃) δ: 7.34 (1H, s), 7.24 (1H, d), 7.11-7.03 (3H, m), 7.00-6.92 (1H, m), 6.90-6.88 (1H, m), 3.88 (3H, s), 3.72 (3H, s), 2.40 (3H, s).

Present Compound 61: ¹H-NMR (CDCl₃) δ: 7.31 (1H, s), 7.26-7.20 (2H, m), 7.05-7.01 (1H, m), 6.97-6.92 (2H, m), 6.83-6.81 (1H, m), 3.86 (3H, s), 3.71 (3H, s), 2.40 (3H, s).

Present Compound 62: ¹H-NMR (CDCl₃) δ: 7.34 (1H, s), 7.25-7.21 (1H, m), 7.12-6.94 (3H, m), 6.86-6.81 (1H, m), 3.88 (3H, s), 3.72 (3H, s), 2.40 (3H, s).

Present Compound 63: ¹H-NMR (CDCl₃) δ: 7.37 (1H, s), 7.23 (1H, d), 7.13-7.02 (3H, m), 6.80 (1H, d), 3.90 (3H, s), 3.73 (3H, s), 2.39 (3H, s).

Present Compound 87: ¹H-NMR (CDCl₃) δ: 7.38-7.31 (4H, m), 7.26-7.15 (3H, m), 7.11 (2H, t), 7.05 (2H, d), 6.96-6.87 (2H, m), 3.86 (3H, s), 3.70 (3H, s), 2.38 (3H, s).

A compound represented by formula (1j):

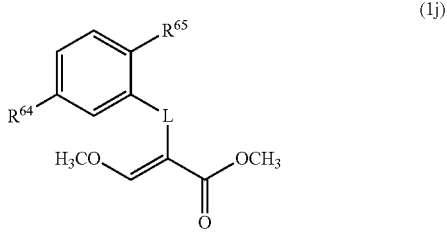

(1j)

wherein the combination of $R^{64}$, $R^{65}$, and L represents any combinations indicated in any one of [Table 2] and [Table 3]

TABLE 2

| Present compound | $R^{64}$ | $R^{65}$ | L |
|---|---|---|---|
| 64 | 3-thienyl | Me | O |
| 65 | 3-thienyl (isomer) | Me | O |
| 66 | 5-fluoropyridin-3-yl | Me | O |
| 67 | 2-fluoropyridin-3-yl | Me | O |
| 68 | 5-fluoropyridin-2-yl | Me | O |
| 69 | 5-chloropyridin-3-yl | Me | O |
| 70 | benzothiophen-3-yl | Me | O |
| 88 | 6-cyanopyridin-2-yl | Me | O |

TABLE 3

| Compound of the present invention | $R^{64}$ | $R^{65}$ | L |
|---|---|---|---|
| 1 | H₃C–CH₂–CH₂–CH=CH– | Me | O |
| 2 | (H₃C)₂C=CH– | Me | O |
| 3 | cyclopropyl–CH=CH– | Me | O |

Present compound 64: ¹H-NMR (CDCl₃) δ: 7.38 (1H, s), 7.27-7.21 (2H, m), 7.19-7.17 (2H, m), 7.09-7.05 (1H, m), 6.96 (1H, s), 3.92 (3H, s), 3.73 (3H, s), 2.39 (3H, s).

Present compound 65: ¹H-NMR (CDCl₃) δ: 7.39-7.36 (3H, m), 7.34-7.31 (1H, m), 7.20-7.17 (2H, m), 6.95 (1H, d), 3.91 (3H, s), 3.74 (3H, s), 2.39 (3H, s).

Present compound 66: ¹H-NMR (CDCl₃) δ: 8.59 (1H, t), 8.42 (1H, d), 7.53-7.48 (1H, m), 7.37 (1H, s), 7.29-7.25 (1H, m), 7.12 (1H, dd), 6.89 (1H, d), 3.90 (3H, s), 3.73 (3H, s), 2.41 (3H, s).

Present compound 67: ¹H-NMR (CDCl₃) δ: 8.18-8.13 (1H, m), 7.85-7.77 (1H, m), 7.34 (1H, s), 7.26-7.22 (2H, m), 7.12-7.08 (1H, m), 6.95-6.92 (1H, m), 3.89 (3H, s), 3.72 (3H, s), 2.41 (3H, s).

Present compound 68: ¹H-NMR (CDCl₃) δ: 8.58 (1H, d), 7.67 (1H, dd), 7.58 (1H, d), 7.48 (1H, dd), 7.38-7.36 (2H, m), 7.26-7.23 (1H, m), 3.89 (3H, s), 3.71 (3H, s), 2.40 (3H, s).

Present compound 69: ¹H-NMR (CDCl₃) δ: 8.63 (1H, d), 8.51 (1H, d), 7.77 (1H, t), 7.37 (1H, s), 7.29-7.27 (1H, m), 7.11 (1H, dd), 6.87 (1H, d), 3.90 (3H, s), 3.73 (3H, s), 2.41 (3H, s).

Present compound 70: ¹H-NMR (CDCl₃) δ: 7.92-7.88 (1H, m), 7.87-7.83 (1H, m), 7.38-7.34 (2H, m), 7.34 (1H, s), 7.31 (1H, s), 7.28-7.27 (1H, m), 7.13 (1H, dd), 6.94 (1H, d), 3.88 (3H, s), 3.73 (3H, s), 2.43 (3H, s).

Present compound 88: ¹H-NMR (CDCl₃) δ: 7.88-7.80 (2H, m), 7.57 (1H, dd), 7.52 (1H, dd), 7.45 (1H, d), 7.40 (1H, s), 7.27 (1H, d), 3.92 (3H, s), 3.72 (3H, s), 2.42 (3H, s).

Compound 1 of the present invention: ¹H-NMR (CDCl₃) δ: 7.33 (1H, s), 7.07 (1H, d), 6.91 (1H, dd), 6.67 (1H, d), 6.27 (1H, d), 6.10 (1H, td), 3.87 (3H, s), 3.70 (3H, s), 2.32 (3H, s), 2.17-2.12 (2H, m), 1.52-1.43 (2H, m), 0.94 (3H, t).

Compound 2 of the present invention: ¹H-NMR (CDCl₃) δ: 7.32 (1H, s), 7.08 (1H, d), 6.91 (1H, dd), 6.72 (1H, d), 5.79-5.71 (1H, m), 3.87 (3H, s), 3.70 (3H, s), 2.32 (3H, s), 1.96 (3H, s), 1.76 (3H, d).

Compound 3 of the present invention: ¹H-NMR (CDCl₃) δ: 7.32 (1H, d), 7.05 (1H, d), 6.86 (1H, dd), 6.63 (1H, d), 6.36 (1H, d), 5.61 (1H, dd), 3.87 (3H, d), 3.70 (3H, d), 2.31 (3H, s), 1.52 (1H, m), 0.81-0.77 (2H, m), 0.50-0.46 (2H, m).

The present compound 71 and the present compound 72 each represented by the following formula

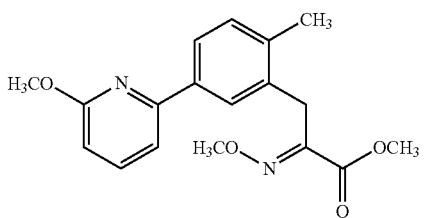 [SMILES: CO/N=C(\Cc1cc(-c2cccc(OC)n2)ccc1C)C(=O)OC]

Present compound 71: ¹H-NMR (CDCl₃) δ: 7.84-7.76 (2H, m), 7.62 (1H, dd), 7.30-7.23 (2H, m), 6.68 (1H, dd), 4.13 (3H, s), 4.05 (3H, s), 4.00 (2H, s), 3.84 (3H, s), 2.43 (3H, s).

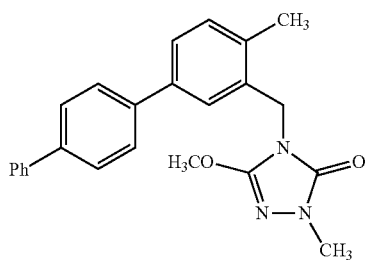 [SMILES: COc1nn(C)c(=O)n1Cc1cc(-c2ccc(-c3ccccc3)cc2)ccc1C]

Present compound 72: ¹H-NMR (CDCl₃) δ: 7.71-7.61 (6H, m), 7.52-7.44 (4H, m), 7.41-7.36 (1H, m), 7.30-7.26 (1H, m), 4.82 (2H, s), 3.97 (3H, s), 3.43 (3H, s), 2.48 (3H, s).

Preparation Example 2

A mixture of the intermediate compound 1 0.40 g, 1,4-(trifluoromethyl)-1H-pyrazole 0.27 g, copper (I) iodide 0.20 g, potassium carbonate 0.36 g, trans-N,N'-dimethylcyclohexan-1,2-diamine 0.20 mL, and DMF 8 mL was stirred at 130° C. for 15 hours under nitrogen atmosphere. To the resulting mixture were added copper(I) iodide 0.20 g, and trans-N,N'-dimethylcyclohexan-1,2-diamine 0.20 mL, and the mixture was stirred at 130° C. for 5 hours. To the resulting mixture was added saturated aqueous solution of sodium hydrocarbonate at room temperature, and the mixture was extracted with ethyl acetate. The resulting organic layers were dried over anhydrous magnesium sulfate, and concentrated under reduced pressure. The resulting residue was subjected to a silica gel column chromatography (ethyl acetate:hexane=1:4) to obtain the compound 4 of the present invention represented by the following formula 0.04 g.

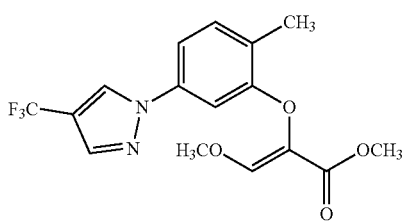 [SMILES: CO/C=C(\Oc1cc(-n2cc(C(F)(F)F)cn2)ccc1C)C(=O)OC]

Compound 4 of the present invention: ¹H-NMR (CDCl₃) δ: 8.08 (1H, s), 7.85 (1H, s), 7.37 (1H, s), 7.28-7.23 (1H, m), 7.15 (1H, dd), 7.08 (1H, d), 3.90 (3H, s), 3.72 (3H, s), 2.38 (3H, s).

Preparation Example 2-1

The compounds which were prepared according to the method described in Preparation Example 2 and their physical property values are shown below.

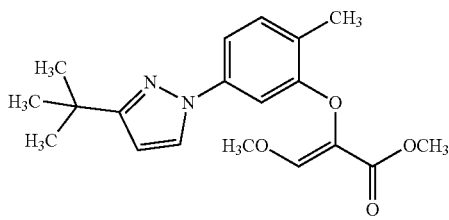 [SMILES: CO/C=C(\Oc1cc(-n2ccc(C(C)(C)C)n2)ccc1C)C(=O)OC]

Compound 5 of the present invention: ¹H-NMR (CDCl₃) δ: 7.69 (1H, d), 7.35 (1H, s), 7.19-7.17 (2H, m), 7.05-7.03 (1H, m), 6.26 (1H, d), 3.89 (3H, s), 3.71 (3H, s), 2.35 (3H, s), 1.35 (9H, s).

Preparation Example 3

To a mixture of the intermediate compound 3 0.40 g and THF 10 mL was added butyl lithium (2.6 M hexane solution) 1.25 mL at 0° C., and the mixture was stirred for 1 hour. To the resulting mixture was added iodomethane 0.21 mL at 0° C., and the mixture was stirred for 2 hours. To the resulting mixture was added saturated aqueous solution of ammonium chloride, and the mixture was extracted with ethyl acetate. The resulting organic layers were dried over anhydrous magnesium sulfate, and concentrated under reduced pressure. The resulting residue was subjected to a silica gel column chromatography (ethyl acetate:hexane=1:9) to obtain the present compound 73 represented by the following formula 0.04 g.

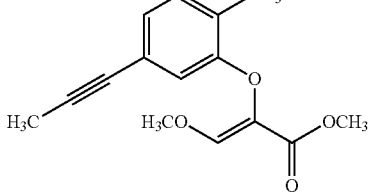

Present compound 73: ¹H-NMR (CDCl₃) δ: 7.31 (1H, s), 7.06 (1H, d), 6.95 (1H, d), 6.75 (1H, s), 3.87 (3H, s), 3.70 (3H, s), 2.32 (3H, s), 2.02 (3H, s).

Preparation Example 3-1

The compounds which were prepared according to the method described in Preparation Example 3 and their physical property values are shown below.

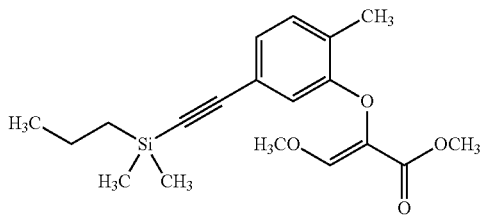 [SMILES: CCC[Si](C)(C)C#Cc1ccc(C)c(O/C(=C\OC)C(=O)OC)c1]

Present compound 74: $^1$H-NMR (CDCl$_3$) δ: 7.33 (1H, s), 7.07 (1H, d), 7.03 (1H, d), 6.79 (1H, s), 3.88 (3H, s), 3.71 (3H, s), 2.33 (3H, s), 1.42-1.49 (2H, m), 1.01 (3H, t), 0.66-0.70 (2H, m), 0.20 (6H, s).

Preparation Example 4

A mixture of the intermediate compound 1 0.50 g, 3-methyl-1-butyne 0.68 mL, PdCl$_2$(PPh$_3$)$_2$ 0.06 g, tetrabutylammonium fluoride (1M tetrahydrofuran solution) 5.0 mL, and THF 5 mL was stirred at 80° C. for 7 hours. The resulting mixture was cooled to room temperature, and thereto was then added saturated aqueous solution of sodium hydrocarbonate, and the mixture was extracted with ethyl acetate. The resulting organic layers were dried over anhydrous magnesium sulfate, and concentrated under reduced pressure. The resulting residue was subjected to a silica gel column chromatography (ethyl acetate:hexane=1:9) to obtain the present compound 75 represented by the following formula 0.26 g.

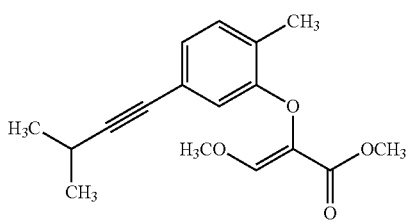 [SMILES: CO/C=C(\Oc1cc(C#CC(C)C)ccc1C)C(=O)OC]

Present compound 75: $^1$H-NMR (CDCl$_3$) δ: 7.32 (1H, s), 7.05 (1H, d), 6.95 (1H, d), 6.73 (1H, s), 3.87 (3H, s), 3.70 (3H, s), 2.80-2.69 (1H, m), 2.32 (3H, s), 1.24 (6H, d).

Preparation Example 4-1

The compounds which were prepared according to the method described in Preparation Example 4 and their physical property values are shown below.

Present Compounds 76 to 80, and the compounds 6 to 9 of the present invention, which correspond to compounds represented by formula (1a):

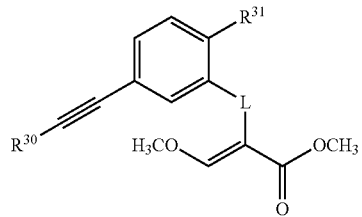

(1a)

wherein the combination of $R^{30}$, $R^{31}$ and L represents the combinations indicated below.

Present compound 76 ($R^{30}$:(CH$_2$)$_2$CH(CH$_3$)$_2$, $R^{31}$:Me, L:O): $^1$H-NMR (CDCl$_3$) δ: 7.32 (1H, s), 7.05 (1H, d), 6.95 (1H, d), 6.74 (1H, s), 3.87 (3H, s), 3.70 (3H, s), 2.38 (2H, t), 2.32 (3H, s), 1.76-1.69 (1H, m), 1.49 (2H, dt), 0.92 (6H, d).

Present compound 77 ($R^{30}$:CH$_2$(c-Hex), $R^{31}$:Me, L:O): $^1$H-NMR (CDCl$_3$) δ: 7.32 (1H, s), 7.05 (1H, d), 6.96 (1H, d), 6.74 (1H, s), 3.87 (3H, s), 3.70 (3H, s), 2.32 (3H, s), 2.26 (2H, d), 1.87-1.83 (2H, m), 1.75-1.65 (3H, m), 1.26-1.14 (6H, m).

Present compound 78 ($R^{30}$:Ph, $R^{31}$:Me, L:O): $^1$H-NMR (CDCl$_3$) δ: 7.53-7.49 (2H, m), 7.36-7.29 (4H, m), 7.14-7.09 (2H, m), 6.88 (1H, d), 3.89 (3H, s), 3.72 (3H, s), 2.37 (3H, s).

Present compound 79 ($R^{30}$:Ph, $R^{31}$:H, L:NMe): $^1$H-NMR (CDCl$_3$) δ: 7.54-7.51 (2H, m), 7.43 (1H, s), 7.36-7.29 (3H, m), 7.16 (1H, t), 6.91 (1H, d), 6.82 (1H, m), 6.63 (1H, dd), 3.89 (3H, d), 3.69 (3H, d), 3.08 (3H, s).

Present compound 80 ($R^{30}$:2-Cl-Ph, $R^{31}$:H, L:NMe): $^1$H-NMR (CDCl$_3$) δ: 7.56 (1H, m), 7.43 (1H, s), 7.44-7.40 (3H, m), 7.17 (1H, t), 6.95 (1H, d), 6.85 (1H, m), 6.65 (1H, dd), 3.88 (3H, s), 3.69 (3H, s), 3.08 (3H, s).

Compound 6 of the present invention ($R^{30}$:c-Pr, $R^{31}$:Me, L:O): $^1$H-NMR (CDCl$_3$) δ: 7.31 (1H, s), 7.04 (1H, d), 6.93 (1H, d), 6.73 (1H, s), 3.87 (3H, s), 3.70 (3H, s), 2.32 (3H, s), 1.45-1.39 (1H, m), 0.87-0.76 (4H, m).

Compound 7 of the present invention ($R^{30}$:c-Pr, $R^{31}$:Cl, L:O): $^1$H-NMR (CDCl$_3$) δ: 7.34 (1H, s), 7.26 (1H, d), 6.95 (1H, dd), 6.81 (1H, d), 3.88 (3H, s), 3.72 (3H, s), 1.46-1.38 (1H, m), 0.91-0.77 (4H, m).

Compound 8 of the present invention ($R^{30}$:c-Pr, $R^{31}$:Me, L:CH$_2$): $^1$H-NMR (CDCl$_3$) δ: 7.48 (1H, s), 7.11-7.07 (2H, m), 7.01 (1H, d), 3.84 (3H, s), 3.67 (3H, s), 3.49 (2H, s), 2.32 (3H, s), 1.47-1.39 (1H, m), 0.87-0.75 (4H, m).

Compound 9 of the present invention ($R^{30}$:c-Pr, $R^{31}$:H, L:NMe): $^1$H-NMR (CDCl$_3$) δ: 7.41 (1H, s), 7.09 (1H, t), 6.76 (1H, d), 6.69 (1H, s), 6.57 (1H, d), 3.88 (3H, s), 3.68 (3H, s), 3.05 (3H, s), 1.49-1.39 (1H, m), 0.95-0.78 (4H, m).

Preparation Example 5

A mixture of methyl (2E)-3-(5-bromo-2-methylphenyl)-2-(methoxyimino)propanate, which was prepared by the method described in WO 2000/041999, 0.40 g, 1-octyne 0.39 mL, PdCl$_2$(Pn$_3$)$_2$ 0.09 g, and copper(I) iodide 0.03 g, triethylamine 4.0 mL, and acetonitrile 6.0 mL was stirred at 75° C. for 3 hours. The resulting mixture was cooled to room temperature, and then concentrated under reduced pressure. The resulting residue was subjected to a silica gel column chromatography (ethyl acetate:hexane=1:9) to obtain the present compound 81 represented by the following formula 0.20 g.

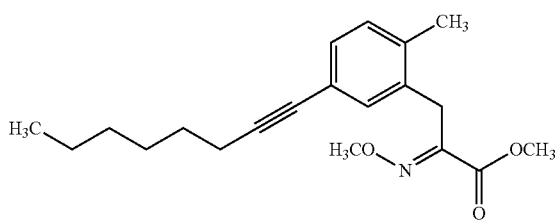 [SMILES: CCCCCCC#Cc1ccc(C)c(C/C(=N\OC)C(=O)OC)c1]

Present compound 81: $^1$H-NMR (CDCl$_3$) δ: 7.17-7.13 (1H, m), 7.07-7.01 (2H, m), 4.08 (3H, s), 3.85 (2H, s), 3.83 (3H, s), 2.37 (2H, t), 2.32 (3H, s), 1.62-1.53 (2H, m), 1.48-1.38 (2H, m), 1.35-1.27 (4H, m), 0.90 (3H, t).

Preparation Example 6

To a mixture of methyl 2-{5-[(1E)-1-(hydroxyimino)ethyl]-2-methylphenoxy}-3-methoxyacrylate, which was prepared by the method described in WO 1998/043949 A1, 0.50 g, and DMF 5.0 mL was added sodium hydride (60%, in oil) 0.10 g, and the mixtures was stirred for 1 hour. To the resulting mixture was added 1,1,1-trifluoro-4-iodobutane 0.36 g, and the mixture was stirred at room temperature for 4 hours. To the resulting mixture were added water, and 1N hydrochloric acid successively, and the mixture was extracted with ethyl acetate. The resulting organic layers were dried over anhydrous sodium sulfate, and concentrated under reduced pressure. The resulting residue was subjected to a silica gel column chromatography (ethyl acetate:hexane=1:4) to obtain the present compound 82 represented by the following formula 0.20 g.

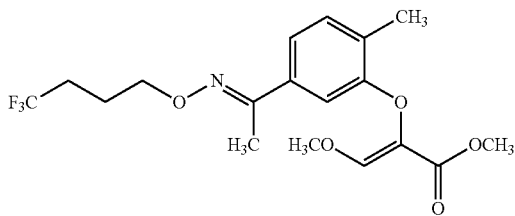 [SMILES: CO/C=C(\Oc1cc(/C(C)=N/OCCCC(F)(F)F)ccc1C)C(=O)OC]

Present compound 82: $^1$H-NMR (CDCl$_3$) δ: 7.33 (1H, s), 7.15 (2H, d), 7.02 (1H, s), 4.12 (2H, t), 3.87 (3H, s), 3.70 (3H, s), 2.35 (3H, s), 2.26-2.15 (2H, m), 2.15 (3H, s), 1.99-1.95 (2H, m).

Preparation Example 6-1

The compounds which were prepared according to the method described in Preparation Example 6 and their physical property values are shown below.

The present compounds 83 to 85, which correspond to the compounds represented by formula (1k) wherein R$^{66}$ represents any substituents indicated below.

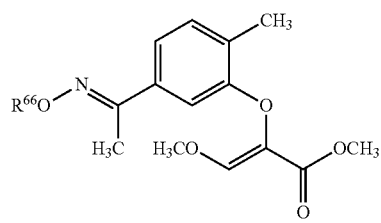

(1k)

Present compound 83 (R$^{66}$:CH$_2$c-Pr): $^1$H-NMR (CDCl$_3$) δ: 7.33 (1H, s), 7.17 (1H, d), 7.14 (1H, d), 7.04 (1H, s), 4.12 (2H, d), 3.87 (3H, s), 3.70 (3H, s), 2.35 (3H, s), 2.18 (3H, s), 1.18 (1H, m), 0.56-0.53 (2H, m), 0.31-0.33 (2H, m).

Present compound 84 (R$^{66}$:CH$_2$c-Bu): $^1$H-NMR (CDCl$_3$) δ: 7.33 (1H, s), 7.17 (1H, d), 7.14 (1H, d), 7.03 (1H, s), 4.13 (2H, d), 3.87 (3H, s), 3.70 (3H, s), 2.69 (1H, m), 2.35 (3H, s), 2.17 (3H, s), 2.09-2.04 (2H, m), 1.91-1.81 (4H, m).

Present compound 85 (R$^{66}$:CH$_2$C≡CEt): $^1$H-NMR (CDCl$_3$) δ: 7.33 (1H, s), 7.17 (1H, d), 7.14 (1H, d), 7.02 (1H, s), 4.75 (2H, s), 3.88 (3H, s), 3.70 (3H, s), 2.35 (3H, s), 2.25 (2H, q), 2.19 (3H, s), 1.16 (3H, t).

Preparation Example 7

A mixture of the intermediate compound 5 0.18 g, O-(isopropyl)hydroxylamino hydrochloride salt 0.12 g, and ethanol 10.0 mL was stirred at 80° C. for 1 hour. To the resulting mixture was added water, and the ethanol was distilled off under reduced pressure. The resulting residue was extracted with ethyl acetate. The resulting organic layers were dried over sodium sulfate, and concentrated under reduced pressure. The resulting residue was subjected to a silica gel column chromatography (ethyl acetate:hexane=1:4) to obtain the present compound 86 represented by the following formula 0.18 g.

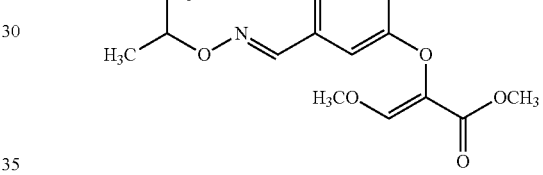

Present compound 86: $^1$H-NMR (CDCl$_3$) δ: 7.94 (1H, s), 7.33 (1H, s), 7.16-7.08 (2H, m), 6.94 (1H, s), 4.47-4.38 (1H, m), 3.87 (3H, s), 3.71 (3H, s), 2.35 (3H, s), 1.27 (6H, d).

Reference Preparation Example 4

A mixture of methyl 2-(5-bromo-2-methylphenoxy)acetate 1.0 g, cyclopropylacetylene 5.0 g, PdCl$_2$(PPh$_3$)$_2$ 0.27 g, copper(I) iodide 0.074 g, triethylamine 5 mL, and acetonitrile 5 mL was stirred at 50° C. for 12 hours and further at 70° C. for 3 hours under nitrogen atmosphere. The resulting mixture was cooled to room temperature, and thereto was then added saturated aqueous sodium hydrocarbonate solution, and the mixture was extracted with ethyl acetate. The resulting organic layers were dried over magnesium sulfate, and concentrated under reduced pressure. The resulting residue was subjected to a silica gel column chromatography (ethyl acetate:hexane=1:9) to obtain the intermediate compound 6 represented by the following formula 0.71 g.

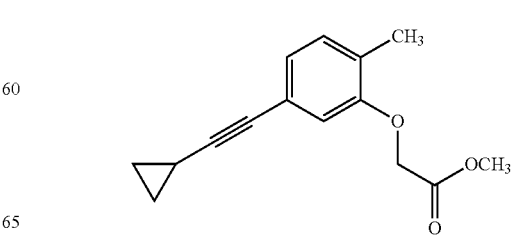

Intermediate compound 6: $^1$H-NMR (CDCl$_3$) δ: 7.04 (1H, d), 6.94 (1H, dd), 6.71 (1H, s), 4.63 (2H, s), 3.80 (3H, s), 2.26 (3H, s), 1.43 (1H, m), 0.91-0.76 (4H, m).

Reference Preparation Example 5

To a mixture of the intermediate compound 6 1.0 g, methyl formate 0.80 g, and dimethoxyethane 10 mL was added potassium tert-butoxide 1.10 g under ice-cooling, and the mixture was stirred at room temperature for 5 hours. To the resulting mixture was added 1N hydrochloric acid, and the mixture was extracted with ethyl acetate. The resulting organic layers were dried over magnesium sulfate, and concentrated under reduced pressure to obtain the intermediate compound 7 represented by the following formula 1.3 g.

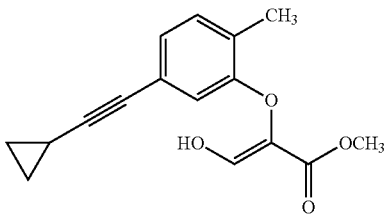 [SMILES: COC(=O)/C(=C/O)Oc1cc(C#CC2CC2)ccc1C]

Intermediate compound 7: $^1$H-NMR (CDCl$_3$) δ: 7.52 (1H, br s), 7.08 (1H, d), 6.98 (1H, dd), 6.75 (1H, d), 5.77 (1H, br s), 3.69 (3H, s), 2.33 (3H, s), 1.42 (1H, m), 0.90-0.76 (4H, m).

Preparation Example 8

To a mixture of the intermediate compound 7 0.74 g, potassium carbonate 0.42 g, and DMF 10 mL was added methyl iodide 0.19 mL, and the mixture was stirred at room temperature for 3 hours. To the resulting mixture was added water, and the mixture was extracted with MTBE. The resulting organic layers were dried over magnesium sulfate, and concentrated under reduced pressure. The resulting residue was subjected to a silica gel column chromatography (ethyl acetate:hexane=1:4) to obtain the Compound 6 of the present invention represented by the following formula 0.22 g.

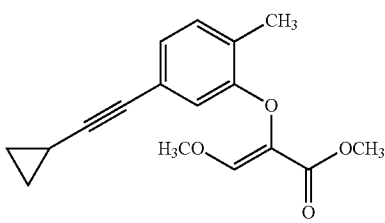 [SMILES: CO/C=C(\Oc1cc(C#CC2CC2)ccc1C)C(=O)OC]

Preparation Example 9

To a mixture of the present compound 7 0.62 g, potassium hydroxide 0.30 g, and methanol 5 mL was added hydroxylamine hydrochloride acid salt 0.23 g, and the mixture was stirred at room temperature for 20 hours. To the resulting mixture was added water, and the mixture was extracted with MTBE. The resulting organic layers were concentrated under reduced pressure. To the resulting residue were added 1,2-dibromoethane 0.20 mL, potassium carbonate 0.47 g, methanol 8 mL, and water 2 mL successively, and the mixture was stirred at room temperature overnight. The resulting mixture was concentrated under reduced pressure, and thereto was added water, and the mixture was extracted with ethyl acetate. The resulting organic layers were dried over magnesium sulfate, and concentrated under reduced pressure. The resulting residue was subjected to a silica gel column chromatography (ethyl acetate:hexane=1:4) to obtain the present compound 98 represented by the following formula 0.01 g.

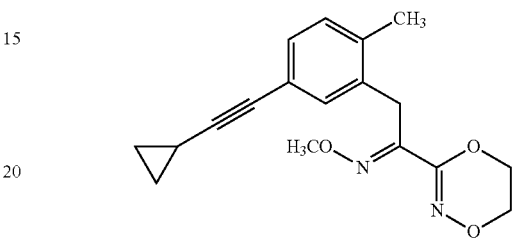

Present compound 98: $^1$H-NMR (CDCl$_3$) δ: 7.13 (1H, dd), 7.05-7.01 (2H, m), 4.45 (2H, t), 4.14 (2H, t), 4.02 (3H, s), 3.83 (2H, s), 2.31 (3H, s), 1.48-1.39 (1H, m), 0.89-0.76 (4H, m).

The present compounds and the compounds of the present invention, which are prepared according to the above-mentioned Process(es) and Preparation Example(s) are shown below.

A compound represented by formula (1A):

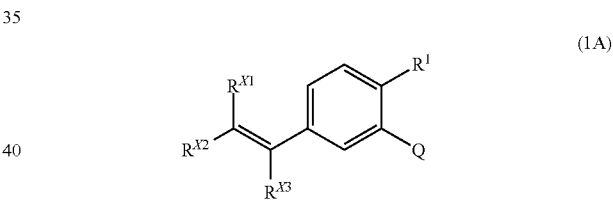

wherein Q represents a group represented by Q1, L represents an oxygen atom, R$^1$ represents a methyl group, and a combination of R$^{x1}$, R$^{x2}$, and R$^{x3}$ represents any combination indicated in the combination A (hereinafter, referred to as Compound Class SX1).

The combination A consists of the substituent number ZA1 to ZA760. The substituent number ZA1 to ZA760 represents any combinations of R$^{x1}$, R$^{x2}$ and R$^{x3}$ in the compound represented formula (1A), and hereinafter, which is indicated as [Substituent Number; R$^{x1}$, R$^{x2}$, R$^{x3}$]. For example, "Substituent Number ZA2" represents a combination where R$^{x2}$ represents an ethyl group, and R$^{x1}$ and R$^{x3}$ each is a hydrogen atom.

Combination A
[ZA1;H,Me,H], [ZA2;H,Et,H], [ZA3;H,Pr,H], [ZA4;H,Bu,H], [ZA5;H,Pen,H], [ZA6;H,Hex,H], [ZA7;H,i-Pr,H], [ZA8;H,i-Bu,H], [ZA9;H,t-Bu,H], [ZA10;H,c-Pr,H], [ZA11;H,c-Bu,H], [ZA12;H,c-Pen,H], [ZA13;H,c-Hex,H], [ZA14;H,CH$_2$c-Pr,H], [ZA15;H,CH$_2$c-Pen,H], [ZA16;H,CH$_2$c-Hex,H], [ZA17;H,CH$_2$Ph,H], [ZA18;H,CH=CH$_2$,H], [ZA19;H,CH(Cl)Me,H], [ZA20;H,CH(Cl)Et,H], [ZA21;H,CH(Cl)Pr,H], [ZA22;H,CH(Cl)i-Pr,H], [ZA23;H,Ph,H], [ZA24;H,2-F-Ph,H], [ZA25;H,3-F-Ph,H], [ZA26;H,4-F-Ph,H], [ZA27;H,2-Cl-Ph,H], [ZA28;H,3-Cl-Ph,H],

[ZA29;H,4-Cl-Ph,H], [ZA30;H,2-Me-Ph,H], [ZA31;H,3-Me-Ph,H], [ZA32;H,4-Me-Ph,H], [ZA33;H,2-OMe-Ph,H], [ZA34;H,3-OMe-Ph,H], [ZA35;H,4-OMe-Ph,H], [ZA36;H,2-Pyridyl,H], [ZA37;H,3-Pyridyl,H], [ZA38;H,4-Pyridyl,H], [ZA39;H,2-Thienyl,H], [ZA40;H,3-Thienyl,H], [ZA41;H,2-pyrimidinyl,H], [ZA42;H,4-pyrimidinyl,H], [ZA43;H,5-pyrimidinyl,H], [ZA44;H,3-pyridazinyl,H], [ZA45;H,4-pyridazinyl,H], [ZA46;H,F,H], [ZA47;H,Cl,H], [ZA48;H,Br,H], [ZA49;H,I,H], [ZA50;H,CN,H], [ZA51;H,$CF_3$,H], [ZA52;Me,H,H], [ZA53;Me,Me,H], [ZA54;Me,Et,H], [ZA55;Me,Pr,H], [ZA56;Me,Bu,H], [ZA57;Me,Pen,H], [ZA58;Me,Hex,H], [ZA59;Me,i-Pr,H], [ZA60;Me,i-Bu,H], [ZA61;Me,t-Bu,H], [ZA62;Me,c-Pr,H], [ZA63;Me,c-Bu,H], [ZA64;Me,c-Pen,H], [ZA65;Me,c-Hex,H], [ZA66;Me,$CH_2$c-Pr,H], [ZA67;Me,$CH_2$c-Pen,H], [ZA68;Me,$CH_2$c-Hex,H], [ZA69;Me,$CH_2$Ph,H], [ZA70;Me,CH=$CH_2$,H], [ZA71;Me,CH(Cl)Me,H], [ZA72;Me,CH(Cl)Et,H], [ZA73;Me,CH(Cl)Pr,H], [ZA74;Me,CH(Cl)i-Pr,H], [ZA75;Me,Ph,H], [ZA76;Me,2-F-Ph,H], [ZA77;Me,3-F-Ph,H], [ZA78;Me,4-F-Ph,H], [ZA79;Me,2-Cl-Ph,H], [ZA80;Me,3-Cl-Ph,H], [ZA81;Me,4-Cl-Ph,H], [ZA82;Me,2-Me-Ph,H], [ZA83;Me,3-Me-Ph,H], [ZA84;Me,4-Me-Ph,H], [ZA85;Me,2-OMe-Ph,H], [ZA86;Me,3-OMe-Ph,H], [ZA87;Me,4-OMe-Ph,H], [ZA88;Me,2-Pyridyl,H], [ZA89;Me,3-Pyridyl,H], [ZA90;Me,4-Pyridyl,H], [ZA91;Me,2-Thienyl,H], [ZA92;Me,3-Thienyl,H], [ZA93;Me,2-pyrimidinyl,H], [ZA94;Me,4-pyrimidinyl,H], [ZA95;Me,5-pyrimidinyl,H], [ZA96;Me,3-pyridazinyl,H], [ZA97;Me,4-pyridazinyl,H], [ZA98;Me,F,H], [ZA99;Me,Cl,H], [ZA100;Me,Br,H], [ZA101;Me,I,H], [ZA102;Me,CN,H], [ZA103;Me,$CF_3$,H], [ZA104;Et,H,H], [ZA105;Et,Me,H], [ZA106;Et,Et,H], [ZA107;Et,Pr,H], [ZA108;Et,Bu,H], [ZA109;Et,Pen,H], [ZA110;Et,Hex,H], [ZA111;Et,i-Pr,H], [ZA112;Et,i-Bu,H], [ZA113;Et,t-Bu,H], [ZA114;Et,c-Pr,H], [ZA115;Et,c-Bu,H], [ZA116;Et,c-Pen,H], [ZA117;Et,c-Hex,H], [ZA118;Et,$CH_2$c-Pr,H], [ZA119;Et,$CH_2$c-Pen,H], [ZA120;Et,$CH_2$c-Hex,H], [ZA121;Et,$CH_2$Ph,H], [ZA122;Et,CH=$CH_2$,H], [ZA123;Et,CH(Cl)Me,H], [ZA124;Et,CH(Cl)Et,H], [ZA125;Et,CH(Cl)Pr,H], [ZA126;Et,CH(Cl)i-Pr,H], [ZA127;Et,Ph,H], [ZA128;Et,2-F-Ph,H], [ZA129;Et,3-F-Ph,H], [ZA130;Et,4-F-Ph,H], [ZA131;Et,2-Cl-Ph,H], [ZA132;Et,3-Cl-Ph,H], [ZA133;Et,4-Cl-Ph,H], [ZA134;Et,2-Me-Ph,H], [ZA135;Et,3-Me-Ph,H], [ZA136;Et,4-Me-Ph,H], [ZA137;Et,2-OMe-Ph,H], [ZA138;Et,3-OMe-Ph,H], [ZA139;Et,4-OMe-Ph,H], [ZA140;Et,2-Pyridyl,H], [ZA141;Et,3-Pyridyl,H], [ZA142;Et,4-Pyridyl,H], [ZA143;Et,2-Thienyl,H], [ZA144;Et,3-Thienyl,H], [ZA145;Et,2-pyrimidinyl,H], [ZA146;Et,4-pyrimidinyl,H], [ZA147;Et,5-pyrimidinyl,H], [ZA148;Et,3-pyridazinyl,H], [ZA149;Et,4-pyridazinyl,H], [ZA150;Et,F,H], [ZA151;Et,Cl,H], [ZA152;Et,Br,H], [ZA153;Et,I,H], [ZA154;Et,CN,H], [ZA155;Et,$CF_3$,H], [ZA156;$CF_3$,H,H], [ZA157;$CF_3$,Me,H], [ZA158;$CF_3$,Et,H], [ZA159;$CF_3$,Pr,H], [ZA160;$CF_3$,Bu,H], [ZA161;$CF_3$,Pen,H], [ZA162;$CF_3$,Hex,H], [ZA163;$CF_3$,i-Pr,H], [ZA164;$CF_3$,i-Bu,H], [ZA165;$CF_3$,t-Bu,H], [ZA166;$CF_3$,c-Pr,H], [ZA167;$CF_3$,c-Bu,H], [ZA168;$CF_3$,c-Pen,H], [ZA169;$CF_3$,c-Hex,H], [ZA170;$CF_3$,$CH_2$c-Pr,H], [ZA171;$CF_3$,$CH_2$c-Pen,H], [ZA172;$CF_3$,$CH_2$c-Hex,H], [ZA173;$CF_3$,$CH_2$Ph,H], [ZA174;$CF_3$,CH=$CH_2$,H], [ZA175;$CF_3$,CH(Cl)Me,H], [ZA176;$CF_3$,CH(Cl)Et,H], [ZA177;$CF_3$,CH(Cl)Pr,H], [ZA178;$CF_3$,CH(Cl)i-Pr,H], [ZA179;$CF_3$,Ph,H], [ZA180;$CF_3$,2-F-Ph,H], [ZA181;$CF_3$,3-F-Ph,H], [ZA182;$CF_3$,4-F-Ph,H], [ZA183;$CF_3$,2-Cl-Ph,H], [ZA184;$CF_3$,3-Cl-Ph,H], [ZA185;$CF_3$,4-Cl-Ph,H], [ZA186;$CF_3$,2-Me-Ph,H], [ZA187;$CF_3$,3-Me-Ph,H], [ZA188;$CF_3$,4-Me-Ph,H], [ZA189;$CF_3$,2-OMe-Ph,H], [ZA190;$CF_3$,3-OMe-Ph,H], [ZA191;$CF_3$,4-OMe-Ph,H], [ZA192;$CF_3$,2-Pyridyl,H], [ZA193;$CF_3$,3-Pyridyl,H], [ZA194;$CF_3$,4-Pyridyl,H], [ZA195;$CF_3$,2-Thienyl,H], [ZA196;$CF_3$,3-Thienyl,H], [ZA197;$CF_3$,2-pyrimidinyl,H], [ZA198;$CF_3$,4-pyrimidinyl,H], [ZA199;$CF_3$,5-pyrimidinyl,H], [ZA200;$CF_3$,3-pyridazinyl,H], [ZA201;$CF_3$,4-pyridazinyl,H], [ZA202;$CF_3$,F,H], [ZA203;$CF_3$,Cl,H], [ZA204;$CF_3$,Br,H], [ZA205;$CF_3$,I,H], [ZA206;$CF_3$,CN,H], [ZA207;$CF_3$,$CF_3$,H], [ZA208;H,Me,Me], [ZA209;H,Et,Me], [ZA210;H,Pr,Me], [ZA211;H,Bu,Me], [ZA212;H,Pen,Me], [ZA213;H,Hex,Me], [ZA214;H,i-Pr,Me], [ZA215;H,i-Bu,Me], [ZA216;H,t-Bu,Me], [ZA217;H,c-Pr,Me], [ZA218;H,c-Bu,Me], [ZA219;H,c-Pen,Me], [ZA220;H,c-Hex,Me], [ZA221;H,$CH_2$c-Pr,Me], [ZA222;H,$CH_2$c-Pen,Me], [ZA223;H,$CH_2$c-Hex,Me], [ZA224;H,$CH_2$Ph,Me], [ZA225;H,CH=$CH_2$,Me], [ZA226;H,CH(Cl)Me,Me], [ZA227;H,CH(Cl)Et,Me], [ZA228;H,CH(Cl)Pr,Me], [ZA229;H,CH(Cl)i-Pr,Me], [ZA230;H,Ph,Me], [ZA231;H,2-F-Ph,Me], [ZA232;H,3-F-Ph,Me], [ZA233;H,4-F-Ph,Me], [ZA234;H,2-Cl-Ph,Me], [ZA235;H,3-Cl-Ph,Me], [ZA236;H,4-Cl-Ph,Me], [ZA237;H,2-Me-Ph,Me], [ZA238;H,3-Me-Ph,Me], [ZA239;H,4-Me-Ph,Me], [ZA240;H,2-OMe-Ph,Me], [ZA241;H,3-OMe-Ph,Me], [ZA242;H,4-OMe-Ph,Me], [ZA243;H,2-Pyridyl,Me], [ZA244;H,3-Pyridyl,Me], [ZA245;H,4-Pyridyl,Me], [ZA246;H,2-Thienyl,Me], [ZA247;H,3-Thienyl,Me], [ZA248;H,2-pyrimidinyl,Me], [ZA249;H,4-pyrimidinyl,Me], [ZA250;H,5-pyrimidinyl,Me], [ZA251;H,3-pyridazinyl,Me], [ZA252;H,4-pyridazinyl,Me], [ZA253;H,F,Me], [ZA254;H,Cl,Me], [ZA255;H,Br,Me], [ZA256;H,I,Me], [ZA257;H,CN,Me], [ZA258;H,$CF_3$,Me], [ZA259;Me,H,Me], [ZA260;Me,Me,Me], [ZA261;Me,Et,Me], [ZA262;Me,Pr,Me], [ZA263;Me,Bu,Me], [ZA264;Me,Pen,Me], [ZA265;Me,Hex,Me], [ZA266;Me,i-Pr,Me], [ZA267;Me,i-Bu,Me], [ZA268;Me,t-Bu,Me], [ZA269;Me,c-Pr,Me], [ZA270;Me,c-Bu,Me], [ZA271;Me,c-Pen,Me], [ZA272;Me,c-Hex,Me], [ZA273;Me,$CH_2$c-Pr,Me], [ZA274;Me,$CH_2$c-Pen,Me], [ZA275;Me,$CH_2$c-Hex,Me], [ZA276;Me,$CH_2$Ph,Me], [ZA277;Me,CH=$CH_2$,Me], [ZA278;Me,CH(Cl)Me,Me], [ZA279;Me,CH(Cl)Et,Me], [ZA280;Me,CH(Cl)Pr,Me], [ZA281;Me,CH(Cl)i-Pr,Me], [ZA282;Me,Ph,Me], [ZA283;Me,2-F-Ph,Me], [ZA284;Me,3-F-Ph,Me], [ZA285;Me,4-F-Ph,Me], [ZA286;Me,2-Cl-Ph,Me], [ZA287;Me,3-Cl-Ph,Me], [ZA288;Me,4-Cl-Ph,Me], [ZA289;Me,2-Me-Ph,Me], [ZA290;Me,3-Me-Ph,Me], [ZA291;Me,4-Me-Ph,Me], [ZA292;Me,2-OMe-Ph,Me], [ZA293;Me,3-OMe-Ph,Me], [ZA294;Me,4-OMe-Ph,Me], [ZA295;Me,2-Pyridyl,Me], [ZA296;Me,3-Pyridyl,Me], [ZA297;Me,4-Pyridyl,Me], [ZA298;Me,2-Thienyl,Me], [ZA299;Me,3-Thienyl,Me], [ZA300;Me,2-pyrimidinyl,Me], [ZA301;Me,4-pyrimidinyl,Me], [ZA302;Me,5-pyrimidinyl,Me], [ZA303;Me,3-pyridazinyl,Me], [ZA304;Me,4-pyridazinyl,Me], [ZA305;Me,F,Me], [ZA306;Me,Cl,Me], [ZA307;Me,Br,Me], [ZA308;Me,I,Me], [ZA309;Me,CN,Me], [ZA310;Me,$CF_3$,Me], [ZA311;Et,H,Me], [ZA312;Et,Me,Me], [ZA313;Et,Et,Me], [ZA314;Et,Pr,Me], [ZA315;Et,Bu,Me], [ZA316;Et,Pen,Me], [ZA317;Et,Hex,Me], [ZA318;Et,i-Pr,Me], [ZA319;Et,i-Bu,Me], [ZA320;Et,t-Bu,Me], [ZA321;Et,c-Pr,Me], [ZA322;Et,c-Bu,Me], [ZA323;Et,c-Pen,Me], [ZA324;Et,c-Hex,Me], [ZA325;Et,$CH_2$c-Pr,Me], [ZA326;Et,$CH_2$c-Pen,Me], [ZA327;Et,$CH_2$c-Hex,Me], [ZA328;Et,$CH_2$Ph,Me], [ZA329;Et,CH=$CH_2$,Me], [ZA330;Et,CH(Cl)Me,Me], [ZA331;Et,CH(Cl)Et,Me], [ZA332;Et,CH(Cl)Pr,Me], [ZA333;Et,CH(Cl)i-Pr,Me], [ZA334;Et,Ph,Me], [ZA335;Et,2-F-Ph,Me], [ZA336;Et,3-F-Ph,Me], [ZA337;Et,4-F-Ph,Me], [ZA338;Et,2-Cl-Ph,Me], [ZA339;Et,3-Cl-Ph,Me], [ZA340;Et,4-Cl-Ph,Me], [ZA341;Et,2-Me-Ph,Me], [ZA342;Et,3-Me-Ph,Me], [ZA343;Et,4-Me-Ph,Me], [ZA344;Et,2-OMe-Ph,Me], [ZA345;Et,3-

OMe-Ph,Me], [ZA346;Et,4-OMe-Ph,Me], [ZA347;Et,2-Pyridyl,Me], [ZA348;Et,3-Pyridyl,Me], [ZA349;Et,4-Pyridyl,Me], [ZA350;Et,2-Thienyl,Me], [ZA351;Et,3-Thienyl,Me], [ZA352;Et,2-pyrimidinyl,Me], [ZA353;Et,4-pyrimidinyl,Me], [ZA354;Et,5-pyrimidinyl,Me], [ZA355;Et,3-pyridazinyl,Me], [ZA356;Et,4-pyridazinyl,Me], [ZA357;Et,F,Me], [ZA358;Et,Cl,Me], [ZA359;Et,Br,Me], [ZA360;Et,I,Me], [ZA361;Et,CN,Me], [ZA362;Et,CF$_3$,Me], [ZA363;CF$_3$,H,Me], [ZA364;CF$_3$,Me,Me], [ZA365;CF$_3$,Et,Me], [ZA366;CF$_3$,Pr,Me], [ZA367;CF$_3$,Bu,Me], [ZA368;CF$_3$,Pen,Me], [ZA369;CF$_3$,Hex,Me], [ZA370;CF$_3$,i-Pr,Me], [ZA371;CF$_3$,i-Bu,Me], [ZA372;CF$_3$,t-Bu,Me], [ZA373;CF$_3$,c-Pr,Me], [ZA374;CF$_3$,c-Bu,Me],[ZA375;CF$_3$,c-Pen,Me], [ZA376;CF$_3$,c-Hex,Me], [ZA377;CF$_3$,CH$_2$c-Pr,Me], [ZA378;CF$_3$,CH$_2$c-Pen,Me], [ZA379;CF$_3$,CH$_2$c-Hex,Me], [ZA380;CF$_3$,CH$_2$Ph,Me], [ZA381;CF$_3$,CH=CH$_2$,Me], [ZA382;CF$_3$,CH(Cl)Me,Me], [ZA383;CF$_3$,CH(Cl)Et,Me], [ZA384;CF$_3$,CH(Cl)Pr,Me], [ZA385;CF$_3$,CH(Cl)i-Pr,Me], [ZA386;CF$_3$,Ph,Me], [ZA387;CF$_3$,2-F-Ph,Me], [ZA388;CF$_3$,3-F-Ph,Me], [ZA389;CF$_3$,4-F-Ph,Me], [ZA390;CF$_3$,2-Cl-Ph,Me], [ZA391;CF$_3$,3-Cl-Ph,Me], [ZA392;CF$_3$,4-Cl-Ph,Me], [ZA393;CF$_3$,2-Me-Ph,Me], [ZA394;CF$_3$,3-Me-Ph,Me], [ZA395;CF$_3$,4-Me-Ph,Me], [ZA396;CF$_3$,2-OMe-Ph,Me], [ZA397;CF$_3$,3-OMe-Ph,Me], [ZA398;CF$_3$,4-OMe-Ph,Me], [ZA399;CF$_3$,2-Pyridyl,Me], [ZA400;CF$_3$,3-Pyridyl,Me], [ZA401;CF$_3$,4-Pyridyl,Me], [ZA402;CF$_3$,2-Thienyl,Me], [ZA403;CF$_3$,3-Thienyl,Me], [ZA404;CF$_3$,2-pyrimidinyl,Me], [ZA405;CF$_3$,4-pyrimidinyl,Me], [ZA406;CF$_3$,5-pyrimidinyl,Me], [ZA407;CF$_3$,3-pyridazinyl,Me], [ZA408;CF$_3$,4-pyridazinyl,Me], [ZA409;CF$_3$,F,Me], [ZA410;CF$_3$,Cl,Me], [ZA411;CF$_3$,Br,Me], [ZA412;CF$_3$,I,Me], [ZA413;CF$_3$,CN,Me], [ZA414;CF$_3$,CF$_3$,Me], [ZA415;H,Me,Et], [ZA416;H,Et,Et], [ZA417;H,Pr,Et], [ZA418;H,Bu,Et], [ZA419;H,Pen,Et], [ZA420;H,Hex,Et], [ZA421;H,i-Pr,Et], [ZA422;H,i-Bu,Et], [ZA423;H,t-Bu,Et], [ZA424;H,c-Pr,Et], [ZA425;H,c-Bu,Et], [ZA426;H,c-Pen,Et], [ZA427;H,c-Hex,Et], [ZA428;H,CH$_2$c-Pr,Et], [ZA429;H,CH$_2$c-Pen,Et], [ZA430;H,CH$_2$c-Hex,Et], [ZA431;H,CH$_2$Ph,Et], [ZA432;H,CH=CH$_2$,Et], [ZA433;H,CH(Cl)Me,Et], [ZA434;H,CH(Cl)Et,Et], [ZA435;H,CH(Cl)Pr,Et], [ZA436;H,CH(Cl)i-Pr,Et], [ZA437;H,Ph,Et], [ZA438;H,2-F-Ph,Et], [ZA439;H,3-F-Ph,Et], [ZA440;H,4-F-Ph,Et], [ZA441;H,2-Cl-Ph,Et], [ZA442;H,3-Cl-Ph,Et], [ZA443;H,4-Cl-Ph,Et], [ZA444;H,2-Me-Ph,Et], [ZA445;H,3-Me-Ph,Et], [ZA446;H,4-Me-Ph,Et], [ZA447;H,2-OMe-Ph,Et], [ZA448;H,3-OMe-Ph,Et], [ZA449;H,4-OMe-Ph,Et], [ZA450;H,2-Pyridyl,Et], [ZA451;H,3-Pyridyl,Et], [ZA452;H,4-Pyridyl,Et], [ZA453;H,2-Thienyl,Et], [ZA454;H,3-Thienyl,Et], [ZA455;H,2-pyrimidinyl,Et], [ZA456;H,4-pyrimidinyl,Et], [ZA457;H,5-pyrimidinyl,Et], [ZA458;H,3-pyridazinyl,Et], [ZA459;H,4-pyridazinyl,Et], [ZA460;H,F,Et], [ZA461;H,Cl,Et], [ZA462;H,Br,Et], [ZA463;H,I,Et], [ZA464;H,CN,Et], [ZA465;H,CF$_3$,Et], [ZA466;Me,H,Et], [ZA467;Me,Me,Et], [ZA468;Me,Et,Et], [ZA469;Me,Pr,Et], [ZA470;Me,Bu,Et], [ZA471;Me,Pen,Et], [ZA472;Me,Hex,Et], [ZA473;Me,i-Pr,Et], [ZA474;Me,i-Bu,Et], [ZA475;Me,t-Bu,Et], [ZA476;Me,c-Pr,Et], [ZA477;Me,c-Bu,Et], [ZA478;Me,c-Pen,Et], [ZA479;Me,c-Hex,Et], [ZA480;Me,CH$_2$c-Pr,Et], [ZA481;Me,CH$_2$c-Pen,Et], [ZA482;Me,CH$_2$c-Hex,Et], [ZA483;Me,CH$_2$Ph,Et], [ZA484;Me,CH=CH$_2$,Et], [ZA485;Me,CH(Cl)Me,Et], [ZA486;Me,CH(Cl)Et,Et], [ZA487;Me,CH(Cl)Pr,Et], [ZA488;Me,CH(Cl)i-Pr,Et], [ZA489;Me,Ph,Et], [ZA490;Me,2-F-Ph,Et], [ZA491;Me,3-F-Ph,Et], [ZA492;Me,4-F-Ph,Et], [ZA493;Me,2-Cl-Ph,Et], [ZA494;Me,3-Cl-Ph,Et], [ZA495;Me,4-Cl-Ph,Et], [ZA496;Me,2-Me-Ph,Et], [ZA497;Me,3-Me-Ph,Et], [ZA498;Me,4-Me-Ph,Et], [ZA499;Me,2-OMe-Ph,Et], [ZA500;Me,3-OMe-Ph,Et], [ZA501;Me,4-OMe-Ph,Et], [ZA502;Me,2-Pyridyl,Et], [ZA503;Me,3-Pyridyl,Et], [ZA504;Me,4-Pyridyl,Et], [ZA505;Me,2-Thienyl,Et], [ZA506;Me,3-Thienyl,Et], [ZA507;Me,2-pyrimidinyl,Et], [ZA508;Me,4-pyrimidinyl,Et], [ZA509;Me,5-pyrimidinyl,Et], [ZA510;Me,3-pyridazinyl,Et], [ZA511;Me,4-pyridazinyl,Et], [ZA512;Me,F,Et], [ZA513;Me,Cl,Et], [ZA514;Me,Br,Et], [ZA515;Me,I,Et], [ZA516;Me,CN,Et], [ZA517;Me,CF$_3$,Et], [ZA518;Et,H,Et], [ZA519;Et,Me,Et], [ZA520;Et,Et,Et], [ZA521;Et,Pr,Et], [ZA522;Et,Bu,Et], [ZA523;Et,Pen,Et], [ZA524;Et,Hex,Et], [ZA525;Et,i-Pr,Et], [ZA526;Et,i-Bu,Et], [ZA527;Et,t-Bu,Et], [ZA528;Et,c-Pr,Et], [ZA529;Et,c-Bu,Et], [ZA530;Et,c-Pen,Et], [ZA531;Et,c-Hex,Et], [ZA532;Et,CH$_2$c-Pr,Et], [ZA533;Et,CH$_2$c-Pen,Et], [ZA534;Et,CH$_2$c-Hex,Et], [ZA535;Et,CH$_2$Ph,Et], [ZA536;Et,CH=CH$_2$,Et], [ZA537;Et,CH(Cl)Me,Et], [ZA538;Et,CH(Cl)Et,Et], [ZA539;Et,CH(Cl)Pr,Et], [ZA540;Et,CH(Cl)i-Pr,Et], [ZA541;Et,Ph,Et], [ZA542;Et,2-F-Ph,Et], [ZA543;Et,3-F-Ph,Et], [ZA544;Et,4-F-Ph,Et], [ZA545;Et,2-Cl-Ph,Et], [ZA546;Et,3-Cl-Ph,Et], [ZA547;Et,4-Cl-Ph,Et], [ZA548;Et,2-Me-Ph,Et], [ZA549;Et,3-Me-Ph,Et], [ZA550;Et,4-Me-Ph,Et], [ZA551;Et,2-OMe-Ph,Et], [ZA552;Et,3-OMe-Ph,Et], [ZA553;Et,4-OMe-Ph,Et], [ZA554;Et,2-Pyridyl,Et], [ZA555;Et,3-Pyridyl,Et], [ZA556;Et,4-Pyridyl,Et], [ZA557;Et,2-Thienyl,Et], [ZA558;Et,3-Thienyl,Et], [ZA559;Et,2-pyrimidinyl,Et], [ZA560;Et,4-pyrimidinyl,Et], [ZA561;Et,5-pyrimidinyl,Et], [ZA562;Et,3-pyridazinyl,Et], [ZA563;Et,4-pyridazinyl,Et], [ZA564;Et,F,Et], [ZA565;Et,Cl,Et], [ZA566;Et,Br,Et], [ZA567;Et,I,Et], [ZA568;Et,CN,Et], [ZA569;Et,CF$_3$,Et], [ZA570;CF$_3$,H,Et], [ZA571;CF$_3$,Me,Et], [ZA572;CF$_3$,Et,Et], [ZA573;CF$_3$,Pr,Et], [ZA574;CF$_3$,Bu,Et], [ZA575;CF$_3$,Pen,Et], [ZA576;CF$_3$,Hex,Et], [ZA577;CF$_3$,i-Pr,Et], [ZA578;CF$_3$,i-Bu,Et], [ZA579;CF$_3$,t-Bu,Et], [ZA580;CF$_3$,c-Pr,Et], [ZA581;CF$_3$,c-Bu,Et], [ZA582;CF$_3$,c-Pen,Et], [ZA583;CF$_3$,c-Hex,Et], [ZA584;CF$_3$,CH$_2$c-Pr,Et], [ZA585;CF$_3$,CH$_2$c-Pen,Et], [ZA586;CF$_3$,CH$_2$c-Hex,Et], [ZA587;CF$_3$,CH$_2$Ph,Et], [ZA588;CF$_3$,CH=CH$_2$,Et], [ZA589;CF$_3$,CH(Cl)Me,Et], [ZA590;CF$_3$,CH(Cl)Et,Et], [ZA591;CF$_3$,CH(Cl)Pr,Et], [ZA592;CF$_3$,CH(Cl)i-Pr,Et], [ZA593;CF$_3$,Ph,Et], [ZA594;CF$_3$,2-F-Ph,Et], [ZA595;CF$_3$,3-F-Ph,Et], [ZA596;CF$_3$,4-F-Ph,Et], [ZA597;CF$_3$,2-Cl-Ph,Et], [ZA598;CF$_3$,3-Cl-Ph,Et], [ZA599;CF$_3$,4-Cl-Ph,Et], [ZA600;CF$_3$,2-Me-Ph,Et], [ZA601;CF$_3$,3-Me-Ph,Et], [ZA602;CF$_3$,4-Me-Ph,Et], [ZA603;CF$_3$,2-OMe-Ph,Et], [ZA604;CF$_3$,3-OMe-Ph,Et], [ZA605;CF$_3$,4-OMe-Ph,Et], [ZA606;CF$_3$,2-Pyridyl,Et], [ZA607;CF$_3$,3-Pyridyl,Et], [ZA608;CF$_3$,4-Pyridyl,Et], [ZA609;CF$_3$,2-Thienyl,Et], [ZA610;CF$_3$,3-Thienyl,Et], [ZA611;CF$_3$,2-pyrimidinyl,Et], [ZA612;CF$_3$,4-pyrimidinyl,Et], [ZA613;CF$_3$,5-pyrimidinyl,Et], [ZA614;CF$_3$,3-pyridazinyl,Et], [ZA615;CF$_3$,4-pyridazinyl,Et], [ZA616;CF$_3$,F,Et], [ZA617;CF$_3$,Cl,Et], [ZA618;CF$_3$,Br,Et], [ZA619;CF$_3$,I,Et], [ZA620;CF$_3$,CN,Et], [ZA621;CF$_3$,CF$_3$,Et], [ZA622;H,H,F], [ZA623;Me,Me,F], [ZA624;F,F,F], [ZA625;Cl,Cl,F], [ZA626;H,Me,F], [ZA627;H,Et,F], [ZA628;H,Pr,F], [ZA629;H,i-Pr,F], [ZA630;H,c-Pr,F], [ZA631;H,Bu,F], [ZA632;H,i-Bu,F], [ZA633;H,t-Bu,F], [ZA634;H,Pen,F], [ZA635;H,Hex,F], [ZA636;H,F,F], [ZA637;H,Cl,F], [ZA638;H,Br,F], [ZA639;H,I,F], [ZA640;H,Ph,F], [ZA641;Me,H,F], [ZA642;Et,H,F], [ZA643;Pr,H,F], [ZA644;i-Pr,H,F], [ZA645;c-Pr,H,F], [ZA646;Bu,H,F], [ZA647;i-Bu,H,F], [ZA648;t-Bu,H,F], [ZA649;Pen,H,F], [ZA650;Hex,H,F], [ZA651;F,H,F], [ZA652;Cl,H,F], [ZA653;Br,H,F], [ZA654;I,H,F], [ZA655;Ph,H,F], [ZA656;H,H,Cl], [ZA657;Me,Me,Cl], [ZA658;F,F,Cl], [ZA659;Cl,Cl,Cl], [ZA660;H,Me,Cl], [ZA661;H,Et,Cl], [ZA662;H,Pr,Cl], [ZA663;H,i-Pr,Cl], [ZA664;H,c-Pr,Cl], [ZA665;H,Bu,Cl], [ZA666;H,i-Bu,Cl], [ZA667;H,t-Bu, Cl], [ZA668;H,Pen,Cl], [ZA669;H,Hex,Cl], [ZA670;H,F, Cl], [ZA671;H,Cl,Cl], [ZA672;H,Br,Cl], [ZA673;H,I,Cl], [ZA674;H,Ph,Cl], [ZA675;Me,H,Cl], [ZA676;Et,H,Cl], [ZA677;Pr,H,Cl], [ZA678;i-Pr,H,Cl], [ZA679;c-Pr,H,Cl], [ZA680;Bu,H,Cl], [ZA681;i-Bu,H,Cl], [ZA682;t-Bu,H,Cl], [ZA683;Pen,H,Cl], [ZA684;Hex,H,Cl], [ZA685;F,H,Cl], [ZA686;Cl,H,Cl], [ZA687;Br,H,Cl], [ZA688;I,H,Cl], [ZA689;Ph,H,Cl], [ZA690;H,H,Br], [ZA691;Me,Me,Br], [ZA692;F,F,Br], [ZA693;Cl,Cl,Br], [ZA694;H,Me,Br], [ZA695;H,Et,Br], [ZA696;H,Pr,Br], [ZA697;H,i-Pr,Br], [ZA698;H,c-Pr,Br], [ZA699;H,Bu,Br], [ZA700;H,i-Bu,Br], [ZA701;H,t-Bu,Br], [ZA702;H,Pen,Br], [ZA703;H,Hex, Br], [ZA704;H,F,Br], [ZA705;H,Cl,Br], [ZA706;H,Br,Br], [ZA707;H,I,Br], [ZA708;H,Ph,Br], [ZA709;Me,H,Br], [ZA710;Et,H,Br], [ZA711;Pr,H,Br], [ZA712;i-Pr,H,Br], [ZA713;c-Pr,H,Br], [ZA714;Bu,H,Br], [ZA715;i-Bu,H,Br], [ZA716;t-Bu,H,Br], [ZA717;Pen,H,Br], [ZA718;Hex,H, Br], [ZA719;F,H,Br], [ZA720;Cl,H,Br], [ZA721;Br,H,Br], [ZA722;I,H,Br], [ZA723;Ph,H,Br], [ZA724;H,H,CN], [ZA725;Me,Me,CN], [ZA726;Cl,Cl,CN], [ZA727;CN,CN, CN], [ZA728;H$_2$OMe,CN], [ZA729;H$_2$OEt,CN], [ZA730; H$_2$OPr,CN], [ZA731;H,Me,CN], [ZA732;H,Et,CN], [ZA733;H,Pr,CN], [ZA734;H,i-Pr,CN], [ZA735;H,c-Pr, CN], [ZA736;H,Bu,CN], [ZA737;H,i-Bu,CN], [ZA738;H,t-Bu,CN], [ZA739;H,Pen,CN], [ZA740;H,Hex,CN], [ZA741; H,F,CN], [ZA742;H,Cl,CN], [ZA743;H,Br,CN], [ZA744;H, I,CN], [ZA745;H,Ph,CN], [ZA746;Me,H,CN], [ZA747;Et, H,CN], [ZA748;Pr,H,CN], [ZA749;i-Pr,H,CN], [ZA750;c-Pr,H,CN], [ZA751;Bu,H,CN], [ZA752;i-Bu,H,CN], [ZA753;t-Bu,H,CN], [ZA754;Pen,H,CN], [ZA755;Hex,H, CN], [ZA756;F,H,CN], [ZA757;Cl,H,CN], [ZA758;Br,H, CN], [ZA759;I,H,CN], [ZA760;Ph,H,CN], A compound represented by formula (1A) wherein Q represents Q1, L represents an oxygen atom, $R^1$ represents a chlorine atom, and a combination of $R^{x1}$, $R^{x2}$ and $R^{x3}$ represents any combination indicated in the combination A (hereinafter, referred to as Compound Class SX2).

A compound represented by formula (1A) wherein Q represents Q1, L represents CH$_2$, $R^1$ represents a methyl group, and a combination of $R^{x1}$, $R^{x2}$ and $R^{x3}$ represents any combination indicated in the combination A (hereinafter, referred to as Compound Class SX3).

A compound represented by formula (1A) wherein Q represents Q1, L represents CH$_2$, $R^1$ represents a chlorine atom, and a combination of $R^{x1}$, $R^{x2}$ and $R^{x3}$ represents any combination indicated in the combination A (hereinafter, referred to as Compound Class SX4).

A compound represented by formula (1A) wherein Q represents Q1, L represents NCH$_3$, $R^1$ represents a hydrogen atom, and a combination of $R^{x1}$, $R^{x2}$ and $R^{x3}$ represents any combination indicated in the combination A (hereinafter, referred to as Compound Class SX5).

A compound represented by formula (1A) wherein Q represents Q2, X represents an oxygen atom, $R^1$ represents a methyl group, and a combination of $R^{x1}$, $R^{x2}$ and $R^{x3}$ represents any combination indicated in the combination A (hereinafter, referred to as Compound Class SX6).

A compound represented by formula (1A) wherein Q represents Q2, X represents an oxygen atom, $R^1$ represents a chlorine atom, and a combination of $R^{x1}$, $R^{x2}$ and $R^{x3}$ represents any combination indicated in the combination A (hereinafter, referred to as Compound Class SX7).

A compound represented by formula (1A) wherein Q represents Q2, X represents NH, $R^1$ represents a methyl group, and a combination of $R^{x1}$, $R^{x2}$ and $R^{x3}$ represents any combination indicated in the combination A (hereinafter, referred to as Compound Class SX8).

A compound represented by formula (1A) wherein Q represents Q2, X represents NH, $R^1$ represents a chlorine atom, and a combination of $R^{x1}$, $R^{x2}$ and $R^{x3}$ represents any combination indicated in the combination A (hereinafter, referred to as Compound Class SX9).

A compound represented by formula (1A) wherein Q represents Q3, $R^3$ represents a difluoromethyl group, $R^1$ represents a methyl group, and a combination of $R^{x1}$, $R^{x2}$ and $R^{x3}$ represents any combination indicated in the combination A (hereinafter, referred to as Compound Class SX10).

A compound represented by formula (1A) wherein Q represents Q3, $R^3$ represents a difluoromethyl group, $R^1$ represents a chlorine atom, and a combination of $R^{x1}$, $R^{x2}$ and $R^{x3}$ represents any combination indicated in the combination A (hereinafter, referred to as Compound Class SX11).

A compound represented by formula (1A) wherein Q represents Q3, $R^3$ represents a methoxy group, $R^1$ represents a methyl group, and a combination of $R^{x1}$, $R^{x2}$ and $R^{x3}$ represents any combination indicated in the combination A (hereinafter, referred to as Compound Class SX12).

A compound represented by formula (1A) wherein Q represents Q3, $R^3$ represents a methoxy group, $R^1$ represents a chlorine atom, and a combination of $R^{x1}$, $R^{x2}$ and $R^{x3}$ represents any combination indicated in the combination A (hereinafter, referred to as Compound Class SX13).

A compound represented by formula (1A) wherein Q represents Q4, $R^1$ represents a methyl group, and a combination of $R^{x1}$, $R^{x2}$ and $R^{x3}$ represents any combination indicated in the combination A (hereinafter, referred to as Compound Class SX14).

A compound represented by formula (1A) wherein Q represents Q4, $R^1$ represents a chlorine atom, and a combination of $R^{x1}$, $R^{x2}$ and $R^{x3}$ represents any combination indicated in the combination A (hereinafter, referred to as Compound Class SX15).

A compound represented by formula (1B):

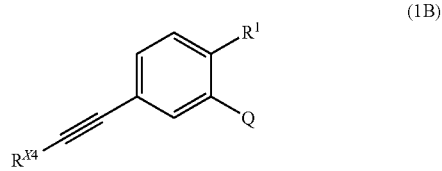

(1B)

wherein Q represents a group represented by Q1, L represents an oxygen atom, $R^1$ represents a methyl group, and $R^{x4}$ represents any substituent selected from Group Z (hereinafter, referred to as Compound Class SX16).

Group Z: a group consisting of Me, Et, Pr, Bu, Pen, Hex, i-Pr, i-Bu, t-Bu, c-Pr, c-Bu, c-Pen, c-Hex, 1-OH-c-Pen, 1-OH-c-Hex, 1-OMe-c-Pen, 1-OMe-c-Hex, CH$_2$c-Pr, CH$_2$c-Pen, CH$_2$c-Hex, CH$_2$Ph, CH═CH$_2$, CH(Et)$_2$, CH(OH)Me, CH(OH)Et, CH(OH)Pr, CH(OH)i-Pr, CH(OH) Bu, CH(OH) i-Bu, CH(OH)Ph, CH(OMe)Me, CH(OMe)Et, CH(OMe)Pr, CH(OMe)i-Pr, CH(OMe)Bu, CH(OMe)i-Bu, CH(OMe)Ph, CH(OEt)Me, CH(Cl)Me, CH(Cl) Et, CH(Cl) Pr, CH(Cl)i-Pr, C(Me)═CH$_2$, C(Me)═CHMe, C(Me)═CMe$_2$, C(Me)$_2$OH, C(Me)$_2$OMe, C(Me)$_2$OEt, C(Me)$_2$OPr, C(Me)$_2$Oi-Pr, C(Me)$_2$Ot-Bu, C(Me)$_2$OPen, C(Me)$_2$OCH$_2$CH═CH$_2$, C(Me))$_2$OCH$_2$C≡CH, C(Me)$_2$OCH$_2$CH═CMe$_2$, C(Me)$_2$OCH$_2$CH═CHMe, C(Me)$_2$OCH$_2$C(Me)═CH$_2$, C(Me)$_2$OCH$_2$Ph, C(Me)$_2$OC(O)Me, C(Me)$_2$O(4-Cl-Ph), C(Me)$_2$Et, C(Me)$_2$Pr, C(Me)$_2$Bu, C(Me)$_2$Ph, C(Me)$_2$ (4-Cl-Ph), C(Me)₂ (3,4-Cl₂-Ph), C(Me)(Et)OH, C(Me)(Et)OMe, C(Me)(Et)OEt, C(Me)(Et)OPr, C(Me)(Et)Oi-Pr, C(Me)(Et)OBu, C(Me)(Et)Ot-Bu, C(Me)(Et)OCH₂CH=CH₂, C(Me)(Et)Ph, C(Me)(i-Pr)OMe, C(Me)(i-Pr)OEt, C(Me)(i-Pr)OPr, C(Me)(i-Pr)OBu, C(Me)(i-Pr)Ot-Bu, C(Me)(i-Pr)OCH₂CH=CH₂, C(Me)(i-Bu)OMe, C(Me)(i-Bu)OEt, C(Me)(i-Bu)OPr, C(Me)(i-Bu)OBu, C(Me)(i-Bu)Ot-Bu, C(Me)(i-Bu)OCH₂CH=CH₂, C(Me)(CF₃)F, C(Me)(CF₃)OMe, C(Me)(CF₃)OEt, C(Me)(CF₃)OPr, C(Me)(CF₃)Oi-Pr, C(Me)(CF₃)OBu, C(Me)(CF₃)Ot-Bu, C(Me)(CF₃)OCH₂CH=CH₂, C(Et)=CH₂, C(Et)=CHMe, C(Et)=CMe₂, C(Et)₂F, C(Et)₂Me, C(Et)₂Pr, C(Et)₂Ph, C(Et)₂OH, C(Et)₂OEt, C(Et)₂OPr, C(Et)₂OBu, C(Et)₂Ot-Bu, CEt₃, C(CF₃)=CH₂, C(CF₃)=CHMe, C(CF₃)=CMe₂, C(F)=CH(F) CF₃, CH₂F, CHF₂, CF(Et)₂, CF(Me)i-Pr, SiMe₃, Si(Me)₂Et, Si(Me)₂Pr, Si(Me)₂Bu, Si(Me)₂Ph, Si(Me)₂t-Bu, Ph, 2-F-Ph, 3-F-Ph, 4-F-Ph, 2-Cl-Ph, 3-Cl-Ph, 4-Cl-Ph, 2-Me-Ph, 3-Me-Ph, 4-Me-Ph, 2-OMe-Ph, 3-OMe-Ph, 4-OMe-Ph, 2-Pyridyl, 3-Pyridyl, 4-Pyridyl, 2-Thienyl, 3-Thienyl, 2-pyrimidinyl, 4-pyrimidinyl, 5-pyrimidinyl, 3-pyridazinyl, and 4-pyridazinyl.

A compound represented by formula (1B) wherein Q represents a group represented by Q1, L represents an oxygen atom, $R^1$ represents a chlorine atom, and $R^{x4}$ represents any substituent selected from Group Z (hereinafter, referred to as Compound Class SX17).

A compound represented by formula (1B) wherein Q represents a group represented by Q1, L represents CH₂, $R^1$ represents a methyl group, and $R^{x4}$ represents any substituent selected from Group Z (hereinafter, referred to as Compound Class SX18).

A compound represented by formula (1B) wherein Q represents a group represented by Q1, L represents CH₂, $R^1$ represents a chlorine atom, and $R^{x4}$ represents any substituent selected from Group Z (hereinafter, referred to as Compound Class SX19).

A compound represented by formula (1B) wherein Q represents a group represented by Q1, L represents NCH₃, $R^1$ represents a hydrogen atom, and $R^{x4}$ represents any substituent selected from Group Z (hereinafter, referred to as Compound Class SX20).

A compound represented by formula (1B) wherein Q represents a group represented by Q2, X represents an oxygen atom, $R^1$ represents a methyl group, and $R^{x4}$ represents any substituent selected from Group Z (hereinafter, referred to as Compound Class SX21).

A compound represented by formula (1B) wherein Q represents a group represented by Q2, X represents an oxygen atom, $R^1$ represents a chlorine atom, and $R^{x4}$ represents any substituent selected from Group Z (hereinafter, referred to as Compound Class SX22).

A compound represented by formula (1B) wherein Q represents a group represented by Q2, X represents NH, $R^1$ represents a methyl group, and $R^{x4}$ represents any substituent selected from Group Z (hereinafter, referred to as Compound Class SX23).

A compound represented by formula (1B) wherein Q represents a group represented by Q2, X represents NH, $R^1$ represents a chlorine atom, and $R^{x4}$ represents any substituent selected from Group Z (hereinafter, referred to as Compound Class SX24).

A compound represented by formula (1B) wherein Q represents a group represented by Q3, $R^3$ represents a difluoromethyl group, $R^1$ represents a methyl group, and $R^{x4}$ represents any substituent selected from Group Z (hereinafter, referred to as Compound Class SX25).

A compound represented by formula (1B) wherein Q represents a group represented by Q3, $R^3$ represents a difluoromethyl group, $R^1$ represents a chlorine atom, and $R^{x4}$ represents any substituent selected from Group Z (hereinafter, referred to as Compound Class SX26).

A compound represented by formula (1B) wherein Q represents a group represented by Q3, $R^3$ represents a methoxy group, $R^1$ represents a methyl group, and $R^{x4}$ represents any substituent selected from Group Z (hereinafter, referred to as Compound Class SX27).

A compound represented by formula (1B) wherein Q represents a group represented by Q3, $R^3$ represents a methoxy group, $R^1$ represents a chlorine atom, and $R^{x4}$ represents any substituent selected from Group Z (hereinafter, referred to as Compound Class SX28).

A compound represented by formula (1B) wherein Q represents a group represented by Q4, $R^1$ represents a methyl group, and $R^{x4}$ represents any substituent selected from Group Z (hereinafter, referred to as Compound Class SX29).

A compound represented by formula (1B) wherein Q represents a group represented by Q4, $R^1$ represents a chlorine atom, and $R^{x4}$ represents any substituent selected from Group Z (hereinafter, referred to as Compound Class SX30).

A compound represented by formula (1C):

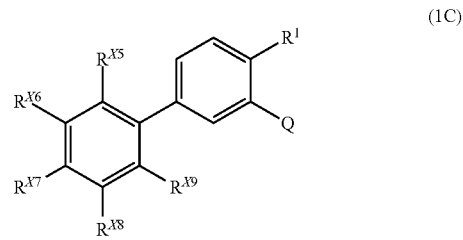

(1C)

wherein Q represents a group represented by Q1, L represents an oxygen atom, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX31).

The combination C consists of the substituent number ZC1 to ZC311. The substituent number ZC1 to ZC311 represents any combinations of $R^{x5}$, $R^{x6}$, $R^{x6}$, $R^{x7}$, $R^{x8}$ and $R^{x9}$ in the compound represented formula (1C), and hereinafter, which is indicated as [Substituent Number: $R^{x5}$; $R^{x6}$; $R^{x7}$; $R^{x8}$; $R^{x9}$]. For example, "Substituent Number ZC2" represents a combination where $R^{x5}$ represents a methyl group, and $R^{x6}$, $R^{x7}$, $R^{x8}$, and $R^{x9}$ each is a hydrogen atom.
Combination C
[ZC1;H,H,H,H,H], [ZC2;Me,H,H,H,H], [ZC3;F,H,H,H,H], [ZC4;Cl,H,H,H,H], [ZC5;OMe,H,H,H,H], [ZC6;CF₃,H,H,H,H], [ZC7;H,Me,H,H,H], [ZC8;H,Et,H,H,H], [ZC9;H,Pr,H,H,H], [ZC10;H,i-Pr,H,H,H], [ZC11;H,t-Bu,H,H,H], [ZC12;H₂OMe,H,H,H], [ZC13;H₂OEt,H,H,H], [ZC14;H₂OPr,H,H,H], [ZC15;H₂Oi-Pr,H,H,H], [ZC16;H,CF₃,H,H,H], [ZC17;H,CF₂H,H,H,H], [ZC18;H,CFH₂,H,H,H], [ZC19;H,F,H,H,H], [ZC20;H,Cl,H,H,H], [ZC21;H,Br,H,H,H], [ZC22;H,CN,H,H,H], [ZC23;H,Ph,H,H,H], [ZC24;H₂OPh,H,H,H], [ZC25;H,c-Pr,H,H,H], [ZC26;H,c-Pen,H,H,H], [ZC27;H,c-Hex,H,H,H], [ZC28;H,H,Me,H,H], [ZC29;H,H,Et,H,H], [ZC30;H,H,Pr,H,H], [ZC31;H,H,i-Pr,H,H], [ZC32;H,H,t-Bu,H,H], [ZC33;H,H₂OMe,H,H], [ZC34;H,H₂OEt,H,H], [ZC35;H,H₂OPr,H,H], [ZC36;H,H₂Oi-Pr,H,H], [ZC37;H,H,CF₃,H,H], [ZC38;H,H,CF₂H,H, H], [ZC39;H,H,CFH₂,H,H], [ZC40;H,H,F,H,H], [ZC41;H,H,Cl,H,H], [ZC42;H,H,Br,H,H], [ZC43;H,H,CN,H,H], [ZC44;H,H,Ph,H,H], [ZC45;H,H₂OPh,H,H], [ZC46;H,H,c-Pr,H,H], [ZC47;H,H,c-Pen,H,H], [ZC48;H,H,c-Hex,H,H], [ZC49;H,H,H,H,F], [ZC50;Me,H,H,H,F], [ZC51;F,H,H,H,F], [ZC52;Cl,H,H,H,F], [ZC53;H,Me,H,H,F], [ZC54;H,Et,H,H,F], [ZC55;H,Pr,H,H,F], [ZC56;H,i-Pr,H,H,F], [ZC57;H,t-Bu,H,H,F], [ZC58;H₂OMe,H,H,F], [ZC59;H₂OEt,H,H,F], [ZC60;H₂OPr,H,H,F], [ZC61;H₂Oi-Pr,H,H,F], [ZC62;H,CF₃,H,H,F], [ZC63;H,CF₂H,H,H,F], [ZC64;H,CFH₂,H,H,F], [ZC65;H,F,H,H,F], [ZC66;H,Cl,H,H,F], [ZC67;H,Br,H,H,F], [ZC68;H,CN,H,H,F], [ZC69;H,Ph,H,H,F],[ZC70;H,H₂OPh,H,H,F], [ZC71;H,c-Pr,H,H,F], [ZC72;H,c-Pen,H,H,F], [ZC73;H,c-Hex,H,H,F], [ZC74;H,H,Me,H,F], [ZC75;H,H,Et,H,F], [ZC76;H,H,Pr,H,F], [ZC77;H,H,i-Pr,H,F], [ZC78;H,H,t-Bu,H,F], [ZC79;H,H₂OMe,H,F], [ZC80;H,H₂OEt,H,F], [ZC81;H,H₂OPr,H,F], [ZC82;H,H₂Oi-Pr,H,F], [ZC83;H,H,CF₃,H,F], [ZC84;H,H,CF₂H,H,F], [ZC85;H,H,CFH₂,H,F],[ZC86;H,H,F,H,F], [ZC87;H,H,Cl,H,F], [ZC88;H,H,Br,H,F], [ZC89;H,H,CN,H,F], [ZC90;H,H,Ph,H,F], [ZC91;H,H₂OPh,H,F], [ZC92;H,H,c-Pr,H,F], [ZC93;H,H,c-Pen,H,F], [ZC94;H,H,c-Hex,H,F], [ZC95;H,H,H,H,Cl], [ZC96;Me,H,H,H,Cl], [ZC97;F,H,H,H,Cl], [ZC98;Cl,H,H,H,Cl], [ZC99;H,Me,H,H,Cl], [ZC100;H,Et,H,H,Cl], [ZC101;H,Pr,H,H,Cl], [ZC102;H,i-Pr,H,H,Cl], [ZC103;H,t-Bu,H,H,Cl], [ZC104;H₂OMe,H,H,Cl],[ZC105;H₂OEt,H,H,Cl], [ZC106;H₂OPr,H,H,Cl], [ZC107;H₂Oi-Pr,H,H,Cl], [ZC108;H,CF₃,H,H,Cl], [ZC109;H,CF₂H,H,H,Cl], [ZC110;H,CFH₂,H,H,Cl], [ZC111;H,F,H,H,Cl], [ZC112;H,Cl,H,H,Cl], [ZC113;H,Br,H,H,Cl], [ZC114;H,CN,H,H,Cl], [ZC115;H,Ph,H,H,Cl], [ZC116;H₂OPh,H,H,Cl], [ZC117;H,c-Pr,H,H,Cl], [ZC118;H,c-Pen,H,H,Cl], [ZC119;H,c-Hex,H,H,Cl], [ZC120;H,H,Me,H,Cl], [ZC121;H,H,Et,H,Cl], [ZC122;H,H,Pr,H,Cl], [ZC123;H,H,i-Pr,H,Cl], [ZC124;H,H,t-Bu,H,Cl], [ZC125;H,H₂OMe,H,Cl], [ZC126;H,H₂OEt,H,Cl], [ZC127;H,H₂OPr,H,Cl], [ZC128;H,H₂Oi-Pr,H,Cl], [ZC129;H,H,CF₃,H,Cl], [ZC130;H,H,CF₂H,H,Cl], [ZC131;H,H,CFH₂,H,Cl], [ZC132;H,H,F,H,Cl], [ZC133;H,H,Cl,H,Cl], [ZC134;H,H,Br,H,Cl], [ZC135;H,H,CN,H,Cl], [ZC136;H,H,Ph,H,Cl], [ZC137;H,H₂OPh,H,Cl], [ZC138;H,H,c-Pr,H,Cl], [ZC139;H,H,c-Pen,H,Cl], [ZC140;H,H,c-Hex,H,Cl], [ZC141;H,H,H,H,Me], [ZC142;Me,H,H,H,Me], [ZC143;F,H,H,H,Me], [ZC144;Cl,H,H,H,Me], [ZC145;H,Me,H,H,Me], [ZC146;H,Et,H,H,Me], [ZC147;H,Pr,H,H,Me], [ZC148;H,i-Pr,H,H,Me], [ZC149;H,t-Bu,H,H,Me], [ZC150;H₂OMe,H,H,Me], [ZC151;H₂OEt,H,H,Me], [ZC152;H₂OPr,H,H,Me], [ZC153;H₂Oi-Pr,H,H,Me], [ZC154;H,CF₃,H,H,Me], [ZC155;H,CF₂H,H,H,Me],[ZC156;H,CFH₂,H,H,Me], [ZC157;H,F,H,H,Me], [ZC158;H,Cl,H,H,Me], [ZC159;H,Br,H,H,Me], [ZC160;H,CN,H,H,Me], [ZC161;H,Ph,H,H,Me],[ZC162;H₂OPh,H,H,Me],[ZC163;H,c-Pr,H,H,Me], [ZC164;H,c-Pen,H,H,Me], [ZC165;H,c-Hex,H,H,Me], [ZC166;H,H,Me,H,Me], [ZC167;H,H,Et,H,Me], [ZC168;H,H,Pr,H,Me], [ZC169;H,H,i-Pr,H,Me], [ZC170;H,H,t-Bu,H,Me], [ZC171;H,H₂OMe,H,Me], [ZC172;H,H₂OEt,H,Me], [ZC173;H,H₂OPr,H,Me], [ZC174;H,H₂Oi-Pr,H,Me], [ZC175;H,H,CF₃,H,Me], [ZC176;H,H,CF₂H,H,Me], [ZC177;H,H,CFH₂,H,Me], [ZC178;H,H,F,H,Me], [ZC179;H,H,Cl,H,Me], [ZC180;H,H,Br,H,Me], [ZC181;H,H,CN,H,Me], [ZC182;H,H,Ph,H,Me], [ZC183;H,H₂OPh,H,Me], [ZC184;H,H,c-Pr,H,Me], [ZC185;H,H,c-Pen,H,Me], [ZC186;H,H,c-Hex,H,Me], [ZC187;H,H,H,H,OMe], [ZC188;Me,H,H,H,OMe], [ZC189;F,H,H,H,OMe], [ZC190;Cl,H,H,H,OMe], [ZC191;H,Me,H,H,OMe], [ZC192;H,Et,H,H,OMe], [ZC193;H,Pr,H,H₂OMe], [ZC194;H,i-Pr,H,H,OMe], [ZC195;H,t-Bu,H,H,OMe], [ZC196;H,OMe,H,H,OMe], [ZC197;H,OEt,H,H,OMe], [ZC198;H,OPr,H,H,OMe], [ZC199;H,Oi-Pr,H,H,OMe], [ZC200;H,CF₃,H,H,OMe], [ZC201;H,CF₂H,H,H,OMe], [ZC202;H,CFH₂,H,H,OMe], [ZC203;H,F,H,H,H₂OMe], [ZC204;H,Cl,H,H₂OMe], [ZC205;H,Br,H,H,OMe], [ZC206;H,CN,H,H,OMe], [ZC207;H,Ph,H,H₂OMe], [ZC208;H₂OPh,H,H₂OMe], [ZC209;H,c-Pr,H,H₂OMe], [ZC210;H,c-Pen,H,H,OMe], [ZC211;H,c-Hex,H,H,OMe], [ZC212;H,H,Me,H,OMe], [ZC213;H,H,Et,H,OMe], [ZC214;H,H,Pr,H,OMe], [ZC215;H,H,i-Pr,H,OMe], [ZC216;H,H,t-Bu,H,OMe], [ZC217;H,H₂OMe,H₂OMe], [ZC218;H,H₂OEt,H₂OMe], [ZC219;H,H₂OPr,H₂OMe], [ZC220;H,H₂Oi-Pr,H₂OMe], [ZC221;H,H,CF₃,H,OMe], [ZC222;H,H,CF₂H,H₂OMe], [ZC223;H,H,CFH₂,H₂OMe], [ZC224;H,H,F,H₂OMe], [ZC225;H,H,Cl,H₂OMe], [ZC226;H,H,Br,H₂OMe], [ZC227;H,H,CN,H₂OMe], [ZC228;H,H,Ph,H₂OMe], [ZC229;H,H₂OPh,H₂OMe], [ZC230;H,H,c-Pr,H₂OMe], [ZC231;H,H,c-Pen,H₂OMe], [ZC232;H,H,c-Hex,H₂OMe], [ZC233;H,H,H,H,CF₃], [ZC234;Me,H,H,H,CF₃], [ZC235;F,H,H,H,CF₃], [ZC236;Cl,H,H,H,CF₃], [ZC237;H,Me,H,H,CF₃], [ZC238;H,Et,H,H,CF₃], [ZC239;H,Pr,H,H,CF₃], [ZC240;H,i-Pr,H,H,CF₃], [ZC241;H,t-Bu,H,H,CF₃], [ZC242;H₂OMe,H,H,CF₃], [ZC243;H₂OEt,H,H,CF₃], [ZC244;H₂OPr,H,H,CF₃], [ZC245;H₂Oi-Pr,H,H,CF₃], [ZC246;H,CF₃,H,H,CF₃], [ZC247;H,CF₂H,H,H,CF₃], [ZC248;H,CFH₂,H,H,CF₃], [ZC249;H,F,H,H,CF₃], [ZC250;H,Cl,H,H,CF₃], [ZC251;H,Br,H,H,CF₃], [ZC252;H,CN,H,H,CF₃], [ZC253;H,Ph,H,H,CF₃], [ZC254;H₂OPh,H,H,CF₃], [ZC255;H,c-Pr,H,H,CF₃], [ZC256;H,c-Pen,H,H,CF₃], [ZC257;H,c-Hex,H,H,CF₃], [ZC258;H,H,Me,H,CF₃], [ZC259;H,H,Et,H,CF₃], [ZC260;H,H,Pr,H,CF₃], [ZC261;H,H,i-Pr,H,CF₃], [ZC262;H,H,t-Bu,H,CF₃], [ZC263;H,H₂OMe,H,CF₃], [ZC264;H,H₂OEt,H,CF₃], [ZC265;H,H₂OPr,H,CF₃], [ZC266;H,H₂Oi-Pr,H,CF₃], [ZC267;H,H,CF₃,H,CF₃], [ZC268;H,H,CF₂H,H,CF₃], [ZC269;H,H,CFH₂,H,CF₃], [ZC270;H,H,F,H,CF₃], [ZC271;H,H,Cl,H,CF₃], [ZC272;H,H,Br,H,CF₃], [ZC273;H,H,CN,H,CF₃], [ZC274;H,H,Ph,H,CF₃], [ZC275;H,H₂OPh,H,CF₃], [ZC276;H,H,c-Pr,H,CF₃], [ZC277;H,H,c-Pen,H,CF₃], [ZC278;H,H,c-Hex,H,CF₃], [ZC279;H,F,F,H,H], [ZC280;H,F,H,F,H], [ZC281;H,F,F,F,H], [ZC282;F,F,F,H,H], [ZC283;F,F,H,F,H],[ZC284;F,H,F,F,H], [ZC285;F,F,F,F,F], [ZC286;H,Cl,H,Cl,H], [ZC287;H₂OMe,H₂OMe,H], [ZC288;H,F,Cl,H,H], [ZC289;H,F,Me,H,H], [ZC290;H,F,OMe,H,H], [ZC291;H,F,CF₃,H,H], [ZC292;H,Cl,F,H,H], [ZC293;H,Cl,Cl,H,H], [ZC294;H,Cl,Me,H,H], [ZC295;H,Cl,OMe,H,H], [ZC296;H,Cl,CF₃,H,H], [ZC297;H,Me,F,H], [ZC298;H,Me,Cl,H,H], [ZC299;H,Me,Me,H,H], [ZC300;H,Me,OMe,H,H], [ZC301;H,Me,CF₃,H,H], [ZC302;H₂OMe,F,H,H], [ZC303;H₂OMe,Cl,H,H], [ZC304;H₂OMe,Me,H,H], [ZC305;H₂OMe,OMe,H,H], [ZC306;H₂OMe,CF₃,H,H], [ZC307;H,CF₃,F,H,H], [ZC308;H,CF₃,Cl,H,H], [ZC309;H,CF₃,F,H,H], [ZC310;H,CF₃,Cl,H,H], [ZC311;H,CF₃,F,H,H].

A compound represented by formula (1C) wherein Q represents a group represented by Q1, L represents an oxygen atom, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX32).

A compound represented by formula (1C) wherein Q represents a group represented by Q1, L represents $CH_2$, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX33).

A compound represented by formula (1C) wherein Q represents a group represented by Q1, L represents $CH_2$, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX34).

A compound represented by formula (1C) wherein Q represents a group represented by Q1, L represents NCH$_3$, $R^1$ represents a hydrogen atom, and a combination of $R^{x5}$, $R^{x6}$, $R^{x7}$, $R^{x8}$ and $R^{x9}$ represents any combination indicated in the combination C (hereinafter, referred to as Compound Class SX35).

A compound represented by formula (1C) wherein Q represents a group represented by Q2, X represents an oxygen atom, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX36).

A compound represented by formula (1C) wherein Q represents a group represented by Q2, X represents an oxygen atom, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX37).

A compound represented by formula (1C) wherein Q represents a group represented by Q2, X represents NH, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX38).

A compound represented by formula (1C) wherein Q represents a group represented by Q2, X represents NH, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX39).

A compound represented by formula (1C) wherein Q represents a group represented by Q3, $R^3$ represents a difluoromethyl group, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX40).

A compound represented by formula (1C) wherein Q represents a group represented by Q3, $R^3$ represents a difluoromethyl group, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX41).

A compound represented by formula (1C) wherein Q represents a group represented by Q3, $R^3$ represents a methoxy group, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX42).

A compound represented by formula (1C) wherein Q represents a group represented by Q3, $R^3$ represents a methoxy group, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX43).

A compound represented by formula (1C) wherein Q represents a group represented by Q4, $R^1$ represents a methyl group, and a combination of $R^{x5}$, $R^{x6}$, $R^{x7}$, $R^{x8}$ and $R^{x9}$ represents any combination indicated in the combination C (hereinafter, referred to as Compound Class SX44).

A compound represented by formula (1C) wherein Q represents a group represented by Q4, $R^1$ represents a chlorine atom, and a combination of $R^{x5}$, $R^{x6}$, $R^{x7}$, $R^{x8}$ and $R^{x9}$ represents any combination indicated in the combination C (hereinafter, referred to as Compound Class SX45).

A compound represented by formula (1D):

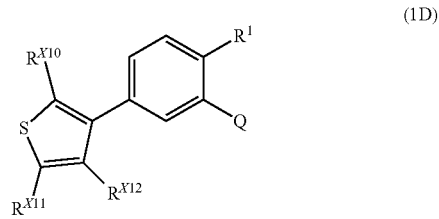

(1D)

wherein Q represents a group represented by Q1, L represents an oxygen atom, $R^1$ represents a methyl group, and a combination of $R^{x10}$, $R^{x11}$, and $R^{x12}$ represents any combination indicated in the combination D (hereinafter, referred to as Compound Class SX46).

The combination D consists of the substituent number ZD1 to ZD198. The substituent number ZD1 to ZD198 represents any combinations of $R^{x10}$, $R^{x11}$ and $R^{x12}$ in the compound represented formula (1D), and hereinafter, which is indicated as [Substituent Number: $R^{x10}$; $R^{x11}$; $R^{x12}$]. For example, "Substituent Number ZD2" represents a combination where $R^{x11}$ represents a methyl group, and $R^{x10}$, and $R^{x12}$ each is a hydrogen atom.

Combination D
[ZD1;H,H,H], [ZD2;H,Me,H], [ZD3;H,Et,H], [ZD4; H$_2$OMe,H], [ZD5;H$_2$OEt,H], [ZD6;H,CF$_3$,H], [ZD7;H, CF$_2$H,H], [ZD8;H,CFH$_2$,H], [ZD9;H,F,H], [ZD10;H,Cl,H], [ZD11;H,Br,H], [ZD12;H,CN,H], [ZD13;H,Ph,H], [ZD14; H$_2$OPh,H], [ZD15;H,c-Pr,H], [ZD16;H,c-Pen,H], [ZD17;H, c-Hex,H], [ZD18;F,H,H], [ZD19;F,Me,H], [ZD20;F,Et,H], [ZD21;F,OMe,H], [ZD22;F,OEt,H], [ZD23;F, CF$_3$,H], [ZD24;F,CF$_2$H,H], [ZD25;F,CFH$_2$,H], [ZD26;F,F,H], [ZD27;F,Cl,H], [ZD28;F,Br,H], [ZD29;F,CN,H], [ZD30;F, Ph,H], [ZD31;F,OPh,H], [ZD32;F,c-Pr,H], [ZD33;F,c-Pen, H], [ZD34;F,c-Hex,H], [ZD35;H,H,F], [ZD36;H,Me,F], [ZD37;H,Et,F], [ZD38;H$_2$OMe,F], [ZD39;H$_2$OEt,F], [ZD40;H,CF$_3$,F], [ZD41;H,CF$_2$H,F], [ZD42;H,CFH$_2$,F], [ZD43;H,F,F], [ZD44;H,Cl,F], [ZD45;H,Br,F], [ZD46;H, CN,F], [ZD47;H,Ph,F], [ZD48;H$_2$OPh,F], [ZD49;H,c-Pr,F], [ZD50;H,c-Pen,F], [ZD51;H,c-Hex,F], [ZD52;Cl,H,H], [ZD53;Cl,Me,H], [ZD54;Cl,Et,H], [ZD55;Cl,OMe,H], [ZD56;Cl,OEt,H], [ZD57;Cl,CF$_3$,H], [ZD58;Cl,CF$_2$H,H], [ZD59;Cl,CFH$_2$,H], [ZD60;Cl,F,H], [ZD61;Cl,Cl,H], [ZD62;Cl,Br,H], [ZD63;Cl,CN,H], [ZD64;Cl,Ph,H], [ZD65;Cl,OPh,H], [ZD66;Cl,c-Pr,H], [ZD67;Cl,c-Pen,H], [ZD68;Cl,c-Hex,H], [ZD69;H,H,Cl], [ZD70;H,Me,Cl], [ZD71;H,Et,Cl], [ZD72;H$_2$OMe,Cl], [ZD73;H$_2$OEt,Cl], [ZD74;H,CF$_3$,Cl], [ZD75;H,CF$_2$H,Cl], [ZD76;H,CFH$_2$,Cl], [ZD77;H,F,Cl], [ZD78;H,Cl,Cl], [ZD79;H,Br,Cl], [ZD80;H, CN,Cl], [ZD81;H,Ph,Cl], [ZD82;H$_2$OPh,Cl], [ZD83;H,c-Pr, Cl], [ZD84;H,c-Pen,Cl], [ZD85;H,c-Hex,Cl], [ZD86;Me,H, H], [ZD87;Me,Me,H], [ZD88;Me,Et,H], [ZD89;Me,OMe, H], [ZD90;Me,OEt,H], [ZD91;Me,CF$_3$,H], [ZD92;Me, CF$_2$H,H], [ZD93;Me,CFH$_2$,H], [ZD94;Me,F,H], [ZD95;Me, Cl,H], [ZD96;Me,Br,H], [ZD97;Me,CN,H], [ZD98;Me,Ph, H], [ZD99;Me,OPh,H], [ZD100;Me,c-Pr,H],[ZD101;Me,c-Pen,H], [ZD102;Me,c-Hex,H], [ZD103;H,H,Me], [ZD104; H,Me,Me], [ZD105;H,Et,Me], [ZD106;H$_2$OMe,Me], [ZD107;H$_2$OEt,Me], [ZD108;H,CF$_3$,Me], [ZD109;H,CF$_2$H, Me], [ZD110;H,CFH$_2$,Me], [ZD111;H,F,Me], [ZD112;H,Cl, Me], [ZD113;H,Br,Me], [ZD114;H,CN,Me], [ZD115;H,Ph, Me], [ZD116;H$_2$OPh,Me], [ZD117;H,c-Pr,Me], [ZD118;H, c-Pen,Me], [ZD119;H,c-Hex,Me], [ZD120;OMe,H,H], [ZD121;OMe,Me,H],[ZD122;OMe,Et,H], [ZD123;OMe, OMe,H], [ZD124;OMe,OEt,H], [ZD125;OMe,CF$_3$,H], [ZD126;OMe,CF$_2$H,H], [ZD127;OMe,CFH$_2$,H], [ZD128; OMe,F,H], [ZD129;OMe,Cl,H], [ZD130;OMe,Br,H], [ZD131;OMe,CN,H], [ZD132;OMe,Ph,H], [ZD133;OMe, OPh,H], [ZD134;OMe,c-Pr,H], [ZD135;OMe,c-Pen,H], [ZD136;OMe,c-Hex,H], [ZD137;H,H$_2$OMe], [ZD138;H, Me,OMe], [ZD139;H,Et,OMe], [ZD140;H$_2$OMe,OMe], [ZD141;H$_2$OEt,OMe], [ZD142;H,CF$_3$,OMe], [ZD143;H, CF$_2$H,OMe], [ZD144;H,CFH$_2$,OMe], [ZD145;H,F,OMe], [ZD146;H,Cl,OMe], [ZD147;H,Br,OMe], [ZD148;H,CN, OMe], [ZD149;H,Ph,OMe], [ZD150;H$_2$OPh,OMe], [ZD151;H,c-Pr,OMe], [ZD152;H,c-Pen,OMe], [ZD153;H, c-Hex,OMe], [ZD154;CF$_3$,H,H], [ZD155;CF$_3$,Me,H], [ZD156;CF$_3$,Et,H], [ZD157;CF$_3$,OMe,H], [ZD158;CF$_3$, OEt,H], [ZD159;CF$_3$,CF$_3$,H], [ZD160;CF$_3$,CF$_2$H,H], [ZD161;CF$_3$,CFH$_2$,H], [ZD162;CF$_3$,F,H], [ZD163;CF$_3$,Cl, H], [ZD164;CF$_3$,Br,H], [ZD165;CF$_3$,CN,H], [ZD166;CF$_3$, Ph,H], [ZD167;CF$_3$,OPh,H], [ZD168;CF$_3$,c-Pr,H], [ZD169; CF$_3$,c-Pen,H], [ZD170;CF$_3$,c-Hex,H], [ZD171;H,H,CF$_3$], [ZD172;H,Me,CF$_3$], [ZD173;H,Et,CF$_3$], [ZD174;H$_2$OMe, CF$_3$], [ZD175;H$_2$OEt,CF$_3$], [ZD176;H,CF$_3$,CF$_3$], [ZD177; H,CF$_2$H,CF$_3$], [ZD178;H,CFH$_2$,CF$_3$], [ZD179;H,F,CF$_3$], [ZD180;H,Cl,CF$_3$], [ZD181;H,Br,CF$_3$], [ZD182;H,CN, CF$_3$], [ZD183;H,Ph,CF$_3$], [ZD184;H$_2$OPh,CF$_3$], [ZD185;H, c-Pr,CF$_3$], [ZD186;H,c-Pen,CF$_3$], [ZD187;H,c-Hex,CF$_3$], [ZD188;H,CHO,H], [ZD189;H,C(O)Me,H], [ZD190;H,CN, H], [ZD191;CHO,H,H], [ZD192;C(O)Me,H,H], [ZD193; CN,H,H], [ZD194;H,H,CHO], [ZD195;H,H,C(O)Me], [ZD196;H,H,CN], [ZD197;Me,Me,H], [ZD198;Cl,Cl,H].

A compound represented by formula (1D) wherein Q represents a group represented by Q1, L represents an oxygen atom, R$^1$ represents a chlorine atom, and a combination of R$^{x10}$, R$^{x11}$ and R$^{x12}$ represents any combination indicated in the combination D (hereinafter, referred to as Compound Class SX47).

A compound represented by formula (1D) wherein Q represents a group represented by Q1, L represents CH$_2$, R$^1$ represents a methyl group, and a combination of R$^{x10}$, R$^{x11}$ and R$^{x12}$ represents any combination indicated in the combination D (hereinafter, referred to as Compound Class SX48).

A compound represented by formula (1D) wherein Q represents a group represented by Q1, L represents CH$_2$, R$^1$ represents a chlorine atom, and a combination of R$^{x10}$, R$^{x11}$ and R$^{x12}$ represents any combination indicated in the combination D (hereinafter, referred to as Compound Class SX49).

A compound represented by formula (1D) wherein Q represents a group represented by Q1, L represents NCH$_3$, R$^1$ represents a hydrogen atom, and a combination of R$^{x10}$, R$^{x11}$ and R$^{x12}$ represents any combination indicated in the combination D (hereinafter, referred to as Compound Class SX50).

A compound represented by formula (1D) wherein Q represents a group represented by Q2, X represents an oxygen atom, R$^1$ represents a methyl group, and a combination of R$^{x10}$, R$^{x11}$ and R$^{x12}$ represents any combination indicated in the combination D (hereinafter, referred to as Compound Class SX51).

A compound represented by formula (1D) wherein Q represents a group represented by Q2, X represents an oxygen atom, R$^1$ represents a chlorine atom, and a combination of R$^{x10}$, R$^{x11}$ and R$^{x12}$ represents any combination indicated in the combination D (hereinafter, referred to as Compound Class SX52).

A compound represented by formula (1D) wherein Q represents a group represented by Q2, X represents NH, R$^1$ represents a methyl group, and a combination of R$^{x10}$, R$^{x11}$ and R$^{x12}$ represents any combination indicated in the combination D (hereinafter, referred to as Compound Class SX53).

A compound represented by formula (1D) wherein Q represents a group represented by Q2, X represents NH, R$^1$ represents a chlorine atom, and a combination of R$^{x10}$, R$^{x11}$ and R$^{x12}$ represents any combination indicated in the combination D (hereinafter, referred to as Compound Class SX54).

A compound represented by formula (1D) wherein Q represents a group represented by Q3, R$^3$ represents a difluoromethyl group, R$^1$ represents a methyl group, and a combination of R$^{x10}$, R$^{x11}$ and R$^{x12}$ represents any combination indicated in the combination D (hereinafter, referred to as Compound Class SX55).

A compound represented by formula (1D) wherein Q represents a group represented by Q3, R$^3$ represents a difluoromethyl group, R$^1$ represents a chlorine atom, and a combination of R$^{x10}$, R$^{x11}$ and R$^{x12}$ represents any combination indicated in the combination D (hereinafter, referred to as Compound Class SX56).

A compound represented by formula (1D) wherein Q represents a group represented by Q3, R$^3$ represents a methoxy group, R$^1$ represents a methyl group, and a combination of R$^{x10}$, R$^{x11}$ and R$^{x12}$ represents any combination indicated in the combination D (hereinafter, referred to as Compound Class SX57).

A compound represented by formula (1D) wherein Q represents a group represented by Q3, R$^3$ represents a methoxy group, R$^1$ represents a chlorine atom, and a combination of R$^{x10}$, R$^{x11}$ and R$^{x12}$ represents any combination indicated in the combination D (hereinafter, referred to as Compound Class SX58).

A compound represented by formula (1D) wherein Q represents a group represented by Q4, R$^1$ represents a methyl group, and a combination and R$^{x10}$, R$^{x11}$ and R$^{x12}$ represents any combination indicated in the combination D (hereinafter, referred to as Compound Class SX59).

A compound represented by formula (1D) wherein Q represents a group represented by Q4, R$^1$ represents a chlorine atom, and a combination of R$^{x10}$, R$^{x11}$ and R$^{x12}$ represents any combination indicated in the combination D (hereinafter, referred to as Compound Class SX60).

A compound represented by formula (1E):

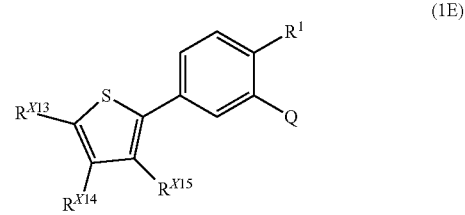

wherein Q represents a group represented by Q1, L represents an oxygen atom, R$^1$ represents a methyl group, and a combination of R$^{x13}$, R$^{x14}$, and R$^{x15}$ represents any combination indicated in the combination E (hereinafter, referred to as Compound Class SX61).

The combination E consists of the substituent number ZE1 to ZE214. The substituent number ZE1 to ZE214 represents any combinations of R$^{x13}$, R$^{x14}$ and R$^{x15}$ in the compound represented formula (1E), and hereinafter, which is indicated as [Substituent Number: R$^{x13}$; R$^{x14}$; R$^{x15}$]. For example, "Substituent Number ZE2" represents a combination where $R^{x13}$ represents a methyl group, and $R^{x14}$, and $R^{x15}$ each is a hydrogen atom.

Combination E

[ZE1;H,H,H], [ZE2;Me,H,H], [ZE3;Et,H,H], [ZE4;OMe,H,H], [ZE5;OEt,H,H], [ZE6;CF$_3$,H,H], [ZE7;CF$_2$H,H,H], [ZE8;CFH$_2$,H,H], [ZE9;F,H,H], [ZE10;Cl,H,H], [ZE11;Br,H,H], [ZE12;CN,H,H], [ZE13;Ph,H,H], [ZE14;OPh,H,H], [ZE15;c-Pr,H,H], [ZE16;c-Pen,H,H], [ZE17;c-Hex,H,H], [ZE18;H,Me,H], [ZE19;H,Et,H], [ZE20;H$_2$OMe,H], [ZE21;H$_2$OEt,H], [ZE22;H,CF$_3$,H], [ZE23;H,CF$_2$H,H], [ZE24;H,CFH$_2$,H], [ZE25;H,F,H], [ZE26;H,Cl,H], [ZE27;H,Br,H], [ZE28;H,CN,H], [ZE29;H,Ph,H], [ZE30;H$_2$OPh,H], [ZE31;H,c-Pr,H], [ZE32;H,c-Pen,H], [ZE33;H,c-Hex,H], [ZE34;H,H,F], [ZE35;Me,H,F], [ZE36;Et,H,F], [ZE37;OMe,H,F], [ZE38;OEt,H,F], [ZE39;CF$_3$,H,F], [ZE40;CF$_2$H,H,F], [ZE41;CFH$_2$,H,F], [ZE42;F,H,F], [ZE43;Cl,H,F], [ZE44;Br,H,F], [ZE45;CN,H,F], [ZE46;Ph,H,F], [ZE47;OPh,H,F], [ZE48;c-Pr,H,F], [ZE49;c-Pen,H,F], [ZE50;c-Hex,H,F], [ZE51;H,Me,F], [ZE52;H,Et,F], [ZE53;H$_2$OMe,F], [ZE54;H$_2$OEt,F], [ZE55;H,CF$_3$,F], [ZE56;H,CF$_2$H,F], [ZE57;H,CFH$_2$,F], [ZE58;H,F,F], [ZE59;H,Cl,F], [ZE60;H,Br,F], [ZE61;H,CN,F], [ZE62;H,Ph,F], [ZE63;H$_2$OPh,F], [ZE64;H,c-Pr,F], [ZE65;H,c-Pen,F], [ZE66;H,c-Hex,F], [ZE67;H,H,Cl], [ZE68;Me,H,Cl], [ZE69;Et,H,Cl], [ZE70;OMe,H,Cl], [ZE71;OEt,H,Cl], [ZE72;CF$_3$,H,Cl], [ZE73;CF$_2$H,H,Cl], [ZE74;CFH$_2$,H,Cl], [ZE75;F,H,Cl], [ZE76;Cl,H,Cl], [ZE77;Br,H,Cl], [ZE78;CN,H,Cl], [ZE79;Ph,H,Cl], [ZE80;OPh,H,Cl], [ZE81;c-Pr,H,Cl], [ZE82;c-Pen,H,Cl], [ZE83;c-Hex,H,Cl], [ZE84;H,Me,Cl], [ZE85;H,Et,Cl], [ZE86;H$_2$OMe,Cl], [ZE87;H$_2$OEt,Cl], [ZE88;H,CF$_3$,Cl], [ZE89;H,CF$_2$H,Cl], [ZE90;H,CFH$_2$,Cl], [ZE91;H,F,Cl], [ZE92;H,Cl,Cl], [ZE93;H,Br,Cl], [ZE94;H,CN,Cl], [ZE95;H,Ph,Cl], [ZE96;H$_2$OPh,Cl], [ZE97;H,c-Pr,Cl], [ZE98;H,c-Pen,Cl], [ZE99;H,c-Hex,Cl], [ZE100;H,H,Me], [ZE101;Me,H,Me], [ZE102;Et,H,Me], [ZE103;OMe,H,Me], [ZE104;OEt,H,Me], [ZE105;CF$_3$,H,Me], [ZE106;CF$_2$H,H,Me], [ZE107;CFH$_2$,H,Me], [ZE108;F,H,Me], [ZE109;Cl,H,Me], [ZE110;Br,H,Me], [ZE111;CN,H,Me], [ZE112;Ph,H,Me], [ZE113;OPh,H,Me], [ZE114;c-Pr,H,Me], [ZE115;c-Pen,H,Me], [ZE116;c-Hex,H,Me], [ZE117;H,Me,Me], [ZE118;H,Et,Me], [ZE119;H$_2$OMe,Me], [ZE120;H$_2$OEt,Me], [ZE121;H,CF$_3$,Me], [ZE122;H,CF$_2$H,Me], [ZE123;H,CFH$_2$,Me], [ZE124;H,F,Me], [ZE125;H,Cl,Me], [ZE126;H,Br,Me], [ZE127;H,CN,Me], [ZE128;H,Ph,Me], [ZE129;H$_2$OPh,Me], [ZE130;H,c-Pr,Me], [ZE131;H,c-Pen,Me], [ZE132;H,c-Hex,Me], [ZE133;H,H$_2$OMe], [ZE134;Me,H$_2$OMe], [ZE135;Et,H$_2$OMe], [ZE136;OMe,H$_2$OMe], [ZE137;OEt,H$_2$OMe], [ZE138;CF$_3$,H$_2$OMe], [ZE139;CF$_2$H,H$_2$OMe], [ZE140;CFH$_2$,H$_2$OMe], [ZE141;F,H$_2$OMe], [ZE142;Cl,H$_2$OMe], [ZE143;Br,H$_2$OMe], [ZE144;CN,H$_2$OMe], [ZE145;Ph,H$_2$OMe], [ZE146;OPh,H$_2$OMe], [ZE147;c-Pr,H$_2$OMe], [ZE148;c-Pen,H$_2$OMe], [ZE149;c-Hex,H$_2$OMe], [ZE150;H,Me,OMe], [ZE151;H,Et,OMe], [ZE152;H$_2$OMe,OMe], [ZE153;H$_2$OEt,OMe], [ZE154;H,CF$_3$,OMe], [ZE155;H,CF$_2$H,OMe], [ZE156;H,CFH$_2$,OMe], [ZE157;H,F,OMe], [ZE158;H,Cl,OMe], [ZE159;H,Br,OMe], [ZE160;H,CN,OMe], [ZE161;H,Ph,OMe], [ZE162;H$_2$OPh,OMe], [ZE163;H,c-Pr,OMe], [ZE164;H,c-Pen,OMe], [ZE165;H,c-Hex,OMe], [ZE166;H,H,CF$_3$], [ZE167;Me,H,CF$_3$], [ZE168;Et,H,CF$_3$], [ZE169;OMe,H,CF$_3$], [ZE170;OEt,H,CF$_3$], [ZE171;CF$_3$,H,CF$_3$], [ZE172;CF$_2$H,H,CF$_3$], [ZE173;CFH$_2$,H,CF$_3$], [ZE174;F,H,CF$_3$], [ZE175;Cl,H,CF$_3$], [ZE176;Br,H,CF$_3$], [ZE177;CN,H,CF$_3$], [ZE178;Ph,H,CF$_3$], [ZE179;OPh,H,CF$_3$], [ZE180;c-Pr,H,CF$_3$], [ZE181;c-Pen,H,CF$_3$], [ZE182;c-Hex,H,CF$_3$], [ZE183;H,Me,CF$_3$], [ZE184;H,Et,CF$_3$], [ZE185;H$_2$OMe,CF$_3$], [ZE186;H$_2$OEt,CF$_3$], [ZE187;H,CF$_3$,CF$_3$], [ZE188;H,CF$_2$H,CF$_3$], [ZE189;H,CFH$_2$,CF$_3$], [ZE190;H,F,CF$_3$], [ZE191;H,Cl,CF$_3$], [ZE192;H,Br,CF$_3$], [ZE193;H,CN,CF$_3$], [ZE194;H,Ph,CF$_3$], [ZE195;H$_2$OPh,CF$_3$], [ZE196;H,c-Pr,CF$_3$], [ZE197;H,c-Pen,CF$_3$], [ZE198;H,c-Hex,CF$_3$], [ZE199;CHO,H,H], [ZE200;C(O)Me,H,H], [ZE201;CN,H,H], [ZE202;H,CHO,H], [ZE203;H,C(O)Me,H], [ZE204;H,CN,H], [ZE205;H,H,CHO], [ZE206;H,H,C(O)Me], [ZE207;H,H,CN], [ZE208;2-thienyl,H,H], [ZE209;C(O)OMe,H,H], [ZE210;Et,H,H], [ZE211;CN,Me,H], [ZE212;Br,Me,H], [ZE213;CHO,Me,H], [ZE214;Cl,Br,H].

A compound represented by formula (1E) wherein Q represents a group represented by Q1, L represents an oxygen atom, $R^1$ represents a chlorine atom, and a combination of $R^{x13}$, $R^{x14}$ and $R^{x15}$ represents any combination indicated in the combination E (hereinafter, referred to as Compound Class SX62).

A compound represented by formula (1E) wherein Q represents a group represented by Q1, L represents CH2, $R^1$ represents a methyl group, and a combination of $R^{x13}$, $R^{x14}$ and $R^{x15}$ represents any combination indicated in the combination E (hereinafter, referred to as Compound Class SX63).

A compound represented by formula (1E) wherein Q represents a group represented by Q1, L represents CH$_2$, $R^1$ represents a chlorine atom, and a combination of $R^{x13}$, $R^{x14}$ and $R^{x15}$ represents any combination indicated in the combination E (hereinafter, referred to as Compound Class SX64).

A compound represented by formula (1E) wherein Q represents a group represented by Q1, L represents NCH$_3$, $R^1$ represents a hydrogen atom, and a combination of $R^{x13}$, $R^{x14}$ and $R^{x15}$ represents any combination indicated in the combination E (hereinafter, referred to as Compound Class SX65).

A compound represented by formula (1E) wherein Q represents a group represented by Q2, X represents an oxygen atom, $R^1$ represents a methyl group, and a combination of $R^{x13}$, $R^{x14}$ and $R^{x15}$ represents any combination indicated in the combination E (hereinafter, referred to as Compound Class SX66).

A compound represented by formula (1E) wherein Q represents a group represented by Q2, X represents an oxygen atom, $R^1$ represents a chlorine atom, and a combination of $R^{x13}$, $R^{x14}$ and $R^{x15}$ represents any combination indicated in the combination E (hereinafter, referred to as Compound Class SX67).

A compound represented by formula (1E) wherein Q represents a group represented by Q2, X represents NH, $R^1$ represents a methyl group, and a combination of $R^{x13}$, $R^{x14}$ and $R^{x15}$ represents any combination indicated in the combination E (hereinafter, referred to as Compound Class SX68).

A compound represented by formula (1E) wherein Q represents a group represented by Q2, X represents NH, $R^1$ represents a chlorine atom, and a combination of $R^{x13}$, $R^{x14}$ and $R^{x15}$ represents any combination indicated in the combination E (hereinafter, referred to as Compound Class SX69).

A compound represented by formula (1E) wherein Q represents a group represented by Q3, $R^3$ represents a difluoromethyl group, $R^1$ represents a methyl group, and a combination of $R^{x13}$, $R^{x14}$ and $R^{x15}$ represents any combination indicated in the combination E (hereinafter, referred to as Compound Class SX70).

A compound represented by formula (1E) wherein Q represents a group represented by Q3, $R^3$ represents a difluoromethyl group, $R^1$ represents a chlorine atom, and a combination of $R^{x13}$, $R^{x14}$ and $R^{x15}$ represents any combination indicated in the combination E (hereinafter, referred to as Compound Class SX71).

A compound represented by formula (1E) wherein Q represents a group represented by Q3, $R^3$ represents a methoxy group, $R^1$ represents a methyl group, and a combination of $R^{x13}$, $R^{x14}$ and $R^{x15}$ represents any combination indicated in the combination E (hereinafter, referred to as Compound Class SX72).

A compound represented by formula (1E) wherein Q represents a group represented by Q3, $R^3$ represents a methoxy group, $R^1$ represents a chlorine atom, and a combination of $R^{x13}$, $R^{x14}$ and $R^{x15}$ represents any combination indicated in the combination E (hereinafter, referred to as Compound Class SX73).

A compound represented by formula (1E) wherein Q represents a group represented by Q4, $R^1$ represents a methyl group, and a combination of $R^{x13}$, $R^{x14}$ and $R^{x15}$ represents any combination indicated in the combination E (hereinafter, referred to as Compound Class SX74).

A compound represented by formula (1E) wherein Q represents a group represented by Q4, $R^1$ represents a chlorine atom, and a combination of $R^{x13}$, $R^{x14}$ and $R^{x15}$ represents any combination indicated in the combination E (hereinafter, referred to as Compound Class SX75).

A compound represented by formula (1F):

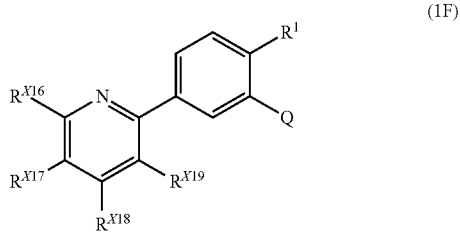

(1F)

wherein Q represents a group represented by Q1, L represents an oxygen atom, $R^1$ represents a methyl group, and a combination of $R^{x16}$, $R^{x17}$, $R^{x18}$, and $R^{x19}$ represents any combination indicated in the combination F (hereinafter, referred to as Compound Class SX76).

The combination F consists of the substituent number ZF1 to ZF444. The substituent number ZF1 to ZF444 represents any combinations of $R^{x16}$, $R^{x17}$, $R^{x17}$ and $R^{x18}$ in the compound represented formula (1F), and hereinafter, which is indicated as [Substituent Number: $R^{x16}$; $R^{x17}$; $R^{x18}$; $R^{x19}$]. For example, "Substituent Number ZF2" represents a combination where $R^{x16}$ represents a methyl group, and $R^{x17}$, $R^{x18}$, and $R^{x19}$ each is a hydrogen atom.

Combination F
[ZF1;H,H,H,H], [ZF2;Me,H,H,H], [ZF3;Et,H,H,H], [ZF4;Pr,H,H,H], [ZF5;i-Pr,H,H,H], [ZF6;t-Bu,H,H,H], [ZF7;OMe,H,H,H], [ZF8;OEt,H,H,H], [ZF9;OPr,H,H,H], [ZF10;Oi-Pr,H,H,H], [ZF11;CF₃,H,H,H], [ZF12;CF₂H,H,H,H], [ZF13;CFH₂,H,H,H], [ZF14;F,H,H,H], [ZF15;Cl,H,H,H], [ZF16;Br,H,H,H], [ZF17;CN,H,H,H], [ZF18;Ph,H,H,H], [ZF19;OPh,H,H,H], [ZF20;c-Pr,H,H,H], [ZF21;c-Pen,H,H,H], [ZF22;c-Hex,H,H,H], [ZF23;H,Me,H,H], [ZF24;H,Et,H,H], [ZF25;H,Pr,H,H], [ZF26;H,i-Pr,H,H], [ZF27;H,t-Bu,H,H], [ZF28;H₂OMe,H,H], [ZF29;H₂OEt,H,H], [ZF30;H₂OPr,H,H], [ZF31;H₂Oi-Pr,H,H], [ZF32;H,CF₃,H,H], [ZF33;H,CF₂H,H,H], [ZF34;H,CFH₂,H,H], [ZF35;H,F,H,H], [ZF36;H,Cl,H,H], [ZF37;H,Br,H,H], [ZF38;H,CN,H,H], [ZF39;H,Ph,H,H], [ZF40;H₂OPh,H,H], [ZF41;H,c-Pr,H,H], [ZF42;H,c-Pen,H,H], [ZF43;H,c-Hex,H,H], [ZF44;H,H,Me,H], [ZF45;H,H,Et,H], [ZF46;H,H,Pr,H], [ZF47;H,H,i-Pr,H], [ZF48;H,H,t-Bu,H], [ZF49;H,H₂OMe,H], [ZF50;H,H₂OEt,H], [ZF51;H,H₂OPr,H], [ZF52;H,H₂Oi-Pr,H], [ZF53;H,H,CF₃,H], [ZF54;H,H,CF₂H,H], [ZF55;H,H,CFH₂,H], [ZF56;H,H,F,H], [ZF57;H,H,Cl,H], [ZF58;H,H,Br,H], [ZF59;H,H,CN,H], [ZF60;H,H,Ph,H], [ZF61;H,H₂OPh,H], [ZF62;H,H,c-Pr,H], [ZF63;H,H,c-Pen,H], [ZF64;H,H,c-Hex,H], [ZF65;H,H,H,F], [ZF66;Me,H,H,F], [ZF67;Et,H,H,F], [ZF68;Pr,H,H,F], [ZF69;i-Pr,H,H,F], [ZF70;t-Bu,H,H,F], [ZF71;OMe,H,H,F], [ZF72;OEt,H,H,F], [ZF73;OPr,H,H,F], [ZF74;Oi-Pr,H,H,F], [ZF75;CF₃,H,H,F], [ZF76;CF₂H,H,H,F], [ZF77;CFH₂,H,H,F], [ZF78;F,H,H,F], [ZF79;Cl,H,H,F], [ZF80;Br,H,H,F], [ZF81;CN,H,H,F], [ZF82;Ph,H,H,F], [ZF83;OPh,H,H,F], [ZF84;c-Pr,H,H,F], [ZF85;c-Pen,H,H,F], [ZF86;c-Hex,H,H,F], [ZF87;H,Me,H,F], [ZF88;H,Et,H,F], [ZF89;H,Pr,H,F], [ZF90;H,i-Pr,H,F], [ZF91;H,t-Bu,H,F], [ZF92;H₂OMe,H,F], [ZF93;H₂OEt,H,F], [ZF94;H₂OPr,H,F], [ZF95;H₂Oi-Pr,H,F], [ZF96;H,CF₃,H,F], [ZF97;H,CF₂H,H,F], [ZF98;H,CFH₂,H,F], [ZF99;H,F,H,F], [ZF100;H,Cl,H,F], [ZF101;H,Br,H,F], [ZF102;H,CN,H,F], [ZF103;H,Ph,H,F], [ZF104;H₂OPh,H,F], [ZF105;H,c-Pr,H,F], [ZF106;H,c-Pen,H,F], [ZF107;H,c-Hex,H,F], [ZF108;H,H,Me,F], [ZF109;H,H,Et,F], [ZF110;H,H,Pr,F], [ZF111;H,H,i-Pr,F], [ZF112;H,H,t-Bu,F], [ZF113;H,H₂OMe,F], [ZF114;H,H₂OEt,F], [ZF115;H,H₂OPr,F], [ZF116;H,H₂Oi-Pr,F], [ZF117;H,H,CF₃,F], [ZF118;H,H,CF₂H,F], [ZF119;H,H,CFH₂,F], [ZF120;H,H,F,F], [ZF121;H,H,Cl,F], [ZF122;H,H,Br,F], [ZF123;H,H,CN,F], [ZF124;H,H,Ph,F], [ZF125;H,H₂OPh,F], [ZF126;H,H,c-Pr,F], [ZF127;H,H,c-Pen,F], [ZF128;H,H,c-Hex,F], [ZF129;H,H,H,Cl], [ZF130;Me,H,H,Cl], [ZF131;Et,H,H,Cl], [ZF132;Pr,H,H,Cl], [ZF133;i-Pr,H,H,Cl], [ZF134;t-Bu,H,H,Cl], [ZF135;OMe,H,H,Cl], [ZF136;OEt,H,H,Cl], [ZF137;OPr,H,H,Cl], [ZF138;Oi-Pr,H,H,Cl], [ZF139;CF₃,H,H,Cl], [ZF140;CF₂H,H,H,Cl], [ZF141;CFH₂,H,H,Cl], [ZF142;F,H,H,Cl], [ZF143;Cl,H,H,Cl], [ZF144;Br,H,H,Cl], [ZF145;CN,H,H,Cl], [ZF146;Ph,H,H,Cl], [ZF147;OPh,H,H,Cl], [ZF148;c-Pr,H,H,Cl], [ZF149;c-Pen,H,H,Cl], [ZF150;c-Hex,H,H,Cl], [ZF151;H,Me,H,Cl], [ZF152;H,Et,H,Cl], [ZF153;H,Pr,H,Cl], [ZF154;H,i-Pr,H,Cl], [ZF155;H,t-Bu,H,Cl], [ZF156;H₂OMe,H,Cl], [ZF157;H₂OEt,H,Cl], [ZF158;H₂OPr,H,Cl], [ZF159;H₂Oi-Pr,H,Cl], [ZF160;H,CF₃,H,Cl], [ZF161;H,CF₂H,H,Cl], [ZF162;H,CFH₂,H,Cl], [ZF163;H,F,H,Cl], [ZF164;H,Cl,H,Cl], [ZF165;H,Br,H,Cl], [ZF166;H,CN,H,Cl], [ZF167;H,Ph,H,Cl], [ZF168;H₂OPh,H,Cl], [ZF169;H,c-Pr,H,Cl], [ZF170;H,c-Pen,H,Cl], [ZF171;H,c-Hex,H,Cl], [ZF172;H,H,Me,Cl], [ZF173;H,H,Et,Cl], [ZF174;H,H,Pr,Cl], [ZF175;H,H,i-Pr,Cl], [ZF176;H,H,t-Bu,Cl], [ZF177;H,H₂OMe,Cl], [ZF178;H,H₂OEt,Cl], [ZF179;H,H₂OPr,Cl], [ZF180;H,H₂Oi-Pr,Cl], [ZF181;H,H,CF₃,Cl], [ZF182;H,H,CF₂H,Cl], [ZF183;H,H,CFH₂,Cl], [ZF184;H,H,F,Cl], [ZF185;H,H,Cl,Cl], [ZF186;H,H,Br,Cl], [ZF187;H,H,CN,Cl], [ZF188;H,H,Ph,Cl], [ZF189;H,H₂OPh,Cl], [ZF190;H,H,c-Pr,Cl], [ZF191;H,H,c-Pen,Cl], [ZF192;H,H,c-Hex,Cl], [ZF193;H,H,H,Me], [ZF194;Me,H,H,Me], [ZF195;Et,H,H,Me], [ZF196;Pr,H,H,Me], [ZF197;i-Pr,H,H,Me], [ZF198;t-Bu,H,H,Me], [ZF199;OMe,H,H,Me], [ZF200;OEt,H,H,Me], [ZF201;OPr,H,H,Me], [ZF202;Oi-Pr,H,H,Me], [ZF203;CF₃,H,H,Me], [ZF204;CF₂H,H,H,Me], [ZF205;CFH₂,H,H,Me], [ZF206;F,H,H,Me], [ZF207;Cl,H,H,Me], [ZF208;Br,H,H,Me], [ZF209;CN,H,H,Me], [ZF210;Ph,H,H,Me], [ZF211;OPh,H,H,Me], [ZF212;c-Pr,H,H,Me], [ZF213;c-Pen,H,H,Me], [ZF214;c-Hex,H,H,Me], [ZF215;H,Me,H,Me], [ZF216;H,Et,H,Me], [ZF217;H,Pr,H,Me], [ZF218;H,i-Pr,H,Me], [ZF219;H,t-Bu,H,Me], [ZF220;

H₂OMe,H,Me], [ZF221;H₂OEt,H,Me], [ZF222;H₂OPr,H, Me], [ZF223;H₂Oi-Pr,H,Me], [ZF224;H,CF₃,H,Me], [ZF225;H,CF₂H,H,Me], [ZF226;H,CFH₂,H,Me], [ZF227; H,F,H,Me], [ZF228;H,Cl,H,Me], [ZF229;H,Br,H,Me], [ZF230;H,CN,H,Me], [ZF231;H,Ph,H,Me], [ZF232; H₂OPh,H,Me], [ZF233;H,c-Pr,H,Me], [ZF234;H,c-Pen,H, Me], [ZF235;H,c-Hex,H,Me], [ZF236;H,H,Me,Me], [ZF237;H,H,Et,Me], [ZF238;H,H,Pr,Me], [ZF239;H,H,i-Pr, Me], [ZF240;H,H,t-Bu,Me], [ZF241;H,H₂OMe,Me], [ZF242;H,H₂OEt,Me], [ZF243;H,H₂OPr,Me], [ZF244;H, H₂Oi-Pr,Me], [ZF245;H,H,CF₃,Me], [ZF246;H,H,CF₂H, Me], [ZF247;H,H,CFH₂,Me], [ZF248;H,H,F,Me], [ZF249; H,H,Cl,Me], [ZF250;H,H,Br,Me], [ZF251;H,H,CN,Me], [ZF252;H,H,Ph,Me], [ZF253;H,H₂OPh,Me], [ZF254;H,H, c-Pr,Me], [ZF255; H, H, c-Pen,Me], [ZF256;H,H,c-Hex, Me], [ZF257;H,H,H₂OMe], [ZF258;Me,H,H₂OMe], [ZF259;Et,H,H₂OMe], [ZF260;Pr,H,H₂OMe], [ZF261;i-Pr, H,H₂OMe], [ZF262;t-Bu,H,H₂OMe], [ZF263;OMe,H, H₂OMe], [ZF264;OEt,H,H₂OMe], [ZF265;OPr,H,H₂OMe], [ZF266;Oi-Pr,H,H₂OMe], [ZF267;CF₃,H,H₂OMe], [ZF268; CF₂H,H,H,H₂OMe], [ZF269;CFH₂,H,H₂OMe], [ZF270;F,H, H₂OMe], [ZF271;Cl,H,H₂OMe], [ZF272;Br,H,H₂OMe], [ZF273;CN,H,H₂OMe], [ZF274;Ph,H,H₂OMe], [ZF275; OPh,H,H₂OMe], [ZF276;c-Pr,H,H₂OMe], [ZF277;c-Pen,H, H₂OMe], [ZF278;c-Hex,H,H₂OMe], [ZF279;H,Me, H₂OMe], [ZF280;H,Et,H₂OMe], [ZF281;H,Pr,H₂OMe], [ZF282;H,i-Pr,H₂OMe], [ZF283;H,t-Bu,H₂OMe], [ZF284; H₂OMe,H₂OMe], [ZF285;H₂OEt,H₂OMe], [ZF286;H₂OPr, H₂OMe], [ZF287;H₂Oi-Pr,H₂OMe], [ZF288;H,CF₃, H₂OMe], [ZF289;H,CF₂H,H₂OMe], [ZF290;H,CFH₂, H₂OMe], [ZF291;H,F,H₂OMe],[ZF292;H,Cl,H₂OMe], [ZF293;H,Br,H₂OMe], [ZF294;H,CN,H₂OMe], [ZF295;H, Ph,H₂OMe], [ZF296;H₂OPh,H₂OMe], [ZF297;H,c-Pr, H₂OMe], [ZF298;H,c-Pen,H₂OMe], [ZF299;H,c-Hex, H₂OMe], [ZF300;H,H,Me,OMe], [ZF301;H,H,Et,OMe], [ZF302;H,H,Pr,OMe], [ZF303;H,H,i-Pr,OMe], [ZF304;H, H,t-Bu,OMe], [ZF305;H,H₂OMe,OMe], [ZF306;H,H₂OEt, OMe], [ZF307;H,H₂OPr,OMe], [ZF308;H,H₂Oi-Pr,OMe], [ZF309;H,H,CF₃,OMe], [ZF310;H,H,CF₂H₂OMe], [ZF311; H,H,CFH₂,OMe], [ZF312;H,H,F,OMe], [ZF313;H,H,Cl, OMe], [ZF314;H,H,Br,OMe], [ZF315;H,H,CN,OMe], [ZF316;H,H,Ph,OMe], [ZF317;H,H₂OPh,OMe], [ZF318;H, H,c-Pr,OMe], [ZF319;H,H,c-Pen,OMe], [ZF320;H,H,c-Hex,OMe], [ZF321;H,H,H,CF₃], [ZF322;Me,H,H,CF₃], [ZF323;Et,H,H,CF₃], [ZF324;Pr,H,H,CF₃], [ZF325;i-Pr,H, H,CF₃], [ZF326;t-Bu,H,H,CF₃], [ZF327;OMe,H,H,CF₃], [ZF328;OEt,H,H,CF₃], [ZF329;OPr,H,H,CF₃], [ZF330;Oi-Pr,H,H,CF₃], [ZF331;CF₃,H,H,CF₃], [ZF332;CF₂H,H,H, CF₃], [ZF333;CFH₂,H,H,CF₃], [ZF334;F,H,H,CF₃], [ZF335;Cl,H,H,CF₃], [ZF336;Br,H,H,CF₃], [ZF337;CN,H, H,CF₃], [ZF338;Ph,H,H,CF₃], [ZF339;OPh,H,H,CF₃], [ZF340;c-Pr,H,H,CF₃], [ZF341;c-Pen,H,H,CF₃], [ZF342;c-Hex,H,H,CF₃], [ZF343;H,Me,H,CF₃], [ZF344;H,Et,H, CF₃], [ZF345;H,Pr,H,CF₃], [ZF346;H,i-Pr,H,CF₃], [ZF347; H,t-Bu,H,CF₃], [ZF348;H₂OMe,H,CF₃], [ZF349;H₂OEt,H, CF₃], [ZF350;H₂OPr,H,CF₃], [ZF351;H₂Oi-Pr,H,CF₃], [ZF352;H,CF₃,H,CF₃], [ZF353;H,CF₂H,H,CF₃], [ZF354;H, CFH₂,H,CF₃], [ZF355;H,F,H,CF₃], [ZF356;H,Cl,H,CF₃], [ZF357;H,Br,H,CF₃], [ZF358;H,CN,H,CF₃], [ZF359;H,Ph, H,CF₃], [ZF360;H₂OPh,H,CF₃], [ZF361;H,c-Pr,H,CF₃], [ZF362;H,c-Pen,H,CF₃], [ZF363;H,c-Hex,H,CF₃], [ZF364; H,H,Me,CF₃], [ZF365;H,H,Et,CF₃], [ZF366;H,H,Pr,CF₃], [ZF367;H,H,i-Pr,CF₃], [ZF368;H,H,t-Bu,CF₃], [ZF369;H, H₂OMe,CF₃], [ZF370;H,H₂OEt,CF₃], [ZF371;H,H₂OPr, CF₃], [ZF372;H,H₂Oi-Pr,CF₃], [ZF373;H,H,CF₃,CF₃], [ZF374;H,H,CF₂H,CF₃], [ZF375;H,H,CFH₂,CF₃], [ZF376; H,H,F,CF₃], [ZF377;H,H,Cl,CF₃], [ZF378;H,H,Br,CF₃], [ZF379;H,H,CN,CF₃], [ZF380;H,H,Ph,CF₃], [ZF381;H, H₂OPh,CF₃], [ZF382;H,H,c-Pr,CF₃], [ZF383;H,H,c-Pen, CF₃], [ZF384;H,H,c-Hex,CF₃], [ZF385;F,H,F,H], [ZF386;F, H,Cl,H], [ZF387;F,H,Me,H], [ZF388;F,H₂OMe,H], [ZF389; F,H,CF₃,H], [ZF390;F,H,CN,H], [ZF391;F,F,H,H], [ZF392; F,Cl,H,H], [ZF393;F,Me,H,H], [ZF394;F,OMe,H,H], [ZF395;F,CF₃,H,H], [ZF396;F,CN,H,H], [ZF397;Cl,H,F,H], [ZF398;Cl,H,Cl,H], [ZF399;Cl,H,Me,H], [ZF400;Cl, H₂OMe,H], [ZF401;Cl,H,CF₃,H], [ZF402;Cl,H,CN,H], [ZF403;Cl,F,H,H], [ZF404;Cl,Cl,H,H], [ZF405;Cl,Me,H, H], [ZF406;Cl,OMe,H,H], [ZF407;Cl,CF₃,H,H], [ZF408; Cl,CN,H,H], [ZF409;Me,H,F,H], [ZF410;Me,H,Cl,H], [ZF411;Me,H,Me,H], [ZF412;Me,H₂OMe,H], [ZF413;Me, H,CF₃,H], [ZF414;Me,H,CN,H], [ZF415;Me,F,H,H], [ZF416;Me,Cl,H,H], [ZF417;Me,Me,H,H], [ZF418;Me, OMe,H,H], [ZF419;Me,CF₃,H,H], [ZF420;Me,CN,H,H], [ZF421;OMe,H,F,H], [ZF422;OMe,H,Cl,H], [ZF423;OMe, H,Me,H], [ZF424;OMe,H₂OMe,H], [ZF425;OMe,H,CF₃, H], [ZF426;OMe,H,CN,H], [ZF427;OMe,F,H,H], [ZF428; OMe,Cl,H,H], [ZF429;OMe,Me,H,H], [ZF430;OMe,OMe, H,H], [ZF431;OMe,CF₃,H,H], [ZF432;OMe,CN,H,H], [ZF433;CF₃,H,F,H], [ZF434;CF₃,H,Cl,H], [ZF435;CF₃,H, Me,H], [ZF436;CF₃,H₂OMe,H], [ZF437;CF₃,H,CF₃,H], [ZF438;CF₃,H,CN,H], [ZF439;CF₃,F,H,H], [ZF440;CF₃,Cl, H,H], [ZF441;CF₃,Me,H,H], [ZF442;CF₃,OMe,H,H], [ZF443;CF₃,CF₃,H,H], [ZF444;CF₃,CN,H,H].

A compound represented by formula (1F) wherein Q represents a group represented by Q1, L represents an oxygen atom, R¹ represents a chlorine atom, and a combination of R^x16, R^x17, R^x18 and R^x19 represents any combination indicated in the combination F (hereinafter, referred to as Compound Class SX77).

A compound represented by formula (1F) wherein Q represents a group represented by Q1, L represents CH₂, R¹ represents a methyl group, and a combination of R^x16, R^x17, R^x18 and R^x19 represents any combination indicated in the combination F (hereinafter, referred to as Compound Class SX78).

A compound represented by formula (1F) wherein Q represents a group represented by Q1, L represents CH₂, R¹ represents a chlorine atom, and a combination of R^x16, R^x17, R^x18 and R^x19 represents any combination indicated in the combination F (hereinafter, referred to as Compound Class SX79).

A compound represented by formula (1F) wherein Q represents a group represented by Q1, L represents NCH₃, R¹ represents a hydrogen atom, and a combination of R^x16, R^x17, R^x18 and R^x19 represents any combination indicated in the combination F (hereinafter, referred to as Compound Class SX80).

A compound represented by formula (1F) wherein Q represents a group represented by Q2, X represents an oxygen atom, R¹ represents a methyl group, and a combination of R^x16, R^x17, R^x18 and R^x19 represents any combination indicated in the combination F (hereinafter, referred to as Compound Class SX81).

A compound represented by formula (1F) wherein Q represents a group represented by Q2, X represents an oxygen atom, R¹ represents a chlorine atom, and a combination of R^x16, R^x17, R^x18 and R^x19 represents any combination indicated in the combination F (hereinafter, referred to as Compound Class SX82).

A compound represented by formula (1F) wherein Q represents a group represented by Q2, X represents NH, R¹ represents a methyl group, and a combination of R^x16, R^x17, $R^{x18}$ and $R^{x19}$ represents any combination indicated in the combination F (hereinafter, referred to as Compound Class SX83).

A compound represented by formula (1F) wherein Q represents a group represented by Q2, X represents NH, $R^1$ represents a chlorine atom, and a combination of $R^{x16}$, $R^{x17}$, $R^{x18}$ and $R^{x19}$ represents any combination indicated in the combination F (hereinafter, referred to as Compound Class SX84).

A compound represented by formula (1F) wherein Q represents a group represented by Q3, $R^3$ represents a difluoromethyl group, $R^1$ represents a methyl group, and a combination of $R^{x16}$, $R^{x17}$, $R^{x18}$ and $R^{x19}$ represents any combination indicated in the combination F (hereinafter, referred to as Compound Class SX85).

A compound represented by formula (1F) wherein Q represents a group represented by Q3, $R^3$ represents a difluoromethyl group, $R^1$ represents a chlorine atom, and a combination of $R^{x16}$, $R^{x17}$, $R^{x18}$, and $R^{x19}$ represents any combination indicated in the combination F (hereinafter, referred to as Compound Class SX86).

A compound represented by formula (1F) wherein Q represents a group represented by Q3, $R^3$ represents a methoxy group, $R^1$ represents a methyl group, and a combination of $R^{x16}$, $R^{x17}$, $R^{x18}$ and $R^{x19}$ represents any combination indicated in the combination F (hereinafter, referred to as Compound Class SX87).

A compound represented by formula (1F) wherein Q represents a group represented by Q3, $R^3$ represents a methoxy group, $R^1$ represents a chlorine atom, and a combination of $R^{x16}$, $R^{x17}$, $R^{x18}$, and $R^{x19}$ represents any combination indicated in the combination F (hereinafter, referred to as Compound Class SX88).

A compound represented by formula (1F) wherein Q represents a group represented by Q4, $R^1$ represents a methyl group, and a combination of $R^{x16}$, $R^{x17}$, $R^{x18}$ and $R^{x19}$ represents any combination indicated in the combination F (hereinafter, referred to as Compound Class SX89).

A compound represented by formula (1F) wherein Q represents a group represented by Q4, $R^1$ represents a chlorine atom, and a combination of $R^{x16}$, $R^{x17}$, $R^{x18}$ and $R^{x19}$ represents any combination indicated in the combination F (hereinafter, referred to as Compound Class SX90).

A compound represented by formula (1G):

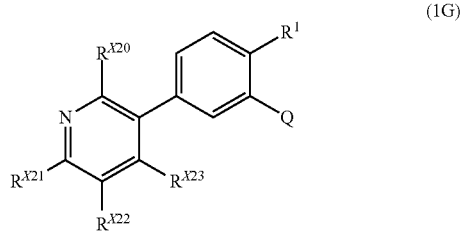

(1G)

wherein Q represents a group represented by Q1, L represents an oxygen atom, $R^1$ represents a methyl group, and a combination of $R^{x16}$, $R^{x17}$, $R^{x18}$, and $R^{x19}$ represents any combination indicated in the combination G (hereinafter, referred to as Compound Class SX91).

The combination F consists of the substituent number ZG1 to ZG389. The substituent number ZG1 to ZG389 represents any combinations of $R^{x20}$, $R^{x21}$, $R^{x22}$ and $R^{x23}$ in the compound represented formula (1G), and hereinafter, which is indicated as [Substituent Number: $R^{x20}$; $R^{x21}$; $R^{x22}$; $R^{x23}$]. For example, "Substituent Number ZG2" represents a combination where $R^{x20}$ represents a methyl group, and $R^{x21}$, $R^{x22}$, and $R^{x23}$ each is a hydrogen atom.

Combination G

[ZG1;H,H,H,H], [ZG2;Me,H,H,H], [ZG3;F,H,H,H], [ZG4;Cl,H,H,H], [ZG5;OMe,H,H,H], [ZG6;CF₃,H,H,H], [ZG7;H,Me,H,H], [ZG8;H,Et,H,H], [ZG9;H,Pr,H,H], [ZG10;H,i-Pr,H,H], [ZG11;H,t-Bu,H,H], [ZG12;H₂OMe,H,H], [ZG13;H₂OEt,H,H], [ZG14;H₂OPr,H,H], [ZG15;H₂Oi-Pr,H,H], [ZG16;H,CF₃,H,H], [ZG17;H,CF₂H,H,H], [ZG18;H,CFH₂,H,H], [ZG19;H,F,H,H], [ZG20;H,Cl,H,H], [ZG21;H,Br,H,H], [ZG22;H,CN,H,H], [ZG23;H,Ph,H,H], [ZG24;H₂OPh,H,H], [ZG25;H,c-Pr,H,H], [ZG26;H,c-Pen,H,H], [ZG27;H,c-Hex,H,H], [ZG28;H,H,Me,H], [ZG29;H,H,Et,H], [ZG30;H,H,Pr,H], [ZG31;H,H,i-Pr,H], [ZG32;H,H,t-Bu,H], [ZG33;H,H₂OMe,H], [ZG34;H,H₂OEt,H], [ZG35;H,H₂OPr,H], [ZG36;H,H₂Oi-Pr,H], [ZG37;H,H,CF₃,H], [ZG38;H,H,CF₂H,H], [ZG39;H,H,CFH₂,H], [ZG40;H,H,F,H], [ZG41;H,H,Cl,H], [ZG42;H,H,Br,H], [ZG43;H,H,CN,H], [ZG44;H,H,Ph,H], [ZG45;H,H₂OPh,H], [ZG46;H,H,c-Pr,H], [ZG47;H,H,c-Pen,H], [ZG48;H,H,c-Hex,H], [ZG49;H,H,H,H], [ZG50;H,H,H,Me], [ZG51;H,H,H,F], [ZG52;H,H,H,Cl], [ZG53;H,H,H₂OMe], [ZG54;H,H,H,CF₃], [ZG55;H,H,H,F], [ZG56;Me,H,H,F], [ZG57;F,H,H,F], [ZG58;Cl,H,H,F], [ZG59;H,Me,H,F], [ZG60;H,Et,H,F], [ZG61;H,Pr,H,F], [ZG62;H,i-Pr,H,F], [ZG63;H,t-Bu,H,F], [ZG64;H₂OMe,H,F], [ZG65;H₂OEt,H,F], [ZG66;H₂OPr,H,F], [ZG67;H₂Oi-Pr,H,F], [ZG68;H,CF₃,H,F], [ZG69;H,CF₂H,H,F], [ZG70;H,CFH₂,H,F], [ZG71;H,F,H,F], [ZG72;H,Cl,H,F], [ZG73;H,Br,H,F], [ZG74;H,CN,H,F], [ZG75;H,Ph,H,F], [ZG76;H₂OPh,H,F], [ZG77;H,c-Pr,H,F], [ZG78;H,c-Pen,H,F], [ZG79;H,c-Hex,H,F], [ZG80;H,H,Me,F], [ZG81;H,H,Et,F], [ZG82;H,H,Pr,F], [ZG83;H,H,i-Pr,F], [ZG84;H,H,t-Bu,F], [ZG85;H,H₂OMe,F], [ZG86;H,H₂OEt,F], [ZG87;H,H₂OPr,F], [ZG88;H,H₂Oi-Pr,F], [ZG89;H,H,CF₃,F], [ZG90;H,H,CF₂H,F], [ZG91;H,H,CFH₂,F], [ZG92;H,H,F,F], [ZG93;H,H,Cl,F], [ZG94;H,H,Br,F], [ZG95;H,H,CN,F], [ZG96;H,H,Ph,F], [ZG97;H,H₂OPh,F], [ZG98;H,H,c-Pr,F], [ZG99;H,H,c-Pen,F], [ZG100;H,H,c-Hex,F], [ZG101;H,H,H,Cl], [ZG102;Me,H,H,Cl], [ZG103;F,H,H,Cl], [ZG104;Cl,H,H,Cl], [ZG105;H,Me,H,Cl], [ZG106;H,Et,H,Cl], [ZG107;H,Pr,H,Cl], [ZG108;H,i-Pr,H,Cl], [ZG109;H,t-Bu,H,Cl], [ZG110;H₂OMe,H,Cl], [ZG111;H₂OEt,H,Cl], [ZG112;H₂OPr,H,Cl], [ZG113;H₂Oi-Pr,H,Cl], [ZG114;H,CF₃,H,Cl], [ZG115;H,CF₂H,H,Cl], [ZG116;H,CFH₂,H,Cl], [ZG117;H,F,H,Cl], [ZG118;H,Cl,H,Cl], [ZG119;H,Br,H,Cl], [ZG120;H,CN,H,Cl], [ZG121;H,Ph,H,Cl], [ZG122;H₂OPh,H,Cl], [ZG123;H,c-Pr,H,Cl], [ZG124;H,c-Pen,H,Cl], [ZG125;H,c-Hex,H,Cl], [ZG126;H,H,Me,Cl], [ZG127;H,H,Et,Cl], [ZG128;H,H,Pr,Cl], [ZG129;H,H,i-Pr,Cl], [ZG130;H,H,t-Bu,Cl], [ZG131;H,H₂OMe,Cl], [ZG132;H,H₂OEt,Cl], [ZG133;H,H₂OPr,Cl], [ZG134;H,H₂Oi-Pr,Cl], [ZG135;H,H,CF₃,Cl], [ZG136;H,H,CF₂H,Cl], [ZG137;H,H,CFH₂,Cl], [ZG138;H,H,F,Cl], [ZG139;H,H,Cl,Cl], [ZG140;H,H,Br,Cl], [ZG141;H,H,CN,Cl], [ZG142;H,H,Ph,Cl], [ZG143;H,H₂OPh,Cl], [ZG144;H,H,c-Pr,Cl], [ZG145;H,H,c-Pen,Cl], [ZG146;H,H,c-Hex,Cl], [ZG147;H,H,H,Me], [ZG148;Me,H,H,Me], [ZG149;F,H,H,Me], [ZG150;Cl,H,H,Me], [ZG151;H,Me,H,Me], [ZG152;H,Et,H,Me], [ZG153;H,Pr,H,Me], [ZG154;H,i-Pr,H,Me], [ZG155;H,t-Bu,H,Me], [ZG156;H₂OMe,H,Me], [ZG157;H₂OEt,H,Me], [ZG158;H₂OPr,H,Me], [ZG159;H₂Oi-Pr,H,Me], [ZG160;H,CF₃,H,Me], [ZG161;H,CF₂H,H,Me], [ZG162;H,CFH₂,H,Me], [ZG163;H,F,H,Me], [ZG164;H,Cl,H,Me], [ZG165;H,Br,H,Me], [ZG166;H,CN,H,Me], [ZG167;H,Ph,H,Me], [ZG168;H₂OPh,H,Me], [ZG169;H,c-Pr,H,Me], [ZG170;H,c-Pen,H,Me], [ZG171;H,c-Hex,H,

Me], [ZG172;H,H,Me,Me], [ZG173;H,H,Et,Me], [ZG174; H,H,Pr,Me], [ZG175;H,H,i-Pr,Me], [ZG176;H,H,t-Bu,Me], [ZG177;H,H₂OMe,Me], [ZG178;H,H₂OEt,Me], [ZG179;H, H₂OPr,Me], [ZG180;H,H₂Oi-Pr,Me], [ZG181;H,H,CF₃, Me], [ZG182;H,H,CF₂H,Me], [ZG183;H,H,CFH₂,Me], [ZG184;H,H,F,Me], [ZG185;H,H,Cl,Me], [ZG186;H,H,Br, Me], [ZG187;H,H,CN,Me], [ZG188;H,H,Ph,Me], [ZG189; H,H₂OPh,Me], [ZG190;H,H,c-Pr,Me], [ZG191;H,H,c-Pen, Me], [ZG192;H,H,c-Hex,Me], [ZG193;H,H,H₂OMe], [ZG194;Me,H,H₂OMe], [ZG195;F,H,H₂OMe], [ZG196;Cl, H,H₂OMe], [ZG197;H,Me,H₂OMe], [ZG198;H,Et, H₂OMe], [ZG199;H,Pr,H₂OMe], [ZG200;H,i-Pr,H₂OMe], [ZG201;H,t-Bu,H₂OMe], [ZG202;H₂OMe,H₂OMe], [ZG203;H₂OEt,H₂OMe], [ZG204;H₂OPr,H₂OMe], [ZG205;H₂Oi-Pr,H₂OMe], [ZG206;H,CF₃,H₂OMe], [ZG207;H,CF₂H,H₂OMe], [ZG208;H,CFH₂,H₂OMe], [ZG209;H,F,H₂OMe], [ZG210;H,Cl,H₂OMe], [ZG211;H, Br,H₂OMe], [ZG212;H,CN,H₂OMe], [ZG213;H,Ph, H₂OMe], [ZG214;H₂OPh,H₂OMe], [ZG215;H,c-Pr, H₂OMe], [ZG216;H,c-Pen,H₂OMe], [ZG217;H,c-Hex, H₂OMe], [ZG218;H,H,Me,OMe], [ZG219;H,H,Et,OMe], [ZG220;H,H,Pr,OMe], [ZG221;H,H,i-Pr,OMe], [ZG222;H, H,t-Bu,OMe], [ZG223;H,H₂OMe,OMe], [ZG224;H,H₂OEt, OMe], [ZG225;H,H₂OPr,OMe], [ZG226;H,H₂Oi-Pr,OMe], [ZG227;H,H,CF₃,OMe], [ZG228;H,H,CF₂H,OMe], [ZG229;H,H,CFH₂,OMe], [ZG230;H,H,F,OMe], [ZG231; H,H,Cl,OMe], [ZG232;H,H,Br,OMe], [ZG233;H,H,CN, OMe], [ZG234;H,H,Ph,OMe], [ZG235;H,H₂OPh,OMe], [ZG236;H,H,c-Pr,OMe], [ZG237;H,H,c-Pen,OMe], [ZG238;H,H,c-Hex,OMe], [ZG239;H,H,H,CF₃], [ZG240; Me,H,H,CF₃], [ZG241;F,H,H,CF₃], [ZG242;Cl,H,H,CF₃], [ZG243;H,Me,H,CF₃], [ZG244;H,Et,H,CF₃], [ZG245;H,Pr, H,CF₃], [ZG246;H,i-Pr,H,CF₃], [ZG247;H,t-Bu,H,CF₃], [ZG248;H₂OMe,H,CF₃], [ZG249;H₂OEt,H,CF₃], [ZG250; H₂OPr,H,CF₃], [ZG251;H₂Oi-Pr,H,CF₃], [ZG252;H,CF₃,H, CF₃], [ZG253;H,CF₂H,H,CF₃], [ZG254;H,CFH₂,H,CF₃], [ZG255;H,F,H,CF₃], [ZG256;H,Cl,H,CF₃], [ZG257;H,Br, H,CF₃], [ZG258;H,CN,H,CF₃], [ZG259;H,Ph,H,CF₃], [ZG260;H₂OPh,H,CF₃], [ZG261;H,c-Pr,H,CF₃], [ZG262; H,c-Pen,H,CF₃], [ZG263;H,c-Hex,H,CF₃], [ZG264;H,H, Me,CF₃], [ZG265;H,H,Et,CF₃], [ZG266;H,H,Pr,CF₃], [ZG267;H,H,i-Pr,CF₃], [ZG268;H,H,t-Bu,CF₃], [ZG269;H, H₂OMe,CF₃], [ZG270;H,H₂OEt,CF₃], [ZG271;H,H₂OPr, CF₃], [ZG272;H,H₂Oi-Pr,CF₃], [ZG273;H,H,CF₃,CF₃], [ZG274;H,H,CF₂H,CF₃], [ZG275;H,H,CFH₂,CF₃], [ZG276;H,H,F,CF₃], [ZG277;H,H,Cl,CF₃], [ZG278;H,H, Br,CF₃], [ZG279;H,H,CN,CF₃], [ZG280;H,H,Ph,CF₃], [ZG281;H,H₂OPh,CF₃], [ZG282;H,H,c-Pr,CF₃],[ZG283;H, H,c-Pen,CF₃], [ZG284;H,H,c-Hex,CF₃], [ZG285;H,F,Me, H], [ZG286;H,F,Et,H], [ZG287;H,F,Pr,H], [ZG288;H,F,i-Pr, H], [ZG289;H,F,t-Bu,H], [ZG290;H,F,OMe,H], [ZG291;H, F,OEt,H], [ZG292;H,F,OPr,H], [ZG293;H,F,Oi-Pr,H], [ZG294;H,F,CF₃,H], [ZG295;H,F,CF₂H,H], [ZG296;H,F, CFH₂,H], [ZG297;H,F,F,H], [ZG298;H,F,Cl,H], [ZG299;H, F,Br,H], [ZG300;H,F,CN,H], [ZG301;H,F,Ph,H], [ZG302; H,F,OPh,H], [ZG303;H,F,c-Pr,H], [ZG304;H,F,c-Pen,H], [ZG305;H,F,c-Hex,H], [ZG306;H,Cl,Me,H], [ZG307;H,Cl, Et,H], [ZG308;H,Cl,Pr,H], [ZG309;H,Cl,i-Pr,H], [ZG310; H,Cl,t-Bu,H], [ZG311;H,Cl,OMe,H], [ZG312;H,Cl,OEt,H], [ZG313;H,Cl,OPr,H], [ZG314;H,Cl,Oi-Pr,H], [ZG315;H, Cl,CF₃,H], [ZG316;H,Cl,CF₂H,H], [ZG317;H,Cl,CFH₂,H], [ZG318;H,Cl,F,H], [ZG319;H,Cl,Cl,H], [ZG320;H,Cl,Br, H], [ZG321;H,Cl,CN,H], [ZG322;H,Cl,Ph,H], [ZG323;H, Cl,OPh,H], [ZG324;H,Cl,c-Pr,H], [ZG325;H,Cl,c-Pen,H], [ZG326;H,Cl,c-Hex,H], [ZG327;H,Me,Me,H], [ZG328;H, Me,Et,H], [ZG329;H,Me,Pr,H], [ZG330;H,Me,i-Pr,H], [ZG331;H,Me,t-Bu,H], [ZG332;H,Me,OMe,H], [ZG333;H, Me,OEt,H], [ZG334;H,Me,OPr,H], [ZG335;H,Me,Oi-Pr, H], [ZG336;H,Me,CF₃,H], [ZG337;H,Me,CF₂H,H], [ZG338;H,Me,CFH₂,H], [ZG339;H,Me,F,H], [ZG340;H, Me,Cl,H], [ZG341;H,Me,Br,H], [ZG342;H,Me,CN,H], [ZG343;H,Me,Ph,H], [ZG344;H,Me,OPh,H], [ZG345;H, Me,c-Pr,H], [ZG346;H,Me,c-Pen,H], [ZG347;H,Me,c-Hex, H], [ZG348;H₂OMe,Me,H], [ZG349;H₂OMe,Et,H], [ZG350;H₂OMe,Pr,H], [ZG351;H₂OMe,i-Pr,H], [ZG352; H₂OMe,t-Bu,H], [ZG353;H₂OMe,OMe,H], [ZG354; H₂OMe,OEt,H], [ZG355;H₂OMe,OPr,H], [ZG356;H₂OMe, Oi-Pr,H], [ZG357;H₂OMe,CF₃,H], [ZG358;H₂OMe,CF₂H, H], [ZG359;H₂OMe,CFH₂,H], [ZG360;H₂OMe,F,H], [ZG361;H₂OMe,Cl,H], [ZG362;H₂OMe,Br,H], [ZG363; H₂OMe,CN,H], [ZG364;H₂OMe,Ph,H], [ZG365;H₂OMe, OPh,H], [ZG366;H₂OMe,c-Pr,H], [ZG367;H₂OMe,c-Pen, H], [ZG368;H₂OMe,c-Hex,H], [ZG369;H,CF₃,Me,H], [ZG370;H,CF₃,Et,H], [ZG371;H,CF₃,Pr,H], [ZG372;H, CF₃,i-Pr,H], [ZG373;H,CF₃,t-Bu,H], [ZG374;H,CF₃,OMe, H], [ZG375;H,CF₃,OEt,H], [ZG376;H,CF₃,OPr,H], [ZG377;H,CF₃,Oi-Pr,H], [ZG378;H,CF₃,CF₃,H], [ZG379; H,CF₃,CF₂H,H], [ZG380;H,CF₃,CFH₂,H], [ZG381;H,CF₃, F,H], [ZG382;H,CF₃,Cl,H], [ZG383;H,CF₃,Br,H], [ZG384; H,CF₃,CN,H], [ZG385;H,CF₃,Ph,H], [ZG386;H,CF₃,OPh, H], [ZG387;H,CF₃,c-Pr,H], [ZG388;H,CF₃,c-Pen,H], [ZG389;H,CF₃,c-Hex,H].

A compound represented by formula (1G) wherein Q represents a group represented by Q1, L represents an oxygen atom, R¹ represents a chlorine atom, and a combination of $R^{x20}$, $R^{x21}$, $R^{x22}$, and $R^{x23}$ represents any combination indicated in the combination G (hereinafter, referred to as Compound Class SX92).

A compound represented by formula (1G) wherein Q represents a group represented by Q1, L represents CH₂, R¹ represents a methyl group, and a combination of $R^{x20}$, $R^{x21}$, $R^{x22}$, and $R^{x23}$ represents any combination indicated in the combination G (hereinafter, referred to as Compound Class SX93).

A compound represented by formula (1G) wherein Q represents a group represented by Q1, L represents CH₂, R¹ represents a chlorine atom, and a combination of $R^{x20}$, $R^{x21}$, $R^{x22}$, and $R^{x23}$ represents any combination indicated in the combination G (hereinafter, referred to as Compound Class SX94).

A compound represented by formula (1G) wherein Q represents a group represented by Q1, L represents NCH₃, R¹ represents a hydrogen atom, and a combination of $R^{x20}$, $R^{x21}$, $R^{x22}$, and $R^{x23}$ represents any combination indicated in the combination G (hereinafter, referred to as Compound Class SX95).

A compound represented by formula (1G) wherein Q represents a group represented by Q2, X represents an oxygen atom, R¹ represents a methyl group, and a combination of $R^{x20}$, $R^{x21}$, $R^{x22}$, and $R^{x23}$ represents any combination indicated in the combination G (hereinafter, referred to as Compound Class SX96).

A compound represented by formula (1G) wherein Q represents a group represented by Q2, X represents an oxygen atom, R¹ represents a chlorine atom, and a combination of $R^{x20}$, $R^{x21}$, $R^{x22}$, and $R^{x23}$ represents any combination indicated in the combination G (hereinafter, referred to as Compound Class SX97).

A compound represented by formula (1G) wherein Q represents a group represented by Q2, X represents NH, R¹ represents a methyl group, and a combination of $R^{x20}$, $R^{x21}$, $R^{x22}$, and $R^{x23}$ represents any combination indicated in the combination G (hereinafter, referred to as Compound Class SX98).

A compound represented by formula (1G) wherein Q represents a group represented by Q2, X represents NH, $R^1$ represents a chlorine atom, and a combination of $R^{x20}$, $R^{x21}$, $R^{x22}$, and $R^{x23}$ represents any combination indicated in the combination G (hereinafter, referred to as Compound Class SX99).

A compound represented by formula (1G) wherein Q represents a group represented by Q3, $R^3$ represents a difluoromethyl group, $R^1$ represents a methyl group, and a combination of $R^{x20}$, $R^{x21}$, $R^{x22}$, and $R^{x23}$ represents any combination indicated in the combination G (hereinafter, referred to as Compound Class SX100).

A compound represented by formula (1G) wherein Q represents a group represented by Q3, $R^3$ represents a difluoromethyl group, $R^1$ represents a chlorine atom, and a combination of $R^{x20}$, $R^{x21}$, $R^{x22}$, and $R^{x23}$ represents any combination indicated in the combination G (hereinafter, referred to as Compound Class SX101).

A compound represented by formula (1G) wherein Q represents a group represented by Q3, $R^3$ represents a methoxy group, $R^1$ represents a methyl group, and a combination of $R^{x20}$, $R^{x21}$, $R^{x22}$, and $R^{x23}$ represents any combination indicated in the combination G (hereinafter, referred to as Compound Class SX102).

A compound represented by formula (1G) wherein Q represents a group represented by Q3, $R^3$ represents a methoxy group, $R^1$ represents a chlorine atom, and a combination of $R^{x20}$, $R^{x21}$, $R^{x22}$, and $R^{x23}$ represents any combination indicated in the combination G (hereinafter, referred to as Compound Class SX103).

A compound represented by formula (1G) wherein Q represents a group represented by Q4, $R^1$ represents a methyl group, and a combination of $R^{x20}$, $R^{x21}$, $R^{x22}$, and $R^{x23}$ represents any combination indicated in the combination G (hereinafter, referred to as Compound Class SX104).

A compound represented by formula (1G) wherein Q represents a group represented by Q4, $R^1$ represents a chlorine atom, and a combination of $R^{x20}$, $R^{x21}$, $R^{x22}$, and $R^{x23}$ represents any combination indicated in the combination G (hereinafter, referred to as Compound Class SX105).

A compound represented by formula (1H):

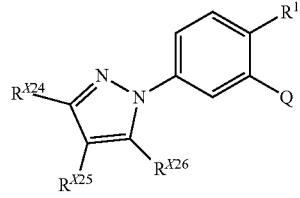

(1H)

wherein Q represents a group represented by Q1, L represents an oxygen atom, $R^1$ represents a methyl group, and a combination of $R^{x24}$, $R^{x25}$, and $R^{x26}$ represents any combination indicated in the combination H (hereinafter, referred to as Compound Class SX106).

The combination H consists of the substituent number ZH1 to ZH238. The substituent number ZH1 to ZH238 represents any combinations of $R^{x24}$, $R^{x25}$, and $R^{x26}$ in the compound represented formula (1H), and hereinafter, which is indicated as [Substituent Number: $R^{x24}$; $R^{x25}$; $R^{x26}$]. For example, "Substituent Number ZH2" represents a combination where $R^{x24}$ represents a methyl group, and $R^{x25}$, and $R^{x26}$ each is a hydrogen atom.

Combination H

[ZH1;H,H,H], [ZH2;Me,H,H], [ZH3;Et,H,H], [ZH4;t-Bu,H,H], [ZH5;OMe,H,H], [ZH6;OEt,H,H], [ZH7;CF$_3$,H,H], [ZH8;CF$_2$H,H,H], [ZH9;CFH$_2$,H,H], [ZH10;F,H,H], [ZH11;Cl,H,H], [ZH12;Br,H,H], [ZH13;CN,H,H], [ZH14;Ph,H,H], [ZH15;OPh,H,H], [ZH16;c-Pr,H,H], [ZH17;c-Pen,H,H], [ZH18;c-Hex,H,H], [ZH19;H,H,H], [ZH20;H,Me,H], [ZH21;H,Et,H], [ZH22;H,t-Bu,H], [ZH23;H$_2$OMe,H], [ZH24;H$_2$OEt,H], [ZH25;H,CF$_3$,H], [ZH26;H,CF$_2$H,H], [ZH27;H,CFH$_2$,H], [ZH28;H,F,H], [ZH29;H,Cl,H], [ZH30;H,Br,H], [ZH31;H,CN,H], [ZH32;H,Ph,H], [ZH33;H$_2$OPh,H], [ZH34;H,c-Pr,H], [ZH35;H,c-Pen,H], [ZH36;H,c-Hex,H], [ZH37;H,H,F], [ZH38;Me,H,F], [ZH39;Et,H,F], [ZH40;t-Bu,H,F], [ZH41;OMe,H,F], [ZH42;OEt,H,F], [ZH43;CF$_3$,H,F], [ZH44;CF$_2$H,H,F], [ZH45;CFH$_2$,H,F], [ZH46;F,H,F], [ZH47;Cl,H,F], [ZH48;Br,H,F], [ZH49;CN,H,F], [ZH50;Ph,H,F], [ZH51;OPh,H,F], [ZH52;c-Pr,H,F], [ZH53;c-Pen,H,F], [ZH54;c-Hex,H,F], [ZH55;H,H,F], [ZH56;H,Me,F], [ZH57;H,Et,F], [ZH58;H,t-Bu,F], [ZH59;H$_2$OMe,F], [ZH60;H$_2$OEt,F], [ZH61;H,CF$_3$,F], [ZH62;H,CF$_2$H,F], [ZH63;H,CFH$_2$,F], [ZH64;H,F,F], [ZH65;H,Cl,F], [ZH66;H,Br,F], [ZH67;H,CN,F], [ZH68;H,Ph,F], [ZH69;H$_2$OPh,F], [ZH70;H,c-Pr,F], [ZH71;H,c-Pen,F], [ZH72;H,c-Hex,F], [ZH73;H,H,Cl], [ZH74;Me,H,Cl], [ZH75;Et,H,Cl], [ZH76;t-Bu,H,Cl], [ZH77;OMe,H,Cl], [ZH78;OEt,H,Cl], [ZH79;CF$_3$,H,Cl], [ZH80;CF$_2$H,H,Cl], [ZH81;CFH$_2$,H,Cl], [ZH82;F,H,Cl], [ZH83;Cl,H,Cl], [ZH84;Br,H,Cl], [ZH85;CN,H,Cl], [ZH86;Ph,H,Cl], [ZH87;OPh,H,Cl], [ZH88;c-Pr,H,Cl], [ZH89;c-Pen,H,Cl], [ZH90;c-Hex,H,Cl], [ZH91;H,H,Cl], [ZH92;H,Me,Cl], [ZH93;H,Et,Cl], [ZH94;H,t-Bu,Cl], [ZH95;H$_2$OMe,Cl], [ZH96;H$_2$OEt,Cl], [ZH97;H,CF$_3$,Cl], [ZH98;H,CF$_2$H,Cl], [ZH99;H,CFH$_2$,Cl], [ZH100;H,F,Cl], [ZH101;H,Cl,Cl], [ZH102;H,Br,Cl], [ZH103;H,CN,Cl], [ZH104;H,Ph,Cl], [ZH105;H$_2$OPh,Cl], [ZH106;H,c-Pr,Cl], [ZH107;H,c-Pen,Cl], [ZH108;H,c-Hex,Cl], [ZH109;H,H,Me], [ZH110;Me,H,Me], [ZH111;Et,H,Me], [ZH112;t-Bu,H,Me], [ZH113;OMe,H,Me], [ZH114;OEt,H,Me], [ZH115;CF$_3$,H,Me], [ZH116;CF$_2$H,H,Me], [ZH117;CFH$_2$,H,Me], [ZH118;F,H,Me], [ZH119;Cl,H,Me], [ZH120;Br,H,Me], [ZH121;CN,H,Me], [ZH122;Ph,H,Me], [ZH123;OPh,H,Me], [ZH124;c-Pr,H,Me], [ZH125;c-Pen,H,Me], [ZH126;c-Hex,H,Me], [ZH127;H,H,Me], [ZH128;H,Me,Me], [ZH129;H,Et,Me], [ZH130;H,t-Bu,Me], [ZH131;H$_2$OMe,Me], [ZH132;H$_2$OEt,Me], [ZH133;H,CF$_3$,Me], [ZH134;H,CF$_2$H,Me], [ZH135;H,CFH$_2$,Me], [ZH136;H,F,Me], [ZH137;H,Cl,Me], [ZH138;H,Br,Me], [ZH139;H,CN,Me], [ZH140;H,Ph,Me], [ZH141;H$_2$OPh,Me], [ZH142;H,c-Pr,Me], [ZH143;H,c-Pen,Me], [ZH144;H,c-Hex,Me], [ZH145;H,H$_2$OMe], [ZH146;Me,H$_2$OMe], [ZH147;Et,H$_2$OMe], [ZH148;t-Bu,H$_2$OMe], [ZH149;OMe,H$_2$OMe], [ZH150;OEt,H$_2$OMe], [ZH151;CF$_3$,H$_2$OMe], [ZH152;CF$_2$H,H$_2$OMe], [ZH153;CFH$_2$,H$_2$OMe], [ZH154;F,H$_2$OMe], [ZH155;Cl,H$_2$OMe], [ZH156;Br,H$_2$OMe], [ZH157;CN,H$_2$OMe], [ZH158;Ph,H$_2$OMe], [ZH159;OPh,H$_2$OMe], [ZH160;c-Pr,H$_2$OMe], [ZH161;c-Pen,H$_2$OMe], [ZH162;c-Hex,H$_2$OMe], [ZH163;H,H$_2$OMe], [ZH164;H,Me,OMe], [ZH165;H,Et,OMe], [ZH166;H,t-Bu,OMe], [ZH167;H$_2$OMe,OMe], [ZH168;H$_2$OEt,OMe], [ZH169;H,CF$_3$,OMe], [ZH170;H,CF$_2$H$_2$OMe], [ZH171;H,CFH$_2$,OMe], [ZH172;H,F,OMe], [ZH173;H,Cl,OMe], [ZH174;H,Br,OMe], [ZH175;H,CN,OMe], [ZH176;H,Ph,OMe], [ZH177;H$_2$OPh,OMe], [ZH178;H,c-Pr,OMe], [ZH179;H,c-Pen,OMe], [ZH180;H,c-Hex,OMe], [ZH181;H,H,CF$_3$], [ZH182;Me,H,CF$_3$], [ZH183;Et,H,CF$_3$], [ZH184;t-Bu,H,CF$_3$], [ZH185;OMe,H,CF$_3$], [ZH186;OEt,H,CF$_3$], [ZH187;CF$_3$,H,CF$_3$], [ZH188;CF$_2$H,H,CF$_3$], [ZH189;CFH$_2$,H,CF$_3$], [ZH190;F,H,CF$_3$], [ZH191;Cl,H,CF$_3$], [ZH192;Br,H,CF$_3$], [ZH193;CN,H,CF$_3$], [ZH194;Ph,H,CF$_3$], [ZH195;OPh,H,

CF$_3$], [ZH196;c-Pr,H,CF$_3$], [ZH197;c-Pen,H,CF$_3$], [ZH198; c-Hex,H,CF$_3$], [ZH199;H,H,CF$_3$], [ZH200;H,Me,CF$_3$], [ZH201;H,Et,CF$_3$], [ZH202;H,t-Bu,CF$_3$], [ZH203;H$_2$OMe, CF$_3$], [ZH204;H$_2$OEt,CF$_3$], [ZH205;H,CF$_3$,CF$_3$], [ZH206; H,CF$_2$H,CF$_3$], [ZH207;H,CFH$_2$,CF$_3$], [ZH208;H,F,CF$_3$], [ZH209;H,Cl,CF$_3$], [ZH210;H,Br,CF$_3$], [ZH211;H,CN, CF$_3$], [ZH212;H,Ph,CF$_3$], [ZH213;H$_2$OPh,CF$_3$], [ZH214;H, c-Pr,CF$_3$], [ZH215;H,c-Pen,CF$_3$], [ZH216;H,c-Hex,CF$_3$], [ZH217;Me,Me,H], [ZH218;Me,F,H], [ZH219;Me,Cl,H], [ZH220;Me,OMe,H], [ZH221;Me,CF$_3$,H], [ZH222;Me,CN, H], [ZH223;F,Me,H], [ZH224;Cl,Me,H], [ZH225;OMe,Me, H], [ZH226;CF$_3$,Me,H], [ZH227;CN,Me,H], [ZH228;Me, Me,Me], [ZH229;Me,F,Me], [ZH230;Me,Cl,Me], [ZH231; Me,OMe,Me], [ZH232;Me,CF$_3$,Me], [ZH233;Me,CN,Me], [ZH234;F,Me,Me], [ZH235;Cl,Me,Me], [ZH236;OMe,Me, Me], [ZH237;CF$_3$,Me,Me], [ZH238;CN,Me,Me].

A compound represented by formula (1H) wherein Q represents a group represented by Q1, L represents an oxygen atom, R$^1$ represents a chlorine atom, and a combination of R$^{x24}$, R$^{x25}$, and R$^{x26}$ represents any combination indicated in the combination H (hereinafter, referred to as Compound Class SX107).

A compound represented by formula (1H) wherein Q represents a group represented by Q1, L represents an oxygen atom, R$^1$ represents a methyl group, and a combination of R$^{x24}$, R$^{x25}$, and R$^{x26}$ represents any combination indicated in the combination H (hereinafter, referred to as Compound Class SX108).

A compound represented by formula (1H) wherein Q represents a group represented by Q1, L represents an oxygen atom, R$^1$ represents a chlorine atom, and a combination of R$^{x24}$, R$^{x25}$, and R$^{x26}$ represents any combination indicated in the combination H (hereinafter, referred to as Compound Class SX109).

A compound represented by formula (1H) wherein Q represents a group represented by Q1, L represents NCH$_3$, R$^1$ represents a hydrogen atom, and a combination of R$^{x24}$, R$^{x25}$, and R$^{x26}$ represents any combination indicated in the combination H (hereinafter, referred to as Compound Class SX110).

A compound represented by formula (1H) wherein Q represents a group represented by Q2, X represents an oxygen atom, R$^1$ represents a methyl group, and a combination of R$^{x24}$, R$^{x25}$, and R$^{x26}$ represents any combination indicated in the combination H (hereinafter, referred to as Compound Class SX111).

A compound represented by formula (1H) wherein Q represents a group represented by Q2, X represents an oxygen atom, R$^1$ represents a chlorine atom, and a combination of R$^{x24}$, R$^{x25}$, and R$^{x26}$ represents any combination indicated in the combination H (hereinafter, referred to as Compound Class SX112).

A compound represented by formula (1H) wherein Q represents a group represented by Q2, X represents NH, R$^1$ represents a methyl group, and a combination of R$^{x24}$, R$^{x25}$, and R$^{x26}$ represents any combination indicated in the combination H (hereinafter, referred to as Compound Class SX113).

A compound represented by formula (1H) wherein Q represents a group represented by Q2, X represents NH, R$^1$ represents a chlorine atom, and a combination of R$^{x24}$, R$^{x25}$, and R$^{x26}$ represents any combination indicated in the combination H (hereinafter, referred to as Compound Class SX114).

A compound represented by formula (1H) wherein Q represents a group represented by Q3, R$^3$ represents a difluoromethyl group, R$^1$ represents a methyl group, and a combination of R$^{x24}$, R$^{x25}$, and R$^{x26}$ represents any combination indicated in the combination H (hereinafter, referred to as Compound Class SX115).

A compound represented by formula (1H) wherein Q represents a group represented by Q3, R$^3$ represents a difluoromethyl group, R$^1$ represents a chlorine atom, and a combination of R$^{x24}$, R$^{x25}$, and R$^{x26}$ represents any combination indicated in the combination H (hereinafter, referred to as Compound Class SX116).

A compound represented by formula (1H) wherein Q represents a group represented by Q3, R$^3$ represents a methoxy group, R$^1$ represents a methyl group, and a combination of R$^{x24}$, R$^{x25}$, and R$^{x26}$ represents any combination indicated in the combination H (hereinafter, referred to as Compound Class SX117).

A compound represented by formula (1H) wherein Q represents a group represented by Q3, R$^3$ represents a methoxy group, R$^1$ represents a chlorine atom, and a combination of R$^{x24}$, R$^{x25}$, and R$^{x26}$ represents any combination indicated in the combination H (hereinafter, referred to as Compound Class SX118).

A compound represented by formula (1H) wherein Q represents a group represented by Q4, R$^1$ represents a methyl group, and a combination of R$^{x24}$, R$^{x25}$, and R$^{x26}$ represents any combination indicated in the combination H (hereinafter, referred to as Compound Class SX119).

A compound represented by formula (1H) wherein Q represents a group represented by Q4, R$^1$ represents a chlorine atom, and a combination of R$^{x24}$, R$^{x25}$, and R$^{x26}$ represents any combination indicated in the combination H (hereinafter, referred to as Compound Class SX120).

A compound represented by formula (1I):

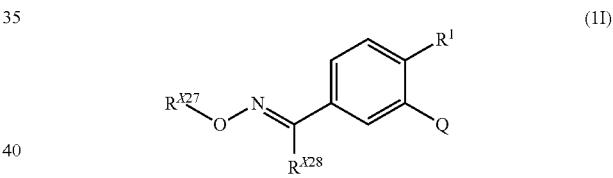

(1I)

wherein Q represents a group represented by Q1, L represents an oxygen atom, R$^1$ represents a methyl group, and a combination of R$^{x27}$ and R$^{x28}$ represents any combination indicated in the combination I (hereinafter, referred to as Compound Class SX121).

The combination I consists of the substituent number ZI1 to ZI534. The substituent number ZI1 to ZI534 represents any combinations of R$^{x27}$ and R$^{x28}$ in the compound represented formula (1I), and hereinafter, which is indicated as [Substituent Number: R$^{x27}$; R$^{x28}$]. For example, "Substituent Number ZI2" represents a combination where R$^{x27}$ represents an ethyl group, and R$^{x28}$ is a hydrogen atom.

Combination I
[ZI1;Me,H], [ZI2;Et,H], [ZI3;Pr,H], [ZI4;Bu,H], [ZI5;Pen, H], [ZI6;Hex,H], [ZI7;i-Pr,H], [ZI8;i-Bu,H], [ZI9;t-Bu,H], [ZI10;c-Pr,H], [ZI11;c-Bu,H], [ZI12;c-Pen,H], [ZI13;c-Hex, H], [ZI14;CH$_2$c-Pr,H], [ZI15;CH$_2$c-Pen,H], [ZI16;CH$_2$c-Hex,H], [ZI17;CH$_2$CH=CH$_2$,H], [ZI18;CH$_2$CH=CHMe, H], [ZI19;CH$_2$CH=CMe$_2$,H], [ZI20;CH$_2$CCH,H], [ZI21; CH$_2$CCMe,H], [ZI22;CH$_2$Ph,H], [ZI23;CH$_2$(2-F-Ph),H], [ZI24;CH$_2$(3-F-Ph),H], [ZI25;CH$_2$(4-F-Ph),H], [ZI26;CH$_2$ (2-Cl-Ph),H], [ZI27;CH$_2$(3-Cl-Ph),H], [ZI28;CH$_2$(4-Cl-Ph), H], [ZI29;CH$_2$(2-Br-Ph),H], [ZI30;CH$_2$(3-Br-Ph),H], [ZI31; CH$_2$(4-Br-Ph),H], [ZI32;CH$_2$(2-Me-Ph),H], [ZI33;CH$_2$(3-Me-Ph),H], [ZI34;CH$_2$(4-Me-Ph),H], [ZI35;CH$_2$(2-Et-Ph), H], [ZI36;CH₂(3-Et-Ph),H], [ZI37;CH₂(4-Et-Ph),H], [ZI38; CH₂(2-t-Bu-Ph),H], [ZI39;CH₂(3-t-Bu-Ph),H], [ZI40;CH₂ (4-t-Bu-Ph),H], [ZI41;CH₂(2-CF₃-Ph),H], [ZI42;CH₂(3-CF₃-Ph),H], [ZI43;CH₂(4-CF₃-Ph),H], [ZI44;CH₂(2-OMe-Ph),H], [ZI45;CH₂(3-OMe-Ph),H], [ZI46;CH₂(4-OMe-Ph), H], [ZI47;CH₂(2-SMe-Ph),H], [ZI48;CH₂(3-SMe-Ph),H], [ZI49;CH₂(4-SMe-Ph),H], [ZI50;CH₂(2-CN-Ph),H], [ZI51; CH₂(3-CN-Ph),H], [ZI52;CH₂(4-CN-Ph),H], [ZI53;CH₂(2,4-F₂-Ph),H], [ZI54;CH₂(2,5-F₂-Ph),H], [ZI55;CH₂(3,4-F₂-Ph),H], [ZI56;CH₂(3,5-F₂-Ph),H], [ZI57;CH₂(2,4-Cl₂-Ph), H], [ZI58;CH₂(2,5-Cl₂-Ph),H], [ZI59;CH₂(3,4-Cl₂-Ph),H], [ZI60;CH₂(3,5-Cl₂-Ph),H], [ZI61;CH₂(2,4-Me₂-Ph),H], [ZI62;CH₂(2,5-Me₂-Ph),H], [ZI63;CH₂(3,4-Me₂-Ph),H], [ZI64;CH₂(3,5-Me₂-Ph),H], [ZI65;CH₂(2-F-4-Cl-Ph),H], [ZI66;CH₂(2-Cl-4-F-Ph),H], [ZI67;CH₂(2-F-4-Me-Ph),H], [ZI68;CH₂(2-Me-4-F-Ph),H], [ZI69;CH₂(2-F-4-OMe-Ph), H], [ZI70;CH₂(2-OMe-4-F-Ph),H], [ZI71;CH₂(2-Me-4-Cl-Ph),H], [ZI72;CH₂(2-Cl-4-Me-Ph),H], [ZI73;CH₂(2-Me-4-OMe-Ph),H], [ZI74;CH₂(2-OMe-4-Me-Ph),H], [ZI75;CH₂ (2-Cl-4-OMe-Ph),H], [ZI76;CH₂(2-OMe-4-Cl-Ph),H], [ZI77;CH₂(2,4,6-F₃-Ph),H], [ZI78;CH₂(3,4,5-F₃-Ph),H], [ZI79;CH₂(2-pyridyl),H], [ZI80;CH₂(3-pyridyl),H], [ZI81; CH₂(4-pyridyl),H], [ZI82;CH₂(3-F-pyridin-2-yl),H], [ZI83; CH₂(4-F-pyridin-2-yl),H], [ZI84;CH₂(5-F-pyridin-2-yl),H], [ZI85;CH₂(6-F-pyridin-2-yl),H], [ZI86;CH₂(3-Cl-pyridin-2-yl),H], [ZI87;CH₂(4-Cl-pyridin-2-yl),H], [ZI88;CH₂(5-Cl-pyridin-2-yl),H], [ZI89;CH₂(6-Cl-pyridin-2-yl),H], [ZI90;CH₂(3-Me-pyridin-2-yl),H], [ZI91;CH₂(4-Me-pyridin-2-yl),H], [ZI92;CH₂(5-Me-pyridin-2-yl),H], [ZI93;CH₂ (6-Me-pyridin-2-yl),H], [ZI94;CH₂(3-OMe-pyridin-2-yl), H], [ZI95;CH₂(4-OMe-pyridin-2-yl),H], [ZI96;CH₂(5-OMe-pyridin-2-yl),H], [ZI97;CH₂(6-OMe-pyridin-2-yl),H], [ZI98;CH₂(3-CF₃-pyridin-2-yl),H], [ZI99;CH₂(4-CF₃-pyridin-2-yl),H], [ZI100;CH₂(5-CF₃-pyridin-2-yl),H], [ZI101; CH₂(6-CF₃-pyridin-2-yl),H], [ZI102;CH₂(3-CN-pyridin-2-yl),H], [ZI103;CH₂(4-CN-pyridin-2-yl),H], [ZI104;CH₂(5-CN-pyridin-2-yl),H], [ZI105;CH₂(6-CN-pyridin-2-yl),H], [ZI106;CH₂(2-F-pyridin-3-yl),H], [ZI107;CH₂(4-F-pyridin-3-yl),H], [ZI108;CH₂(5-F-pyridin-3-yl),H], [ZI109;CH₂(6-F-pyridin-3-yl),H], [ZI110;CH₂(2-Cl-pyridin-3-yl),H], [ZI111;CH₂(4-Cl-pyridin-3-yl),H], [ZI112;CH₂(5-Cl-pyridin-3-yl),H], [ZI113;CH₂(6-Cl-pyridin-3-yl),H], [ZI114; CH₂(2-Me-pyridin-3-yl),H], [ZI115;CH₂(4-Me-pyridin-3-yl),H], [ZI116;CH₂(5-Me-pyridin-3-yl),H], [ZI117;CH₂(6-Me-pyridin-3-yl),H], [ZI118;CH₂(2-OMe-pyridin-3-yl),H], [ZI119;CH₂(4-OMe-pyridin-3-yl),H], [ZI120;CH₂(5-OMe-pyridin-3-yl),H], [ZI121;CH₂(6-OMe-pyridin-3-yl),H], [ZI122;CH₂(2-CF₃-pyridin-3-yl),H], [ZI123;CH₂(4-CF₃-pyridin-3-yl),H], [ZI124;CH₂(5-CF₃-pyridin-3-yl),H], [ZI125;CH₂(6-CF₃-pyridin-3-yl),H], [ZI126;CH₂(2-CN-pyridin-3-yl),H], [ZI127;CH₂(4-CN-pyridin-3-yl),H], [ZI128;CH₂(5-CN-pyridin-3-yl),H], [ZI129;CH₂(6-CN-pyridin-3-yl),H], [ZI130;CH₂(2-F-pyridin-4-yl),H], [ZI131; CH₂(3-F-pyridin-4-yl),H], [ZI132;CH₂(2-Cl-pyridin-4-yl), H], [ZI133;CH₂(3-Cl-pyridin-4-yl),H], [ZI134;CH₂(2-Me-pyridin-4-yl),H], [ZI135;CH₂(3-Me-pyridin-4-yl),H], [ZI136;CH₂(2-OMe-pyridin-4-yl),H], [ZI137;CH₂(3-OMe-pyridin-4-yl),H], [ZI138;CH₂(2-CF₃-pyridin-4-yl),H], [ZI139;CH₂(3-CF₃-pyridin-4-yl),H], [ZI140;CH₂(2-CN-pyridin-4-yl),H], [ZI141;CH₂(3-CN-pyridin-4-yl),H], [ZI142;CH₂(2-Thienyl),H], [ZI143;CH₂(3-Thienyl),H], [ZI144;CH₂(2-pyrimidinyl),H], [ZI145;CH₂(4-pyrimidinyl),H], [ZI146;CH₂(5-pyrimidinyl),H], [ZI147;CH₂(3-pyridazinyl),H], [ZI148;CH₂(4-pyridazinyl),H], [ZI149; (CH₂)₂Ph,H], [ZI150; (CH₂)₃Ph,H], [ZI151;CH₂OMe,H], [ZI152;CH₂OEt,H], [ZI153;CH₂OPr,H], [ZI154;CH₂OPh, H], [ZI155;CH₂CN,H], [ZI156;Ph,H], [ZI157;2-F-Ph,H], [ZI158;3-F-Ph,H],[ZI159;4-F-Ph,H], [ZI160;2-Cl-Ph,H], [ZI161;3-Cl-Ph,H], [ZI162;4-Cl-Ph,H], [ZI163;2-Me-Ph, H], [ZI164;3-Me-Ph,H], [ZI165;4-Me-Ph,H], [ZI166;2-OMe-Ph,H], [ZI167;3-OMe-Ph,H], [ZI168;4-OMe-Ph,H], [ZI169;2-Pyridyl,H], [ZI170;3-Pyridyl,H], [ZI171;4-Pyridyl,H], [ZI172;2-Thienyl,H], [ZI173;3-Thienyl,H], [ZI174;2-pyrimidinyl,H], [ZI175;4-pyrimidinyl,H], [ZI176; 5-pyrimidinyl,H], [ZI177;3-pyridazinyl,H], [ZI178;4-pyridazinyl,H], [ZI179;Me,Me], [ZI180;Et,Me], [ZI181;Pr, Me], [ZI182;Bu,Me], [ZI183;Pen,Me], [ZI184;Hex,Me], [ZI185;i-Pr,Me], [ZI186;i-Bu,Me], [ZI187;t-Bu,Me], [ZI188;c-Pr,Me], [ZI189;c-Bu,Me], [ZI190;c-Pen,Me], [ZI191;c-Hex,Me], [ZI192;CH₂c-Pr,Me], [ZI193;CH₂c-Pen,Me],[ZI194;CH₂c-Hex,Me], [ZI195;CH₂CH=CH2, Me], [ZI196;CH₂CH=CHMe,Me], [ZI197; CH₂CH=CMe₂,Me], [ZI198;CH₂C≡CH,Me], [ZI199; CH₂C≡CMe,Me], [ZI200;CH₂Ph,Me], [ZI201;CH₂(2-F-Ph),Me], [ZI202;CH₂(3-F-Ph),Me], [ZI203;CH₂(4-F-Ph), Me], [ZI204;CH₂(2-Cl-Ph),Me], [ZI205;CH₂(3-Cl-Ph),Me], [ZI206;CH₂(4-Cl-Ph),Me], [ZI207;CH₂(2-Br-Ph),Me], [ZI208;CH₂(3-Br-Ph),Me], [ZI209;CH₂(4-Br-Ph),Me], [ZI210;CH₂(2-Me-Ph),Me], [ZI211;CH₂(3-Me-Ph),Me], [ZI212;CH₂(4-Me-Ph),Me], [ZI213;CH₂(2-Et-Ph),Me], [ZI214;CH₂(3-Et-Ph),Me], [ZI215;CH₂(4-Et-Ph),Me], [ZI216;CH₂(2-t-Bu-Ph),Me], [ZI217;CH₂(3-t-Bu-Ph),Me], [ZI218;CH₂(4-t-Bu-Ph),Me], [ZI219;CH₂(2-CF₃-Ph),Me], [ZI220;CH₂(3-CF₃-Ph),Me], [ZI221;CH₂(4-CF₃-Ph),Me], [ZI222;CH₂(2-OMe-Ph),Me], [ZI223;CH₂(3-OMe-Ph), Me], [ZI224;CH₂(4-OMe-Ph),Me], [ZI225;CH₂(2-SMe-Ph),Me], [ZI226;CH₂(3-SMe-Ph),Me], [ZI227;CH₂(4-SMe-Ph),Me], [ZI228;CH₂(2-CN-Ph),Me], [ZI229;CH₂(3-CN-Ph),Me], [ZI230;CH₂(4-CN-Ph),Me], [ZI231;CH₂(2,4-F₂-Ph),Me], [ZI232;CH₂(2,5-F₂-Ph),Me], [ZI233;CH₂(3,4-F₂-Ph),Me], [ZI234;CH₂(3,5-F₂-Ph),Me], [ZI235;CH₂(2,4-Cl₂-Ph),Me], [ZI236;CH₂(2,5-Cl₂-Ph),Me], [ZI237;CH₂(3,4-Cl₂-Ph),Me], [ZI238;CH₂(3,5-Cl₂-Ph),Me], [ZI239;CH₂(2,4-Me₂-Ph),Me], [ZI240;CH₂(2,5-Me₂-Ph),Me], [ZI241; CH₂(3,4-Me₂-Ph),Me], [ZI242;CH₂(3,5-Me₂-Ph),Me], [ZI243;CH₂(2-F-4-Cl-Ph),Me], [ZI244;CH₂(2-Cl-4-F-Ph), Me], [ZI245;CH₂(2-F-4-Me-Ph),Me], [ZI246;CH₂(2-Me-4-F-Ph),Me], [ZI247;CH₂(2-F-4-OMe-Ph),Me], [ZI248;CH₂ (2-OMe-4-F-Ph),Me], [ZI249;CH₂(2-Me-4-Cl-Ph),Me], [ZI250;CH₂(2-Cl-4-Me-Ph),Me], [ZI251;CH₂(2-Me-4-OMe-Ph),Me], [ZI252;CH₂(2-OMe-4-Me-Ph),Me], [ZI253; CH₂(2-Cl-4-OMe-Ph),Me], [ZI254;CH₂(2-OMe-4-Cl-Ph), Me], [ZI255;CH₂(2,4,6-F₃-Ph),Me], [ZI256;CH₂(3,4,5-F₃-Ph),Me], [ZI257;CH₂(2-pyridyl),Me], [ZI258;CH₂(3-pyridyl),Me], [ZI259;CH₂(4-pyridyl),Me], [ZI260;CH₂(3-F-pyridin-2-yl),Me], [ZI261;CH₂(4-F-pyridin-2-yl),Me], [ZI262;CH₂(5-F-pyridin-2-yl),Me], [ZI263;CH₂(6-F-pyridin-2-yl),Me], [ZI264;CH₂(3-Cl-pyridin-2-yl),Me], [ZI265; CH₂(4-Cl-pyridin-2-yl),Me], [ZI266;CH₂(5-Cl-pyridin-2-yl),Me], [ZI267;CH₂(6-Cl-pyridin-2-yl),Me], [ZI268;CH₂ (3-Me-pyridin-2-yl),Me], [ZI269;CH₂(4-Me-pyridin-2-yl), Me], [ZI270;CH₂(5-Me-pyridin-2-yl),Me], [ZI271;CH₂(6-Me-pyridin-2-yl),Me], [ZI272;CH₂(3-OMe-pyridin-2-yl), Me], [ZI273;CH₂(4-OMe-pyridin-2-yl),Me], [ZI274;CH₂ (5-OMe-pyridin-2-yl),Me], [ZI275;CH₂(6-OMe-pyridin-2-yl),Me], [ZI276;CH₂(3-CF₃-pyridin-2-yl),Me], [ZI277;CH₂ (4-CF₃-pyridin-2-yl),Me], [ZI278;CH₂(5-CF₃-pyridin-2-yl), Me], [ZI279;CH₂(6-CF₃-pyridin-2-yl),Me], [ZI280;CH₂(3-CN-pyridin-2-yl),Me], [ZI281;CH₂(4-CN-pyridin-2-yl), Me], [ZI282;CH₂(5-CN-pyridin-2-yl),Me], [ZI283;CH₂(6-CN-pyridin-2-yl),Me], [ZI284;CH₂(2-F-pyridin-3-yl),Me], [ZI285;CH₂(4-F-pyridin-3-yl),Me], [ZI286;CH₂(5-F-pyridin-3-yl),Me], [ZI287;CH₂(6-F-pyridin-3-yl),Me], [ZI288; CH₂(2-Cl-pyridin-3-yl),Me], [ZI289;CH₂(4-Cl-pyridin-3- yl),Me], [ZI290;CH₂(5-Cl-pyridin-3-yl),Me], [ZI291;CH₂(6-Cl-pyridin-3-yl),Me], [ZI292;CH₂(2-Me-pyridin-3-yl),Me], [ZI293;CH₂(4-Me-pyridin-3-yl),Me], [ZI294;CH₂(5-Me-pyridin-3-yl),Me], [ZI295;CH₂(6-Me-pyridin-3-yl),Me], [ZI296;CH₂(2-OMe-pyridin-3-yl),Me], [ZI297;CH₂(4-OMe-pyridin-3-yl),Me], [ZI298;CH₂(5-OMe-pyridin-3-yl),Me], [ZI299;CH₂(6-OMe-pyridin-3-yl),Me], [ZI300;CH₂(2-CF₃-pyridin-3-yl),Me], [ZI301;CH₂(4-CF₃-pyridin-3-yl),Me], [ZI302;CH₂(5-CF₃-pyridin-3-yl),Me], [ZI303;CH₂(6-CF₃-pyridin-3-yl),Me], [ZI304;CH₂(2-CN-pyridin-3-yl),Me], [ZI305;CH₂(4-CN-pyridin-3-yl),Me], [ZI306;CH₂(5-CN-pyridin-3-yl),Me], [ZI307;CH₂(6-CN-pyridin-3-yl),Me], [ZI308;CH₂(2-F-pyridin-4-yl),Me], [ZI309;CH₂(3-F-pyridin-4-yl),Me], [ZI310;CH₂(2-Cl-pyridin-4-yl),Me], [ZI311;CH₂(3-Cl-pyridin-4-yl),Me], [ZI312;CH₂(2-Me-pyridin-4-yl),Me], [ZI313;CH₂(3-Me-pyridin-4-yl),Me], [ZI314;CH₂(2-OMe-pyridin-4-yl),Me], [ZI315;CH₂(3-OMe-pyridin-4-yl),Me], [ZI316;CH₂(2-CF₃-pyridin-4-yl),Me], [ZI317;CH₂(3-CF₃-pyridin-4-yl),Me], [ZI318;CH₂(2-CN-pyridin-4-yl),Me], [ZI319;CH₂(3-CN-pyridin-4-yl),Me], [ZI320;CH₂(2-Thienyl),Me], [ZI321;CH₂(3-Thienyl),Me], [ZI322;CH₂(2-pyrimidinyl),Me], [ZI323;CH₂(4-pyrimidinyl),Me], [ZI324;CH₂(5-pyrimidinyl),Me], [ZI325;CH₂(3-pyridazinyl),Me], [ZI326;CH₂(4-pyridazinyl),Me], [ZI327;(CH₂)₂Ph,Me], [ZI328;(CH₂)₃Ph,Me],[ZI329;CH₂OMe,Me], [ZI330;CH₂OEt,Me], [ZI331;CH₂OPr,Me], [ZI332;CH₂OPh,Me], [ZI333;CH₂CN,Me], [ZI334;Ph,Me], [ZI335;2-F-Ph,Me], [ZI336;3-F-Ph,Me], [ZI337;4-F-Ph,Me], [ZI338;2-Cl-Ph,Me], [ZI339;3-Cl-Ph,Me], [ZI340;4-Cl-Ph,Me], [ZI341;2-Me-Ph,Me], [ZI342;3-Me-Ph,Me], [ZI343;4-Me-Ph,Me], [ZI344;2-OMe-Ph,Me], [ZI345;3-OMe-Ph,Me],[ZI346;4-OMe-Ph,Me], [ZI347;2-Pyridyl,Me], [ZI348;3-Pyridyl,Me], [ZI349;4-Pyridyl,Me], [ZI350;2-Thienyl,Me], [ZI351;3-Thienyl,Me], [ZI352;2-pyrimidinyl,Me], [ZI353;4-pyrimidinyl,Me], [ZI354;5-pyrimidinyl,Me], [ZI355;3-pyridazinyl,Me], [ZI356;4-pyridazinyl,Me], [ZI357;Me,Et], [ZI358;Et,Et], [ZI359;Pr,Et], [ZI360;Bu,Et], [ZI361;Pen,Et], [ZI362;Hex,Et], [ZI363;i-Pr,Et], [ZI364;i-Bu,Et], [ZI365;t-Bu,Et], [ZI366;c-Pr,Et], [ZI367;c-Bu,Et], [ZI368;c-Pen,Et], [ZI369;c-Hex,Et], [ZI370;CH₂c-Pr,Et], [ZI371;CH₂c-Pen,Et], [ZI372;CH₂c-Hex,Et], [ZI373;CH₂CH=CH₂,Et], [ZI374;CH₂CH=CHMe,Et], [ZI375;CH2CH=CMe₂,Et], [ZI376;CH₂C≡CH,Et], [ZI377;CH₂C≡CMe,Et], [ZI378;CH₂Ph,Et], [ZI379;CH₂(2-F-Ph),Et], [ZI380;CH₂(3-F-Ph),Et], [ZI381;CH₂(4-F-Ph),Et], [ZI382;CH₂(2-Cl-Ph),Et], [ZI383;CH₂(3-Cl-Ph),Et], [ZI384;CH₂(4-Cl-Ph),Et], [ZI385;CH₂(2-Br-Ph),Et], [ZI386;CH₂(3-Br-Ph),Et], [ZI387;CH₂(4-Br-Ph),Et], [ZI388;CH₂(2-Me-Ph),Et], [ZI389;CH₂(3-Me-Ph),Et], [ZI390;CH₂(4-Me-Ph),Et], [ZI391;CH₂(2-Et-Ph),Et], [ZI392;CH₂(3-Et-Ph),Et], [ZI393;CH₂(4-Et-Ph),Et], [ZI394;CH₂(2-t-Bu-Ph),Et], [ZI395;CH₂(3-t-Bu-Ph),Et], [ZI396;CH₂(4-t-Bu-Ph),Et], [ZI397;CH₂(2-CF₃-Ph),Et], [ZI398;CH₂(3-CF₃-Ph),Et], [ZI399;CH₂(4-CF₃-Ph),Et], [ZI400;CH₂(2-OMe-Ph),Et], [ZI401;CH₂(3-OMe-Ph),Et], [ZI402;CH₂(4-OMe-Ph),Et], [ZI403;CH₂(2-SMe-Ph),Et], [ZI404;CH₂(3-SMe-Ph),Et], [ZI405;CH₂(4-SMe-Ph),Et], [ZI406;CH₂(2-CN-Ph),Et], [ZI407;CH₂(3-CN-Ph),Et], [ZI408;CH₂(4-CN-Ph),Et], [ZI409;CH₂(2,4-F₂-Ph),Et], [ZI410;CH₂(2,5-F₂-Ph),Et], [ZI411;CH₂(3,4-F₂-Ph),Et], [ZI412;CH₂(3,5-F₂-Ph),Et], [ZI413;CH₂(2,4-Cl₂-Ph),Et], [ZI414;CH₂(2,5-Cl₂-Ph),Et], [ZI415;CH₂(3,4-Cl₂-Ph),Et], [ZI416;CH₂(3,5-Cl₂-Ph),Et], [ZI417;CH₂(2,4-Me₂-Ph),Et], [ZI418;CH₂(2,5-Me₂-Ph),Et], [ZI419;CH₂(3,4-Me₂-Ph),Et], [ZI420;CH₂(3,5-Me₂-Ph),Et], [ZI421;CH₂(2-F-4-Cl-Ph),Et], [ZI422;CH₂(3-F-4-Cl-Ph),Et], [ZI423;CH₂(2-F-4-Me-Ph),Et], [ZI424;CH₂(2-Me-4-F-Ph),Et], [ZI425;CH₂(2-F-4-OMe-Ph),Et], [ZI426;CH₂(2-OMe-4-F-Ph),Et], [ZI427;CH₂(2-Me-4-Cl-Ph),Et], [ZI428;CH₂(2-Cl-4-Me-Ph),Et], [ZI429;CH₂(2-Me-4-OMe-Ph),Et], [ZI430;CH₂(2-OMe-4-Me-Ph),Et], [ZI431;CH₂(2-Cl-4-OMe-Ph),Et], [ZI432;CH₂(2-OMe-4-Cl-Ph),Et], [ZI433;CH₂(2,4,6-F₃-Ph),Et], [ZI434;CH₂(3,4,5-F₃-Ph),Et], [ZI435;CH₂(2-pyridyl),Et], [ZI436;CH₂(3-pyridyl),Et], [ZI437;CH₂(4-pyridyl),Et], [ZI438;CH₂(3-F-pyridin-2-yl),Et], [ZI439;CH₂(4-F-pyridin-2-yl),Et], [ZI440;CH₂(5-F-pyridin-2-yl),Et], [ZI441;CH₂(6-F-pyridin-2-yl),Et], [ZI442;CH₂(3-Cl-pyridin-2-yl),Et], [ZI443;CH₂(4-Cl-pyridin-2-yl),Et], [ZI444;CH₂(5-Cl-pyridin-2-yl),Et], [ZI445;CH₂(6-Cl-pyridin-2-yl),Et], [ZI446;CH₂(3-Me-pyridin-2-yl),Et], [ZI447;CH₂(4-Me-pyridin-2-yl),Et], [ZI448;CH₂(5-Me-pyridin-2-yl),Et], [ZI449;CH₂(6-Me-pyridin-2-yl),Et], [ZI450;CH₂(3-OMe-pyridin-2-yl),Et], [ZI451;CH₂(4-OMe-pyridin-2-yl),Et], [ZI452;CH₂(5-OMe-pyridin-2-yl),Et], [ZI453;CH₂(6-OMe-pyridin-2-yl),Et], [ZI454;CH₂(3-CF₃-pyridin-2-yl),Et], [ZI455;CH₂(4-CF₃-pyridin-2-yl),Et], [ZI456;CH₂(5-CF₃-pyridin-2-yl),Et], [ZI457;CH₂(6-CF₃-pyridin-2-yl),Et], [ZI458;CH₂(3-CN-pyridin-2-yl),Et], [ZI459;CH₂(4-CN-pyridin-2-yl),Et], [ZI460;CH₂(5-CN-pyridin-2-yl),Et], [ZI461;CH₂(6-CN-pyridin-2-yl),Et], [ZI462;CH₂(2-F-pyridin-3-yl),Et], [ZI463;CH₂(4-F-pyridin-3-yl),Et], [ZI464;CH₂(5-F-pyridin-3-yl),Et], [ZI465;CH₂(6-F-pyridin-3-yl),Et], [ZI466;CH₂(2-Cl-pyridin-3-yl),Et], [ZI467;CH₂(4-Cl-pyridin-3-yl),Et], [ZI468;CH₂(5-Cl-pyridin-3-yl),Et], [ZI469;CH₂(6-Cl-pyridin-3-yl),Et], [ZI470;CH₂(2-Me-pyridin-3-yl),Et], [ZI471;CH₂(4-Me-pyridin-3-yl),Et], [ZI472;CH₂(5-Me-pyridin-3-yl),Et], [ZI473;CH₂(6-Me-pyridin-3-yl),Et], [ZI474;CH₂(2-OMe-pyridin-3-yl),Et], [ZI475;CH₂(4-OMe-pyridin-3-yl),Et], [ZI476;CH₂(5-OMe-pyridin-3-yl),Et], [ZI477;CH₂(6-OMe-pyridin-3-yl),Et], [ZI478;CH₂(2-CF₃-pyridin-3-yl),Et], [ZI479;CH₂(4-CF₃-pyridin-3-yl),Et], [ZI480;CH₂(5-CF₃-pyridin-3-yl),Et], [ZI481;CH₂(6-CF₃-pyridin-3-yl),Et], [ZI482;CH₂(2-CN-pyridin-3-yl),Et], [ZI483;CH₂(4-CN-pyridin-3-yl),Et], [ZI484;CH₂(5-CN-pyridin-3-yl),Et], [ZI485;CH₂(6-CN-pyridin-3-yl),Et], [ZI486;CH₂(2-F-pyridin-4-yl),Et], [ZI487;CH₂(3-F-pyridin-4-yl),Et], [ZI488;CH₂(2-Cl-pyridin-4-yl),Et], [ZI489;CH₂(3-Cl-pyridin-4-yl),Et], [ZI490;CH₂(2-Me-pyridin-4-yl),Et], [ZI491;CH₂(3-Me-pyridin-4-yl),Et], [ZI492;CH₂(2-OMe-pyridin-4-yl),Et], [ZI493;CH₂(3-OMe-pyridin-4-yl),Et], [ZI494;CH₂(2-CF₃-pyridin-4-yl),Et], [ZI495;CH₂(3-CF₃-pyridin-4-yl),Et], [ZI496;CH₂(2-CN-pyridin-4-yl),Et], [ZI497;CH₂(3-CN-pyridin-4-yl),Et], [ZI498;CH₂(2-Thienyl),Et], [ZI499;CH₂(3-Thienyl),Et], [ZI500;CH₂(2-pyrimidinyl),Et], [ZI501;CH₂(4-pyrimidinyl),Et], [ZI502;CH₂(5-pyrimidinyl),Et], [ZI503;CH₂(3-pyridazinyl),Et], [ZI504;CH₂(4-pyridazinyl),Et], [ZI505;(CH₂)₂Ph,Et], [ZI506;(CH₂)₃Ph,Et], [ZI507;CH₂OMe,Et], [ZI508;CH₂OEt,Et], [ZI509;CH₂OPr,Et], [ZI510;CH₂OPh,Et], [ZI511; CH₂CN,Et], [ZI512; Ph, Et], [ZI513;2-F-Ph,Et], [ZI514;3-F-Ph,Et], [ZI515;4-F-Ph,Et], [ZI516;2-Cl-Ph,Et], [ZI517;3-Cl-Ph,Et], [ZI518;4-Cl-Ph,Et], [ZI519;2-Me-Ph,Et], [ZI520;3-Me-Ph,Et], [ZI521;4-Me-Ph,Et], [ZI522;2-OMe-Ph,Et], [ZI523;3-OMe-Ph,Et], [ZI524;4-OMe-Ph,Et], [ZI525;2-Pyridyl,Et], [ZI526;3-Pyridyl,Et], [ZI527;4-Pyridyl,Et], [ZI528;2-Thienyl,Et], [ZI529;3-Thienyl,Et], [ZI530;2-pyrimidinyl,Et], [ZI531;4-pyrimidinyl,Et], [ZI532;5-pyrimidinyl,Et], [ZI533;3-pyridazinyl,Et], [ZI534;4-pyridazinyl,Et].

A compound represented by formula (1I) wherein Q represents a group represented by Q1, L represents an oxygen atom, $R^1$ represents a chlorine atom, and a combination of $R^{x27}$ and $R^{x28}$ represents any combination indicated in the combination H (hereinafter, referred to as Compound Class SX122).

A compound represented by formula (1I) wherein Q represents a group represented by Q1, L represents an oxygen atom, $R^1$ represents a chlorine atom, and a combination of $R^{x27}$ and $R^{x28}$ represents any combination indicated in the combination H (hereinafter, referred to as Compound Class SX123).

A compound represented by formula (1I) wherein Q represents a group represented by Q1, L represents $CH_2$, $R^1$ represents a chlorine atom, and a combination of $R^{x27}$ and $R^{x28}$ represents any combination indicated in the combination H (hereinafter, referred to as Compound Class SX124).

A compound represented by formula (1I) wherein Q represents a group represented by Q1, L represents $NCH_3$, $R^1$ represents a hydrogen atom, and a combination of $R^{x27}$ and $R^{x28}$ represents any combination indicated in the combination H (hereinafter, referred to as Compound Class SX125).

A compound represented by formula (11) wherein Q represents a group represented by Q2, X represents an oxygen atom, $R^1$ represents a methyl group, and a combination of $R^{x27}$ and $R^{x28}$ represents any combination indicated in the combination H (hereinafter, referred to as Compound Class SX126).

A compound represented by formula (11) wherein Q represents a group represented by Q2, X represents an oxygen atom, $R^1$ represents a chlorine atom, and a combination of $R^{x27}$ and $R^{x28}$ represents any combination indicated in the combination H (hereinafter, referred to as Compound Class SX127).

A compound represented by formula (11) wherein Q represents a group represented by Q2, X represents NH, $R^1$ represents a methyl group, and a combination of $R^{x27}$ and $R^{x28}$ represents any combination indicated in the combination H (hereinafter, referred to as Compound Class SX128).

A compound represented by formula (11) wherein Q represents a group represented by Q2, X represents NH, $R^1$ represents a chlorine atom, and a combination of $R^{x27}$ and $R^{x28}$ represents any combination indicated in the combination H (hereinafter, referred to as Compound Class SX129).

A compound represented by formula (11) wherein Q represents a group represented by Q3, $R^3$ represents a difluoromethyl group, $R^1$ represents a methyl group, and a combination of $R^{x27}$ and $R^{x28}$ represents any combination indicated in the combination H (hereinafter, referred to as Compound Class SX130).

A compound represented by formula (11) wherein Q represents a group represented by Q3, $R^3$ represents a difluoromethyl group, $R^1$ represents a chlorine atom, and a combination of $R^{x27}$ and $R^{x28}$ represents any combination indicated in the combination H (hereinafter, referred to as Compound Class SX131).

A compound represented by formula (11) wherein Q represents a group represented by Q3, $R^3$ represents a methoxy group, $R^1$ represents a methyl group, and a combination of $R^{x27}$ and $R^{x28}$ represents any combination indicated in the combination H (hereinafter, referred to as Compound Class SX132).

A compound represented by formula (1I) wherein Q represents a group represented by Q3, $R^3$ represents a methoxy group, $R^1$ represents a chlorine atom, and a combination of $R^{x27}$ and $R^{x28}$ represents any combination indicated in the combination H (hereinafter, referred to as Compound Class SX133).

A compound represented by formula (1I) wherein Q represents a group represented by Q4, $R^1$ represents a methyl group, and a combination of $R^{x27}$ and $R^{x28}$ represents any combination indicated in the combination H (hereinafter, referred to as Compound Class SX134).

A compound represented by formula (1I) wherein Q represents a group represented by Q4, $R^1$ represents a chlorine atom, and a combination of $R^{x27}$ and $R^{x28}$ represents any combination indicated in the combination H (hereinafter, referred to as Compound Class SX135).

A compound represented by formula (III) wherein $E^B$ represents a cyclopropylethynyl group, n is 0, and a combination of $R^1$ and L represents any combination indicated in the combination J.

The combination J consists of the substituent number ZJ1 to ZJ534. The substituent number ZJ1 to ZJ534 represents any combinations of $R^1$ and L in the compound represented formula (III), and hereinafter, which is indicated as [Substituent Number; $R^1$, L]. For example, "Substituent Number ZJ1" represents a combination where $R^1$ represents a methyl group, and L represents an oxygen atom.

Combination J

[ZJ1;Me,O], [ZJ2;Me,CH2],[ZJ3;Me,NMe], [ZJ4;Cl,O], [ZJ5;Cl,CH$_2$], [ZJ6;Cl,NMe], [ZJ7;H$_2$O], [ZJ8;H,CH$_2$], [ZJ9;H,NMe].

A compound represented by formula (III) wherein $E^B$ represents a cyclobutylethynyl group, n is 0, and a combination of $R^1$ and L represents any combination indicated in the combination J.

A compound represented by formula (III) wherein $E^B$ represents a 2-cyclopropylvinyl group, n is 0, and a combination of $R^1$ and L represents any combination indicated in the combination J.

A compound represented by formula (III) wherein $E^B$ represents a 1-methyl-1-propenyl group, n is 0, and a combination of $R^1$ and L represents any combination indicated in the combination J.

A compound represented by formula (IV) wherein $E^B$ represents a cyclopropylethynyl group, n is 0, and a combination of $R^1$ and L represents any combination indicated in the combination J.

A compound represented by formula (IV) wherein $E^B$ represents a cyclobutylethynyl group, n is 0, and a combination of $R^1$ and L represents any combination indicated in the combination J.

A compound represented by formula (IV) wherein $E^B$ represents a 2-cyclopropylvinyl group, n is 0, and a combination of $R^1$ and L represents any combination indicated in the combination J.

A compound represented by formula (IV) wherein $E^B$ represents a 1-methyl-1-propenyl group, n is 0, and a combination of $R^1$ and L represents any combination indicated in the combination J.

The present compounds 1 to 51 as described herein are the compounds indicated below.

Present compound 1 represented by the following formula:

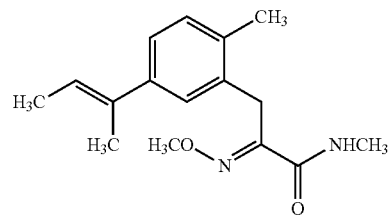 [SMILES: C/C=C(\C)c1ccc(C)c(C/C(=N\OC)C(=O)NC)c1]

Present Compound 1

Present compounds 2 to 4 which correspond to the compound represented by formula (1a) wherein a combination of $R^{30}$, $R^{31}$, and L represents the combinations indicated below.

Present Compound 2 ($R^{30}$:SiMe$_3$, $R^{31}$:Me, L:O),
Present Compound 3 ($R^{30}$:SiMe$_2$Ph, $R^{31}$:Me, L:O),
Present Compound 4 ($R^{30}$:t-Bu, $R^{31}$:Me, L:O).

Present Compounds 5 to 12 which correspond to a compound represented by formula (1b):

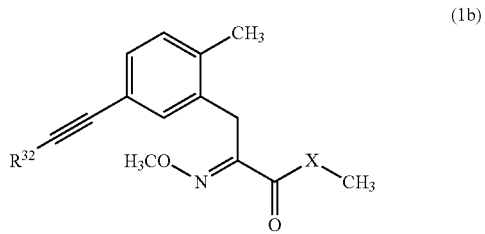

wherein a combination of $R^{32}$ and X represents the combinations indicated below.

Present Compound 5 ($R^{32}$:SiMe$_3$, X:O),
Present Compound 6 ($R^{32}$:t-Bu, X:O),
Present Compound 7 ($R^{32}$:c-Pr, X:O),
Present Compound 8 ($R^{32}$:Si(t-Bu)Me$_2$, X:NH),
Present Compound 9 ($R^{32}$:t-Bu, X:NH),
Present Compound 10 ($R^{32}$:c-Pr, X:NH),
Present Compound 11 ($R^{32}$:c-hex, X:NH),
Present Compound 12 ($R^{32}$:CMe$_2$(OMe), X:NH).

Present Compounds 13 and 14 which correspond to a compound represented by formula (1c):

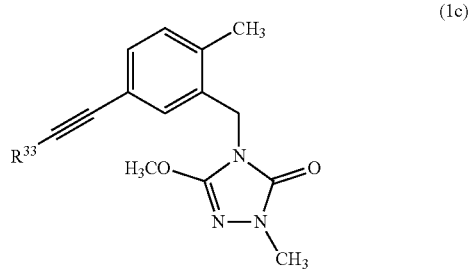

wherein $R^{33}$ represents the substituents indicated below.

Present Compound 13 ($R^{33}$: SiMe$_3$),
Present Compound 14 ($R^{33}$: c-Pr).

A compound represented by formula (1d) wherein a combination of $R^{34}$, $R^{35}$, $R^{36}$, $R^{36}$, $R^{37}$, $R^{38}$, $R^{39}$, and L represents any combinations indicated in [Table 1d].

TABLE 1d

| Present Compound | $R^{34}$ | $R^{35}$ | $R^{36}$ | $R^{37}$ | $R^{38}$ | $R^{39}$ | L |
|---|---|---|---|---|---|---|---|
| 15 | H | H | H | H | H | Me | O |
| 16 | H | Me | H | H | H | Me | O |
| 17 | H | CF$_3$ | H | H | H | Me | O |
| 18 | H | F | H | H | H | Me | O |
| 19 | H | Cl | H | H | H | Me | CH$_2$ |
| 20 | H | OMe | H | H | H | Me | O |
| 21 | H | H | Me | H | H | Me | O |
| 22 | H | H | F | H | H | Me | O |

TABLE 1d-continued

| Present Compound | $R^{34}$ | $R^{35}$ | $R^{36}$ | $R^{37}$ | $R^{38}$ | $R^{39}$ | L |
|---|---|---|---|---|---|---|---|
| 23 | H | H | Cl | H | H | Me | CH$_2$ |
| 24 | H | F | H | F | H | Me | O |
| 25 | H | H | H | H | H | H | NMe |
| 26 | H | H | H | H | H | Me | CH$_2$ |

A compound represented by formula (1e):

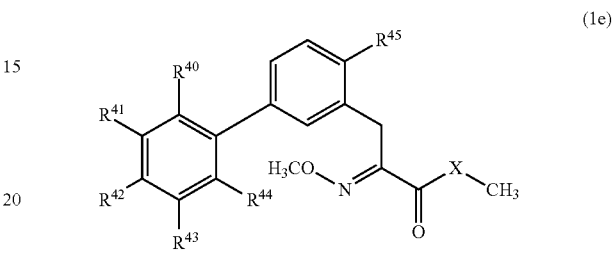

wherein a combination of $R^{40}$, $R^{41}$, $R^{42}$, $R^{43}$, $R^{44}$, $R^{45}$, and X represents any combinations indicated in [Table 1e].

TABLE 1e

| Present Compound | $R^{40}$ | $R^{41}$ | $R^{42}$ | $R^{45}$ | $R^{44}$ | $R^{45}$ | X |
|---|---|---|---|---|---|---|---|
| 27 | H | H | H | H | H | Me | O |
| 28 | H | H | Cl | H | H | Me | O |
| 29 | H | H | H | H | H | Me | NH |
| 30 | Cl | H | H | H | H | Me | NH |
| 31 | H | Me | H | H | H | Me | NH |
| 32 | H | CF$_3$ | H | H | H | Me | NH |
| 33 | H | F | H | H | H | Me | NH |
| 34 | H | H | CF$_3$ | H | H | Me | NH |
| 35 | H | H | F | H | H | Me | NH |
| 36 | H | H | Cl | H | H | Me | NH |
| 37 | H | Cl | Cl 7 | H | H | Me | NH |
| 89 | H | H | t-Bu | H | H | Me | NH |

A compound represented by formula (1f):

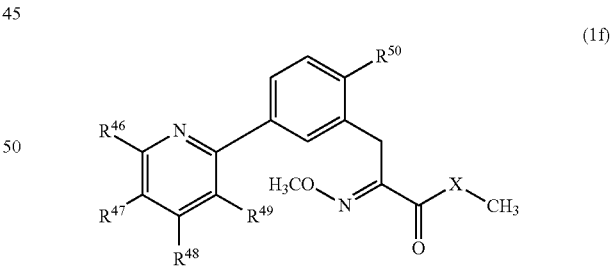

of $R^{46}$, $R^{47}$, $R^{48}$, $R^{49}$, $R^{50}$, wherein a combination and X represents any combinations indicated in [Table 1f].

TABLE 1f

| Present Compound | $R^{46}$ | $R^{47}$ | $R^{48}$ | $R^{49}$ | $R^{50}$ | X |
|---|---|---|---|---|---|---|
| 38 | Cl | H | H | H | Me | O |
| 39 | OPr | H | H | H | Me | O |

A compound represented by formula (1g):

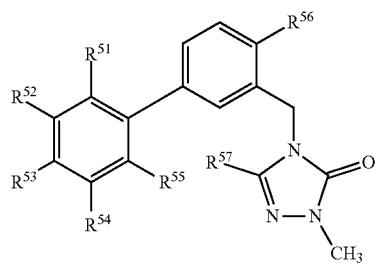

wherein a combination of $R^{51}$, $R^{52}$, $R^{53}$, $R^{54}$, $R^{55}$, $R^{56}$, and $R^{57}$ represents any combinations indicated in [Table 1g].

TABLE 1g

| Present Compound | $R^{51}$ | $R^{52}$ | $R^{53}$ | $R^{54}$ | $R^{55}$ | $R^{56}$ | $R^{57}$ |
|---|---|---|---|---|---|---|---|
| 40 | H | H | H | H | H | Me | $CF_2H$ |
| 90 | H | H | Me | H | H | Me | $CF_2H$ |
| 91 | F | H | H | H | H | Me | $CF_2H$ |
| 92 | H | F | H | H | H | Me | $CF_2H$ |
| 93 | H | H | F | H | H | Me | $CF_2H$ |
| 94 | H | Cl | H | H | H | Me | $CF_2H$ |

A compound represented by formula (1h):

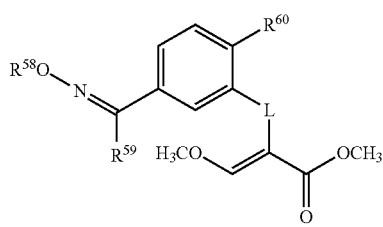

wherein a combination of $R^{58}$, $R^{59}$, $R^{60}$ and L represents any combinations indicated in [Table 1h].

TABLE 1h

| Present Compound | $R^{58}$ | $R^{59}$ | $R^{60}$ | L |
|---|---|---|---|---|
| 41 | Me | Me | Me | O |
| 42 | Pr | Me | Me | O |
| 43 | $(CH_2)_2CH(CH_3)_2$ | Me | Me | O |
| 44 | $CH_2C\equiv CH$ | Me | Me | O |
| 45 | $CH_2Ph$ | Me | Me | O |
| 46 | $CH_2(2\text{-Me}—Ph)$ | Me | Me | O |
| 47 | $CH_2(2\text{-F}—Ph)$ | Me | Me | O |
| 48 | $CH_2(3\text{-Me}—Ph)$ | Me | Me | O |
| 49 | $CH_2(4\text{-Me}—Ph)$ | Me | Me | O |
| 50 | $CH_2(3,4\text{-Me}_2—Ph)$ | Me | Me | O |

A compound represented by formula (1i):

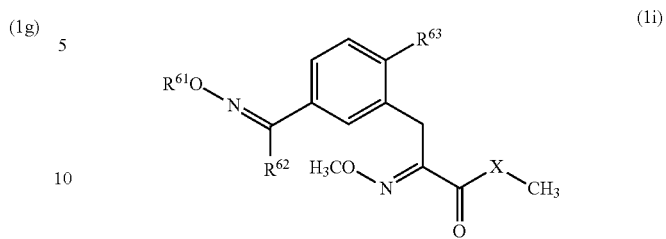

wherein a combination of $R^{61}$, $R^{62}$, $R^{63}$, and X represents the combinations indicated in [Table 1i].

TABLE 1i

| Present Compound | $R^{61}$ | $R^{62}$ | $R^{63}$ | X |
|---|---|---|---|---|
| 51 | Pr | Me | Me | NH |

Present Compounds 95 and 96 which correspond to a compound represented by formula (1j):

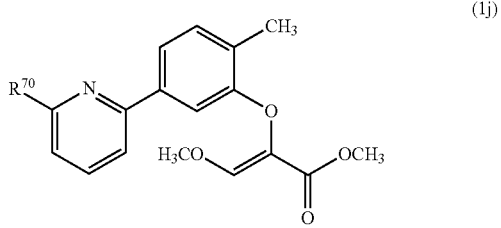

wherein a combination of $R^{70}$ represents the substituents indicated below.

Present Compound 95 ($R^{70}$: Cl),
Present Compound 96 ($R^{70}$: OPh).

Present Compound 97 which is represented by the following formula.

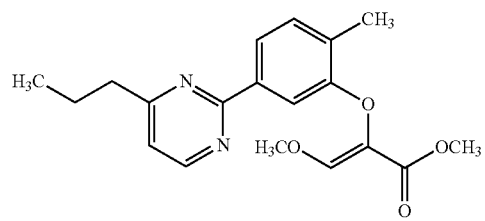 [SMILES: CCCc1ccnc(-c2ccc(C)c(O/C(=C\OC)C(=O)OC)c2)n1]

Present Compound 97

Next, the formulation examples are shown below. In the formulation examples, the "parts" represents "part by weight" unless otherwise specified. The present compound S represents the compounds described in the Compound Classes SX1 to SX135.

Formulation Example 1

Fifty (50) parts of any one of the present compound S, 3 parts of calcium lignin sulfonate, 2 parts of sodium lauryl sulfate, and 45 parts of wet silica are well mixed-grinding to obtain a formulation.

Formulation Example 2

Twenty (20) parts of any one of the present compound S, 1.5 parts of sorbitan trioleate are mixed with 28.5 parts of an aqueous solution containing 2 parts of polyvinyl alcohol, and the mixture is then finely-ground by a wet grinding method. To the mixture is then added 40 parts of an aqueous solution containing 0.05 parts of xanthan gum and 0.1 parts of magnesium aluminum silicate, and 10 parts of propylene glycol is further added thereto. The mixture is stirred to obtain a formulation.

Formulation Example 3

Two (2) parts of any one of the present compound S, 88 parts of kaolin clay and 10 parts of talc are mixed-grinding to obtain a formulation.

Formulation Example 4

Five (5) parts of any one of the present compound S, 14 parts of polyoxyethylene styryl phenyl ether, 6 parts of calcium dodecylbenzene sulfonate and 75 parts of xylene are well mixed to obtain a formulation.

Formulation Example 5

Five (5) parts of any one of the present compound S, 1 part of wet silica, 2 parts of calcium lignosulfonate, 30 parts of bentonite and 65 parts of kaolin clay are mixed-grinding, and thereto is added water, and the mixture is well kneaded and is then granulated and dried to obtain a formulation.

Formulation Example 6

Thirty five (35) parts of a mixture of ammonium polyoxyethylene alkyl ether sulfate and wet silica (weight ratio: 1:1), 20 parts of any one of the present compound S, and 45 parts of water are well mixed to obtain a formulation.

Next, Test Examples are described.

Test Example 1

Soybean leaf (cv; Kurosengoku) was punched out to 1 cm diameter to prepare a leaf disk. Each 1 mL of an agar medium (agar concentration 1.2%) was dispensed in 24 well microplate. A piece of the leaf disk was placed on each well. To a mixture of 0.5 μL of Sorpol (registered trademark) 1200KX, 4.5 μL of DMSO, and 5 μL of xylene was added 20 μL of a solution containing 10000 ppm of the test compound in DMSO. The resulting mixture was diluted with ion exchange water to prepare a spray solution containing a predetermined concentration of the test compound. The spray solution was sprayed in 10 μL per one leaf disk. After 1 day, an aqueous suspension of spores of soybean rust fungus (*Phakopsora pachyrhizi*) having an amino acid substitution of F129L on mitochondrial cytochrome b protein ($1.0\times10^5$/mL) was inoculated onto the leaf disks. After the inoculation, the microplate was placed in a growth chamber (light on for 6 hours, light off for 18 hours, 23° C. temperature, 60% humidity). After 1 day, the leaf disks were air-dried to disappear water droplets on the surface of the leaf disk, and the microplate was placed again in the growth chamber for 12 days. Thereafter, a lesion area of soybean rust disease was assessed. As a result, in all cases, the lesion areas of the leaf disk on which any one of the present compounds 1 to 98 or the compounds 1 to 9 of the present invention was applied as a test compound at 12.5 ppm was shown to 30% or less of the lesion area of the untreated leaf disk. Here the untreated means that the spray solution containing the test compound was not sprayed onto the leaf disk.

Comparative Test Example 1

The test was conducted by using as a test compound the compound 3 or 8 of the present invention, the present compound 6, 12, 13, 22, 38, 40, 48, 51, 64 or 84, pyraclostrobin, azoxystrobin, picoxystrobin, orysastrobin, dimoxystrobin, metominostrobin, or pyribencarb at 12.5 ppm or 3.1 ppm according to a method described in the Test Example 1. The results are indicated in [Table A], [Table B], and [Table C].

TABLE A

| Compound | Lesion area (%) at each concentration | |
|---|---|---|
| | 12.5 ppm | 3.1 ppm |
| 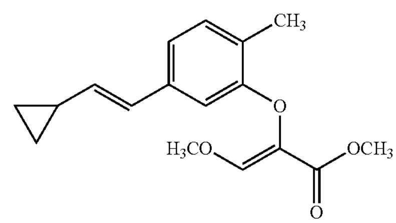 [SMILES: CO/C=C(\Oc1cc(/C=C/C2CC2)ccc1C)C(=O)OC]  Compound 3 of the present invention | 0 | 10 |
| 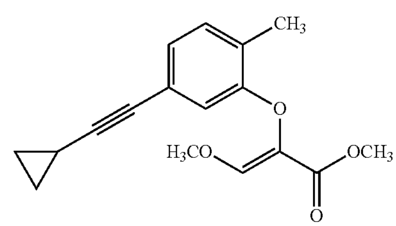 [SMILES: CO/C=C(\Oc1cc(C#CC2CC2)ccc1C)C(=O)OC]  Compound 8 of the present invention | 0 | 0 |
| 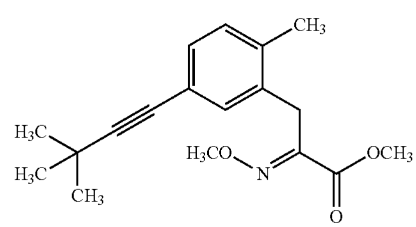 [SMILES: CO/N=C(\Cc1cc(C#CC(C)(C)C)ccc1C)C(=O)OC]  Present Compound 6 | 0 | 0 |

TABLE A-continued
| Compound | Lesion area (%) at each concentration | |
|---|---|---|
| | 12.5 ppm | 3.1 ppm |
| 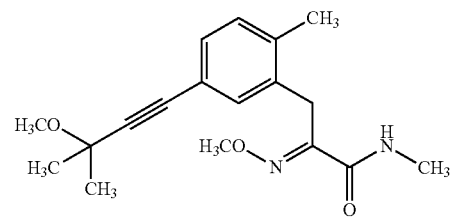 [SMILES: CNC(=O)/C(Cc1cc(C#CC(C)(C)OC)ccc1C)=N/OC] Present Compound 12 | 0 | 0 |
| 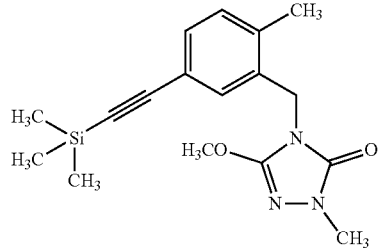 [SMILES: COc1nn(C)c(=O)n1Cc1cc(C#C[Si](C)(C)C)ccc1C] Present Compound 13 | 0 | 30 |
| 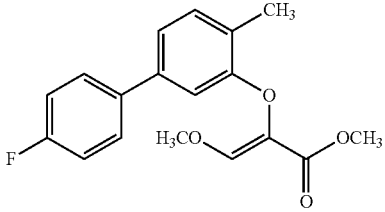 [SMILES: CO/C=C(\Oc1cc(-c2ccc(F)cc2)ccc1C)C(=O)OC] Present Compound 22 | 0 | 10 |
TABLE A-continued
| Compound | Lesion area (%) at each concentration | |
|---|---|---|
| | 12.5 ppm | 3.1 ppm |
| 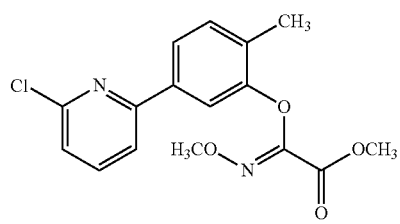 [SMILES: CO/N=C(\Oc1cc(-c2cccc(Cl)n2)ccc1C)C(=O)OC] Present Compound 38 | 0 | 50 |
| 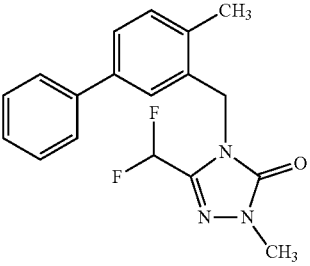 [SMILES: Cc1ccc(-c2ccccc2)cc1Cn1c(C(F)F)nn(C)c1=O] Present Compound 40 | 0 | 0 |
| 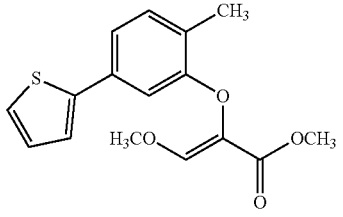 [SMILES: CO/C=C(\Oc1cc(-c2cccs2)ccc1C)C(=O)OC] Present Compound 64 | 0 | 10 |
TABLE B
| Compound | Lesion area (%) 12.5 ppm |
|---|---|
| 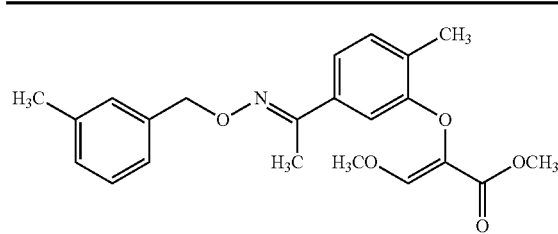 Present Compound 48 | 0 |

TABLE B-continued
| Compound | Lesion area (%) 12.5 ppm |
|---|---|
| 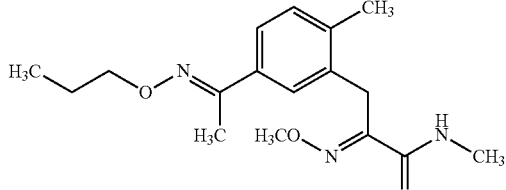<br>Present Compound 51 | 0 |
| 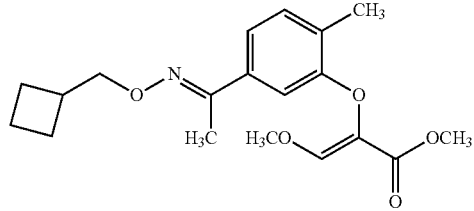 [SMILES: CO/C=C(\Oc1cc(/C(C)=N/OCC2CCC2)ccc1C)C(=O)OC]<br>Present Compound 84 | 0 |
TABLE C
| Compound | Lesion area (%) at each concentration | |
|---|---|---|
| | 12.5 ppm | 3.1 ppm |
| 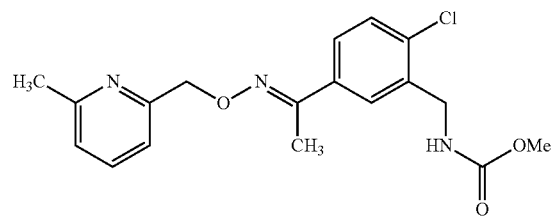 [SMILES: COC(=O)NCc1cc(/C(C)=N/OCc2cccc(C)n2)ccc1Cl]<br>pyribencarb | 100 | 100 |
| 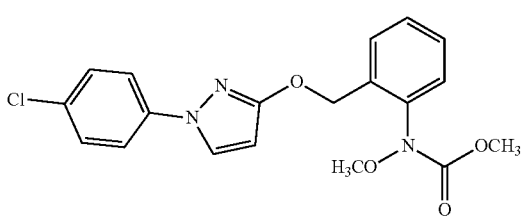 [SMILES: COC(=O)N(OC)c1ccccc1COc1ccn(-c2ccc(Cl)cc2)n1]<br>pyraclostrobin | 100 | 100 |
| 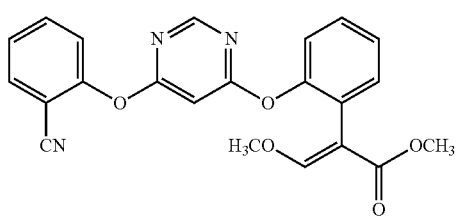 [SMILES: CO/C=C(/C(=O)OC)c1ccccc1Oc1cc(Oc2ccccc2C#N)ncn1]<br>azoxystrobin | 100 | 100 |

TABLE C-continued
| Compound | Lesion area (%) at each concentration | |
|---|---|---|
| | 12.5 ppm | 3.1 ppm |
| 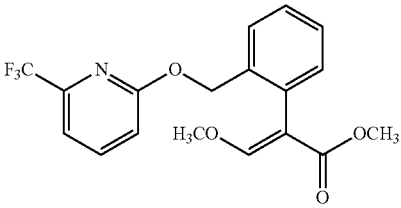 [SMILES: CO/C=C(/C(=O)OC)c1ccccc1COc1cccc(C(F)(F)F)n1] picoxystrobin | 100 | 100 |
| 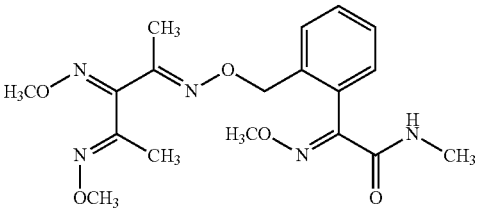 [SMILES: CNC(=O)/C(=N/OC)c1ccccc1CO/N=C(C)/C(=N/OC)C(/C)=N/OC] orysastrobin | 100 | 100 |
| 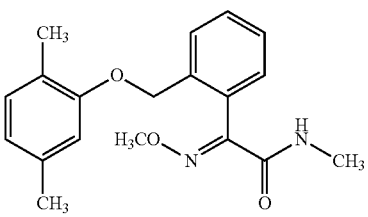 [SMILES: CNC(=O)/C(=N/OC)c1ccccc1COc1cc(C)ccc1C] dimoxystrobin | 100 | 100 |
| 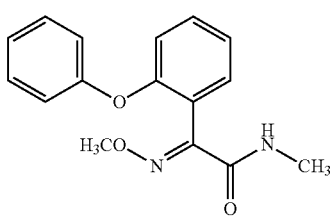 [SMILES: CNC(=O)/C(=N/OC)c1ccccc1Oc1ccccc1] metominostrobin | 100 | 100 |

The above-indicated results suggests that the present compound or the compound of the present invention has superior efficacies for soybean rust fungus having an amino acid substitution of F129L in comparison with various commercially available QoI fungicides.

INDUSTRIAL APPLICABILITY

The present compound, the compound of the present invention, or the composition A has efficacies for controlling soybean rust fungus having an amino acid substitution of F129L on mitochondrial cytochrome b protein.

The invention claimed is:

1. A compound represented by formula (II) or its N oxide, or an agriculturally acceptable salt thereof:

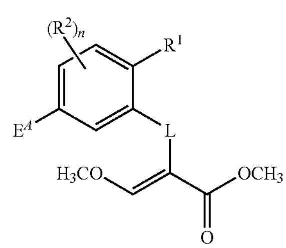

(II)

wherein

L represents $CH_2$, an oxygen atom, or $NCH_3$, $E^A$ represents $R^4R^5C{=}C(R^6)$—, or a 1-pyrazolyl group, wherein the 1-pyrazolyl group may be optionally substituted with one or more substituents selected from Group E, R¹ represents a C1-C3 chain hydrocarbon group optionally substituted with one or more halogen atoms, a cyclopropyl group, a halogen atom, or a hydrogen atom, n represents 0, 1, 2, or 3, when n is 2 or 3, a plural of R² may be identical to or different from each other, R² represents a C1-C3 chain hydrocarbon group optionally substituted with one or more halogen atoms, a cyclopropyl group, or a halogen atom, R⁴ and R⁶ are identical to or different from each other and represent a C1-C3 chain hydrocarbon group optionally substituted with one or more halogen atoms, a halogen atom, a cyano group, or a hydrogen atom, R⁵ represents a C1-C6 chain hydrocarbon group optionally substituted with one or more substituents selected from Group A, a C3-C6 cycloalkyl group optionally substituted with one or more substituents selected from Group B, a C6-C10 aryl group, a five- to ten-aromatic heterocyclic group, a halogen atom, a cyano group, or a hydrogen atom, wherein the C6-C10 aryl group, and the five- to ten-aromatic heterocyclic group each may be optionally substituted with one or more substituents selected from Group D, Group A: a group consisting of a C3-C6 cycloalkyl group, a C1-C4 alkoxy group, a C1-C4 alkylthio group, a halogen atom, a cyano group, a nitro group, a hydroxy group, a phenoxy group, a phenyl group, a naphthyl group, and a five- to six-membered aromatic heterocyclic group, wherein the C3-C6 cycloalkyl group, the C1-C4 alkoxy group, and the C1-C4 alkylthio group each may be optionally substituted with one or more substituents selected from the group consisting of halogen atom and cyano group, and wherein the phenoxy group, the phenyl group, the naphthyl group, and the five- to six-membered aromatic heterocyclic group each may be optionally substituted with one or more substituents selected from Group C, Group B: a group consisting of a C1-C6 chain hydrocarbon group, a C3-C6 cycloalkyl group, a C1-C4 alkoxy group, a C1-C4 alkylthio group, a halogen atom, a cyano group, a nitro group, a hydroxy group, a phenoxy group, a phenyl group, a naphthyl group, and a five- to six-membered aromatic heterocyclic group, wherein the C1-C6 chain hydrocarbon group, the C3-C6 cycloalkyl group, the C1-C4 alkoxy group, and the C1-C4 alkylthio group each may be optionally substituted with one or more substituents selected from the group consisting of halogen atom and cyano group, and wherein the phenoxy group, the phenyl group, the naphthyl group, and the five- to six-membered aromatic heterocyclic group each may be optionally substituted with one or more substituents selected from Group C, Group C: a group consisting of a C1-C6 chain hydrocarbon group, a C3-C6 cycloalkyl group, a C1-C6 alkoxy group, and a C1-C6 alkylthio group, a halogen atom, a cyano group, a nitro group, and a hydroxy group, wherein the C1-C6 chain hydrocarbon group, the C3-C6 cycloalkyl group, the C1-C6 alkoxy group, and the C1-C6 alkylthio group each may be optionally substituted with one or more substituents selected from the group consisting of halogen atom and cyano group, Group D: a group consisting of a C1-C6 chain hydrocarbon group optionally substituted with one or more substituents selected from Group A, a C3-C6 cycloalkyl group optionally substituted with one or more substituents selected from Group B, $OR^{11}$, $S(O)_mR^{13}$, $OS(O)_2R^{13}$, $C(O)R^{11}$, $C(O)OR^{11}$, $NR^{11}R^{12}$, $C(O)NR^{11}R^{12}$, $S(O)_2NR^{11}R^{12}$, $NR^{12}C(O)R^{11}$, $N^{12}$—$C(O)OR^{13}$, $NR^{12}S(O)_2R^{13}$, $C(R^{12})$=N—$OR^{11}$, a phenyl group, a naphthyl group, a five- to six-membered aromatic heterocyclic group, an oxo group, a thioxo group, a halogen atom, a cyano group, and a nitro group, wherein the phenyl group, the naphthyl group, and the five- to six-membered aromatic heterocyclic group each may be optionally substituted with one or more substituents selected from Group C, R¹¹ and R¹² are identical to or different from each other and represent a C1-C6 chain hydrocarbon group optionally substituted with one or more substituents selected from Group A, a C3-C6 cycloalkyl group optionally substituted with one or more substituents selected from Group B, a phenyl group, a naphthyl group, a five- to six-membered aromatic heterocyclic group, or a hydrogen atom, wherein the phenyl group, the naphthyl group, and the five- to six-membered aromatic heterocyclic group each may be optionally substituted with one or more substituents selected from Group C, and R¹³ represents a C1-C6 chain hydrocarbon group optionally substituted with one or more substituents selected from Group A, a C3-C6 cycloalkyl group optionally substituted with one or more substituents selected from Group B, a phenyl group, a naphthyl group, or a five- to six-membered aromatic heterocyclic group, wherein the phenyl group, the naphthyl group, and the five- to six-membered aromatic heterocyclic group each may be optionally substituted with one or more substituents selected from Group C, m is 0, 1, or 2, Group E: a group consisting of a C1-C6 chain hydrocarbon group optionally substituted with one or more substituents selected from Group A, a C3-C6 cycloalkyl group optionally substituted with one or more substituents selected from Group B, $OR^{11}$, $S(O)_mR^{13}$, $OS(O)_2R^{13}$, $C(O)R^{11}$, $C(O)OR^{11}$, $NR^{11}R^{12}$, $C(O)NR^{11}R^{12}$, $S(O)_2NR^{11}R^{12}$, $NR^{12}C(O)R^{11}$, $N^{12}$—$(O)_2R^{13}$, $NR^{12}S(O)_2R^{13}$, $C(R^{12})$=N—$OR^{11}$, a phenyl group, a naphthyl group, a five- to six-membered aromatic heterocyclic group, a halogen atom, a cyano group, and a nitro group, wherein the phenyl group, the naphthyl group, and the five- to six-membered aromatic heterocyclic group each may be optionally substituted with one or more substituents selected from Group C.

2. The compound according to claim 1 wherein

L represents $CH_2$ or an oxygen atom,

R¹ represents a methyl group or a chlorine atom, n is 0,

R⁴ and R⁶ are identical to or different from each other and represent a C1-C3 chain hydrocarbon group, or a hydrogen atom, and R⁵ represents a C1-C6 chain hydrocarbon group optionally substituted with one or more substituents selected from Group A, or a hydrogen atom, or its N oxide, or an agriculturally acceptable salt thereof.

3. An agricultural composition comprising the compound according to claim 1, or its N oxide, or an agriculturally acceptable salt thereof, and an inert carrier.

4. The agricultural composition according to claim 3, comprising one or more ingredients selected from Group (a), Group (b), Group (c) and Group (d),
- Group (a): a group consisting of insecticidal ingredients, miticidal ingredients, and nematicidal ingredients;
- Group (b): fungicidal ingredients;
- Group (c): plant growth modulating ingredients; and
- Group (d): repellent ingredients.

5. The agricultural composition according to claim 3, further comprising:
- at least one of an insecticidal ingredient, a miticidal ingredient, a nematicidal ingredient, a fungicidal ingredient, a plant growth modulating ingredient, or a repellent ingredient.

\* \* \* \* \*